US010508117B2

(12) United States Patent
Andres et al.

(10) Patent No.: US 10,508,117 B2
(45) Date of Patent: Dec. 17, 2019

(54) SOLID FORMS OF A TOLL-LIKE RECEPTOR MODULATOR

(71) Applicant: GILEAD SCIENCES, INC., Foster City, CA (US)

(72) Inventors: Patricia Andres, West Lafayette, IN (US); Krista Marie Diaz, West Lafayette, IN (US); Valeriya N. Smolenskaya, West Lafayette, IN (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 16/229,460

(22) Filed: Dec. 21, 2018

(65) Prior Publication Data

US 2019/0315750 A1 Oct. 17, 2019

Related U.S. Application Data

(63) Continuation of application No. 15/591,711, filed on May 10, 2017, now Pat. No. 10,202,384, which is a continuation of application No. 14/853,855, filed on Sep. 14, 2015, now Pat. No. 9,738,646.

(60) Provisional application No. 62/051,063, filed on Sep. 16, 2014.

(51) Int. Cl.
| | |
|---|---|
| *C07D 401/10* | (2006.01) |
| *C07D 475/06* | (2006.01) |
| *C07D 487/04* | (2006.01) |
| *A61K 31/519* | (2006.01) |
| *A61K 45/06* | (2006.01) |

(52) U.S. Cl.
CPC .......... *C07D 475/06* (2013.01); *A61K 31/519* (2013.01); *A61K 45/06* (2013.01); *C07D 487/04* (2013.01)

(58) Field of Classification Search
CPC .. C07D 401/10; C07D 475/06; C07D 487/04; A61K 31/519; A61K 45/06
See application file for complete search history.

(56) References Cited

U.S. PATENT DOCUMENTS

| | | |
|---|---|---|
| 3,798,209 A | 3/1974 | Witkowski et al. |
| 3,950,351 A | 4/1976 | Rossignol et al. |
| 4,539,205 A | 9/1985 | Goodman et al. |
| 4,639,436 A | 1/1987 | Junge et al. |
| 4,643,992 A | 2/1987 | Goodman et al. |
| 4,880,784 A | 11/1989 | Robins et al. |
| 5,011,828 A | 4/1991 | Goodman et al. |
| 5,041,426 A | 8/1991 | Robins et al. |
| 5,057,540 A | 10/1991 | Kensil et al. |
| 5,395,937 A | 3/1995 | Nikolaides et al. |
| 5,397,781 A | 3/1995 | Yanagibashi et al. |
| 5,424,311 A | 6/1995 | Billhardt-Troughton et al. |
| 5,620,978 A | 4/1997 | Cai et al. |
| 5,681,835 A | 10/1997 | Willson |
| 5,693,641 A | 12/1997 | Van Nest et al. |
| 6,028,076 A | 2/2000 | Hirota et al. |
| 6,268,391 B1 | 7/2001 | Dickerson et al. |
| 6,299,884 B1 | 10/2001 | Van Nest et al. |
| 6,329,381 B1 | 12/2001 | Kurimoto et al. |
| 6,376,501 B1 | 4/2002 | Isobe et al. |
| 6,552,192 B1 | 4/2003 | Hanuset et al. |
| 6,629,831 B2 | 10/2003 | Wei et al. |
| 7,157,465 B2 | 1/2007 | Isobe et al. |
| 7,521,454 B2 | 4/2009 | Isobe et al. |
| 7,592,326 B2 | 9/2009 | Karaolis |
| 7,642,350 B2 | 1/2010 | Pryde |
| 7,968,544 B2 | 6/2011 | Graupe et al. |
| 8,067,411 B2 | 11/2011 | Bonnert et al. |
| 8,067,426 B2 | 11/2011 | Biggadike et al. |
| 8,138,172 B2 | 3/2012 | Cook et al. |
| 8,148,374 B2 | 4/2012 | Desai et al. |
| 8,217,069 B2 | 7/2012 | Yonekubo et al. |
| 8,367,670 B2 | 2/2013 | Desai et al. |
| 8,476,270 B2 | 7/2013 | Halcomb et al. |
| 8,507,507 B2 | 8/2013 | Halcomb et al. |
| 8,629,142 B2 | 1/2014 | Desai et al. |
| 8,637,036 B2 | 1/2014 | Mascola et al. |
| 8,728,465 B2 | 5/2014 | Black et al. |
| 8,728,486 B2 | 5/2014 | David et al. |
| 8,729,088 B2 | 5/2014 | Carson et al. |
| 8,809,527 B2 | 8/2014 | Desai et al. |
| 9,127,006 B2 | 9/2015 | Desai et al. |
| 9,452,154 B2 | 9/2016 | Delaney, IV et al. |
| 9,452,166 B2 | 9/2016 | Desai et al. |
| 9,573,952 B2 | 2/2017 | Allen et al. |
| 9,738,646 B2 | 8/2017 | Brown et al. |
| 2002/0173655 A1 | 11/2002 | Dellaria et al. |

(Continued)

FOREIGN PATENT DOCUMENTS

| | | |
|---|---|---|
| CA | 2772253 A1 | 3/2011 |
| CN | 101663302 A | 3/2010 |

(Continued)

OTHER PUBLICATIONS

Ashizawa, et al., Iyakuhin no Takeigensho to Shoseki no Kagaku [Science of crystallization and polymorph phenomenon of pharmaceutical product], Maruzen Planet Co., Ltd, Sep. 20, 2002, pp. 305-317 [No English copy available].

(Continued)

*Primary Examiner* — Bruck Kifle
(74) *Attorney, Agent, or Firm* — Mintz, Levin, Cohn, Ferris, Glovsky and Popeo, P.C.

(57) ABSTRACT

The present invention provides crystalline forms, solvates and hydrates of 4-amino-2-butoxy-8-(3-(pyrrolidin-1-ylmethyl)benzyl)-7,8-dihydropteridin-6(5H)-one, and methods of making.

18 Claims, 34 Drawing Sheets

(56) References Cited

U.S. PATENT DOCUMENTS

| | | |
|---|---|---|
| 2003/0044428 A1 | 3/2003 | Moss et al. |
| 2003/0065005 A1 | 4/2003 | Charles et al. |
| 2003/0100764 A1 | 5/2003 | Bonk et al. |
| 2003/0162806 A1 | 8/2003 | Dellaria et al. |
| 2003/0176458 A1 | 9/2003 | Dellaria et al. |
| 2003/0186949 A1 | 10/2003 | Dellaria et al. |
| 2003/0195209 A1 | 10/2003 | Dellaria et al. |
| 2004/0029885 A1 | 2/2004 | Bauer et al. |
| 2004/0116362 A1 | 6/2004 | Sartorell et al. |
| 2004/0132748 A1 | 7/2004 | Isobe et al. |
| 2005/0043239 A1 | 2/2005 | Douangpanya et al. |
| 2006/0052403 A1 | 3/2006 | Isobe et al. |
| 2006/0269936 A1 | 11/2006 | Vlach et al. |
| 2007/0190071 A1 | 8/2007 | Kurimoto et al. |
| 2007/0197478 A1 | 8/2007 | Jones et al. |
| 2007/0197558 A1 | 8/2007 | Betebenner et al. |
| 2008/0008682 A1 | 1/2008 | Chong et al. |
| 2008/0167289 A1 | 7/2008 | Kay et al. |
| 2008/0182863 A1 | 7/2008 | Simmen et al. |
| 2008/0234255 A1 | 9/2008 | Chen |
| 2008/0269240 A1 | 10/2008 | Hashimoto et al. |
| 2008/0300244 A1 | 12/2008 | Bonnert et al. |
| 2009/0005560 A1 | 1/2009 | Oka et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0209524 A1 | 8/2009 | Bennett et al. |
| 2009/0221551 A1 | 9/2009 | Kshirsagar et al. |
| 2009/0221556 A1 | 9/2009 | Kshirsagar et al. |
| 2009/0221631 A1 | 9/2009 | Jones et al. |
| 2009/0263470 A1 | 10/2009 | Coller et al. |
| 2009/0291938 A1 | 11/2009 | Cao et al. |
| 2009/0324551 A1 | 12/2009 | Carson |
| 2009/0325877 A1 | 12/2009 | Grunt et al. |
| 2010/0015230 A1 | 1/2010 | Ron |
| 2010/0029585 A1 | 2/2010 | Howbert et al. |
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0143301 A1 | 6/2010 | Desai et al. |
| 2010/0152230 A1 | 6/2010 | Dellaria et al. |
| 2010/0210598 A1 | 8/2010 | Carson et al. |
| 2010/0215642 A1 | 8/2010 | Lan et al. |
| 2010/0240623 A1 | 9/2010 | Cook et al. |
| 2010/0256169 A1 | 10/2010 | Averett |
| 2010/0280001 A1 | 11/2010 | Bonnert et al. |
| 2010/0298364 A1 | 11/2010 | Bennett et al. |
| 2011/0028715 A1 | 2/2011 | Isobe et al. |
| 2011/0053893 A1 | 3/2011 | Wu et al. |
| 2011/0282061 A1 | 11/2011 | Johnson |
| 2012/0035193 A1 | 2/2012 | Biggadike et al. |
| 2013/0018042 A1 | 1/2013 | Howbert et al. |
| 2013/0109647 A1 | 5/2013 | Berrey et al. |
| 2013/0136776 A1 | 5/2013 | Cleary et al. |
| 2013/0236492 A1 | 9/2013 | Baudner et al. |
| 2013/0243726 A1 | 9/2013 | Ray et al. |
| 2014/0024664 A1 | 1/2014 | Bazin-Lee et al. |
| 2014/0045837 A1 | 2/2014 | Kurimoto et al. |
| 2014/0134132 A1 | 5/2014 | Fu et al. |
| 2014/0142086 A1 | 5/2014 | Howbert et al. |
| 2014/0170221 A1 | 6/2014 | Irvine |
| 2015/0105350 A1 | 4/2015 | Ramanathan |
| 2016/0008374 A1 | 1/2016 | Geleziunas et al. |

FOREIGN PATENT DOCUMENTS

| | | |
|---|---|---|
| CN | 103497192 A | 1/2014 |
| DE | 2220246 A1 | 12/1972 |
| DE | 2438037 A1 | 2/1975 |
| DE | 2758025 A1 | 7/1979 |
| EP | 1035123 A1 | 9/2000 |
| EP | 1147108 A1 | 10/2001 |
| EP | 01550662 | 7/2005 |
| EP | 1939201 A1 | 7/2008 |
| EP | 2132209 A1 | 12/2009 |
| EP | 2133353 A1 | 12/2009 |
| EP | 2138497 A1 | 12/2009 |
| EP | 2143724 A1 | 1/2010 |
| EP | 2364314 A1 | 9/2011 |
| EP | 3166607 A1 | 5/2017 |
| EP | 2477987 A1 | 1/2018 |
| EP | 3194402 B1 | 2/2018 |
| JP | 49001576 | 1/1974 |
| JP | 55111420 A | 8/1980 |
| JP | H-05320143 A | 12/1993 |
| JP | 1995330770 A | 6/1997 |
| JP | 2886570 A1 | 4/1999 |
| JP | 1999180982 A | 1/2001 |
| JP | 2005089334 A | 4/2005 |
| JP | 2009007273 A | 1/2009 |
| JP | 2014505045 A | 2/2014 |
| PT | 2364314 E | 6/2014 |
| TW | 200813057 A | 3/2008 |
| TW | 1401084 B | 7/2013 |
| WO | WO-1990014837 A1 | 12/1990 |
| WO | WO-1993019785 A1 | 10/1993 |
| WO | WO-1997044038 A1 | 11/1997 |
| WO | WO-1998001448 A1 | 1/1998 |
| WO | WO-1998005661 A1 | 2/1998 |
| WO | WO-1999028321 A1 | 6/1999 |
| WO | WO-1999032122 A1 | 7/1999 |
| WO | WO-1999032477 A1 | 7/1999 |
| WO | WO-2000000478 A1 | 1/2000 |
| WO | WO-2001019825 A1 | 3/2001 |
| WO | WO-2002076954 A1 | 10/2002 |
| WO | WO-2003020722 A1 | 3/2003 |
| WO | WO-2004029054 A1 | 4/2004 |
| WO | WO-2004076454 A1 | 9/2004 |
| WO | WO-2005016348 A1 | 2/2005 |
| WO | WO-2005016349 A1 | 2/2005 |
| WO | WO-2005067901 A3 | 7/2005 |
| WO | WO-2005112935 A1 | 12/2005 |
| WO | WO-2005117889 A1 | 12/2005 |
| WO | WO-2005120511 A1 | 12/2005 |
| WO | WO-2005123736 A1 | 12/2005 |
| WO | WO-2006034001 A2 | 3/2006 |
| WO | WO-2006089106 A3 | 8/2006 |
| WO | WO-2006117670 A1 | 11/2006 |
| WO | WO-2007014838 A1 | 2/2007 |
| WO | WO-2007024707 A3 | 3/2007 |
| WO | WO-2007034817 A1 | 3/2007 |
| WO | WO-2007034882 A1 | 3/2007 |
| WO | WO-2007034917 A1 | 3/2007 |
| WO | WO-2007089334 A3 | 8/2007 |
| WO | WO-2007108968 A3 | 9/2007 |
| WO | WO-2007142755 A3 | 12/2007 |
| WO | WO-2007148064 A1 | 12/2007 |
| WO | WO-2008004948 A1 | 1/2008 |
| WO | WO-2008051493 A3 | 5/2008 |
| WO | WO-2008055870 A1 | 5/2008 |
| WO | WO-2008101867 A5 | 8/2008 |
| WO | WO-2008113711 A1 | 9/2008 |
| WO | WO-2008129994 A1 | 10/2008 |
| WO | WO-2008135791 A1 | 11/2008 |
| WO | WO-2009005687 A1 | 1/2009 |
| WO | WO-2009019553 A2 | 2/2009 |
| WO | WO-2009022185 A3 | 2/2009 |
| WO | WO-2009023269 A3 | 2/2009 |
| WO | WO-2009062285 A1 | 5/2009 |
| WO | WO-2009067547 A1 | 5/2009 |
| WO | WO-2010018130 A1 | 2/2010 |
| WO | WO-2010018131 A1 | 2/2010 |
| WO | WO-2010018132 A1 | 2/2010 |

(56) References Cited

FOREIGN PATENT DOCUMENTS

| | | |
|---|---|---|
| WO | WO-2010018134 A1 | 2/2010 |
| WO | WO-2010077613 A1 | 7/2010 |
| WO | WO-2010107939 A2 | 9/2010 |
| WO | WO-2010130034 A1 | 11/2010 |
| WO | WO-2011031965 A1 | 3/2011 |
| WO | WO-2011049825 A1 | 4/2011 |
| WO | WO-2012003497 A1 | 1/2012 |
| WO | WO-2012003498 A1 | 1/2012 |
| WO | WO-2012030904 A2 | 3/2012 |
| WO | WO-2012087596 A1 | 6/2012 |
| WO | WO-2012145728 A1 | 10/2012 |
| WO | WO-2013068438 A1 | 5/2013 |
| WO | WO-2013159064 A1 | 10/2013 |
| WO | WO-2014063059 A1 | 4/2014 |
| WO | WO-2015048770 A2 | 4/2015 |
| WO | WO-2016007765 A1 | 1/2016 |
| WO | WO-2016044182 A1 | 3/2016 |

OTHER PUBLICATIONS

Barouch, et al., Therapeutic efficacy of potent neutralizing HIV-1-specific monoclonal antibodies in SHIV-infected rhesus monkeys, Nature, 2013, pp. 224-239, vol. 503.

Barr, et al., ISCOMSs and other saponin based adjuvants, Advanced Drug Delivery Reviews, 1998, pp. 247-271, vol. 32.

Barton, et al., Prospects for Treatment of Latent HIV, Nature.com, 2013, pp. 46-56, vol. 93, No. 1.

Battistini, et al., HIV-1 Latency: An Update of Molecular Mechanisms and Therapeutic Strategies, Viruses, 2014, pp. 1715-1758, vol. 6.

Borducchi, et al., Antibody and TLR7 Agonist Delay Viral Rebound in SHIV-Infected Monkeys, Nature, Oct. 3, 2018, 21 pages, vol. 564.

Boyer, et al., Pathogenesis, diagnosis, and management of hepatitis C, J. of Hepatology, Supp. 1, 2000, pp. 98-112.

Boyle, et al., Synthesis of a 2,4-Diaminodihydrohomopteridine, 6-Acetyl-2,4-Diamino-7,8-Dihydro-9H-Pyrimido[4,5-b][1,4]Diazepine, Using a Furazano[3,4-d]Pyrimidine Precursor, Tetrahedron, 1991, pp. 5259-5268, vol. 28.

Breault, et al., Exploring 8-benzyl pteridine-6,7-diones as inhibitors of glutamate recemase (Mur1) in Gram-positive bacteria, Bioorganic & Medicinal Chemistry Letters, Dec. 1, 2008, p. 6101; figure 2; compound 2; p. 6102; tables 2-3; compounds 0-12, 14-16; p. 6103; table 4; compound 25.

Brittain, Polymorphism in Pharmaceutical Solids, 1999, 25 pages.

Buffa, et al., Evaluaton of TLR Agonists as Potential Mucosal Adjuvants for HIV gp140 and Tetanus Toxoid in Mice, PLOS ONE, 2012, 10 pages, vol. 7, No. 12.

Buitendijk, Gardiquimod: A Toll-Like Receptor-7 Agonist that Inhibits HIV Type 1 Infection of Human Macrophages and Activated T Cells, Immunology, AIDS Research and Human Retroviruses, 2013, pp. 907-918, vol. 29, No. 6.

Caira, Crystalline Polymorphism of Organic Compounds, Topics in Current Chemistry, Jan. 1, 1998, pp. 163-208 and 177-180, vol. 198.

Calisher, et al., Antigenic relationships between Flaviviruses as determined by cross-neutralization tests with polyclonal antisera, J. Gen. Virol., 1989, pp. 37-43, vol. 70.

Chang, et al. TLR7/9 antagonist reduces HIV-1-induced immune activation, Retrovirology, 2012, Suppl 2. vol. 172.

Chang, et al., Immune Activation and the Role of TLRs and TLR Agonists in the Pathogenesis of HIV-1 Infection in the Humanized Mouse Model, The Journal of Infectious Diseases, 2013, pp. S145-S149, vol. 208, No. S2.

Chang, et al., TLR-mediated immune activation in HIV, Blood, 2009, pp. 269-270, vol. 113, No. 2.

Charpentier, et al., Persistent low-level HIV-1 RNA between 20 and 50 copies/mL in antiretroviral-treated patients: associated factors and virological outcome, J Antimicrob Chemother, 2012, pp. 2231-2235, vol. 167.

Cillo, et al., Quantification of HIV-1 latency reversal in resting CD4+ T cells from patients on suppressive antiretroviral therapy, PNAS, 2014, pp. 7078-7083, vol. 111, No. 19.

Coiras, HIV-1 Latency and Eradication of Long-term Viral Reservoirs, Retrieved from: http://www.discoverymedicine.com/Mayte-Coiras/2010/030/03/hiv-1-latency-and-eradication on Mar. 13, 2014, 2010, 12 pgs.

Denton, et al., Humanized Mouse Models of HIV Infection, AIDS Rev., 2011, pp. 135-148, vol. 13, No. 3.

Di Bisceglie, et al., The unmet challenges of hepatitis C, Scientific American, Inc., 1999, pp. 80-85.

Dustin, Flying under the radar: The immunbiology of Hepatitis C, Annu. Rev. Immunol., 2007, pp. 71-99, vol. 25.

Dymock, Novel approaches to the treatment of hepatitis C virus infection, Antivirial Chemistry & Chemotherapy, 2000, pp. 79-96, vol. 11.

Dzierba, et al., Dihydropyridopyrazinones and Dihydripterdinones as Corticotropin-Releasing Factor-a receptor antagonists: Structure-Activity Relationships and Computational Modeling, J. Med. Chem., 2007, pp. 5569-5572, vol. 50.

Eriksson, et al., Comparative Analysys of Measures of Viral Reservoirs in HIV-1 Eradication Studies, PLOS Pathogens, 2013, 17 pages, vol. 9, No. 2.

European Patent Office, Examination Report for European Patent Application No. EP107608317, dated Oct. 12, 2015, 4 pages.

European Patent Office, International Preliminary Report on Patentability and Written Opinion for PCT International Application No. PCT/US2015/050039, dated Mar. 21, 2017, 16 pages.

European Patent Office, International Preliminary Report on Patentability and Written Opinion for PCT International Application No. PCT/US2009/041432, dated Oct. 26, 2010, 7 pages.

European Patent Office, International Preliminary Report on Patentability and Written Opinion for PCT International Application No. PCT/US2010/049471, dated Mar. 27, 2012, 7 pages.

European Patent Office, International Preliminary Report on Patentability and Written Opinion for PCT International Application No. PCT/US2015/057932, dated Apr. 15, 2016, 17 pages.

European Patent Office, International Preliminary Report on Patentability and Written Opinion for PCT International Application No. PCT/US2015/057933, dated Jan. 21, 2016, 9 pages.

European Patent Office, International Preliminary Report on Patentability and Written Opinion for PCT International Application No. PCT/US2015/057934, dated Mar. 18, 2016, 20 pages.

European Patent Office, International Preliminary Report on Patentability and Written Opinion for PCT International Application No. PCT/US2008/007955, dated Sep. 15, 2009, 32 pages.

European Patent Office, International Search Report and Written Opinion for PCT International Application No. PCT/US2009/067002, dated Feb. 22, 2010, 10 pages.

European Patent Office, International Search Report and Written Opinion for PCT International Application No. PCT/US2015/050037, dated Dec. 3, 2015, 10 pages.

European Patent Office, International Search Report and Written Opinion for PCT International Application No. PCT/US2015/050039, dated Mar. 4, 2016, 10 pages.

European Patent Office, International Search Report and Written Opinion for PCT International Application No. PCT/US2016/052092, dated Nov. 10, 2016, 11 pages.

European Patent Office, International Search Report and Written Opinion for PCT International Application No. PCT/US2017/028251, dated Nov. 16, 2017, 22 pages.

European Patent Office, International Search Report and Written Opinion for PCT International Application No. PCT/US2018/029974, dated Sep. 18, 2018, 21 pages.

Farumashia, Jun. 2014, p. 575, vol. 50, No. 6 [No English copy available].

Gibson, Pharmaceutical Preformulation and Formulation, 2009, pp. 334-335.

Gluck, et al., New technology platforms in the development of vaccines for the future, 2002, B10-6, vol. 5.

Goodchild, et al., Primary leukocyte screens for innate immune agonists, Journal of Biomolecular Screening, 2009, pp. 723-730, vol. 14.

(56) References Cited

OTHER PUBLICATIONS

Gordon, et al., Control of hepatitis C: A medicinal chemistry perspective, Journal of Medicinal Chemistry, 2005, pp. 1-20, vol. 48.

Guillory, Generation of Polymorphs, Hydrates, Solvates, and Amorphous Solids, Polymorphism in Pharmaceutical Solids, 1999, pp. 184-227.

Gunthard, et al., Residual Human Immunodeficiency Virus (HIV) Type 1 RNA and DNA in Lymph Nodes and HIV RNA in Genital Secretions and in Cerebrospinal Fluid after Suppression of Viremia for 2 Years, The Journal of Infectious Diseases, 2001, pp. 1318-1327, vol. 183.

Horowitz, et al., HIV-1 suppression and durable control by combining single broadly neutralizing antibodies and antiretroviral drugs in humanized mice, PNAS USA, 2013, pp. 16538-16543.

Horsmans, et al., Isatoribine, an agonist of TLR7, reduces plasma virus concentration in chronic hepatitis C infection, Hepatology, 2005, pp. 724-731, vol. 42.

Hubert, et al., Natural history of serum HIV-1 RNA levels in 330 patients with a known date of infection, AIDS, 2000, pp. 123-131, vol. 14.

Illan-Cabeza, et al., Antiproliferatvie effects of palladium(II) complexes of 5-nitrosopyrimidines and interactions with the proteolytic regulatory enzymes of the renin-angiotensin system in tumoral brain cells, J. Inorg. Biochem., 2013, pp. 118-127, vol. 126.

Isobe, et al., Synthesis and biological evaluation of novel-9-substituted-8-hydroxyadenine derivatives as potent interferon inducers, Journal of Medicinal Chemistry, 2006, pp. 2088-2095, vol. 49, No. 6.

Jiang, et al.,Targeting NF-KB Signaling with Protein Kinase C Agonists As an Emerging Strategy for Combating HIV Latency, AIDS Research and Human Retroviruses, 2015, vol. 31, No. 1.

Jin, et al., Synthesis and Immunostimulatory activity of 8-substituted amino 9-benzyladenines as potent Toll-like receptor 7 agonists, Bioorg. Med. Chem. Lett, 2006, pp. 4559-4563, vol. 16.

Julien, et al., Broadly Neutralizing Antibody PGT121 Allosterically Modulates CD4 Binding via Recognition of the HIV-gp120 V3 Base and Multiple Surrounding Glycans, PLOS Pathogens, 2013, 15 pages, vol. 9, No. 5.

Juricova, et al., Synthesis of Base-Modified 'Abbreviated' NAD Analogues, Collection of Czechoslovak Chemical Communications, 1995, pp. 237-250, vol. 60, No. 2.

Kelly, Journal of Medicinal Chemistry, 1989, pp. 1757-1763, vol. 32, No. 8.

Korba, et al., Treatment of chronic woodchuck hepatitis virus infection in the Eastern Wookdchuck (*Marnota monax*) with nucleoside analgoues is predictive of therapy for chronic hepatitis B virus infection in humans, Hepatology, 2000, pp. 1165-1175, vol. 31.

Kwong, et al., Human Antibodies that Neutralize HIV-1: Identification, Structures, and B Cell Ontogenies, Immunity, 2012, pp. 412-425, vol. 37.

Lanford, et al., GS-9620, an Oral Agonist of Toll-Like Receptor-7, Induces Prolonged Suppression of Hepatitis B Virus in Chronically Infected Chimpanzees, Gastroenterology, 2013, pp. 1508-1517, vol. 144.

Lee, et al., Activation of anti-hepatitis C virus responses via Toll-like receptor 7, 2006, Proc. Natl. Acad. Sci., pp. 1828-1833, vol. 103.

Lewin, et al., HIV Rebound Prevented in Monkeys, Nature, Nov. 15, 2018, pp. 333-334, vol. 563.

Loveday, Prediction of progression to AIDS with serum HIV-1 RNA and CD4 count, The Lancet, 1995, pp. 790-791, vol. 345.

Malbec, et al., Broadly neutralizing antibodies that inhibit HIV-1 cell to cell transmission, Journal of Experimental Medicine, 2013, pp. 2813-2821, vol. 210, No. 13.

Marsden, et al., Neutralizing the HIV Reservoir, Cell, 2014, pp. 971-972, vol. 158.

Matsuoka, Kesshotake no Kiso to Oyo [Fundamentals and application of crystalline polymorphs], CMC Publishing Co., Ltd, Oct. 22, 2010, popular edition, First print, pp. 105-117 and 181-191.

Menne, et al., The woodchuck as an animal model for pathogenesis and therapy of chronic hepatitis B virus infection, World J. Gastroenterol, 2007, pp. 104-124, vol. 13.

Meyer, Clinical Investigations of Toll-Like Receptor Agonists, Jul. 2008, pp. 1051-1065, vol. 17, No. 7.

Moennig, et al., The pestiviruses, Advances in Virus Research, 1992, pp. 53-98, vol. 41.

Mofenson, et al., The Relationship between Serum Human Immunodeficiency Virus Type 1 (HIV-1) RNA Level, CD4 Lymphocyte Percent, and Long-Term Mortality Risk in HIV-1-Infected Children, The Journal of Infectious Diseases, 1997, pp. 1029-1038, vol. 175.

Moody, et al., TLR-7/8 and 9 Agonists Cooperate to Enthance HIV-1 Envelope Antibody Responses in Rhesus Macaques, J. Virol., 2014, 42 pages.

Moradpour, et al., Replication of hepatitisc C virus, Nature Reviews, Microbiology, 2007, pp. 453-463, vol. 5.

Moye, et al., The synthesis of 4,6-Dihydroxy-2-methoxypyrimidine and derived pyrimidine intermediates, Aust. J. Chem., 1965, pp. 1309-1310, vol. 17.

Nagashima, et al., Solution-Phase parallel synthesis of a N-Alkylated dihydropteridinone library from fluorous-amino acids, J. Comb. Chem., 2004, pp. 942-949, vol. 6.

Ostrowski, et al., Residual Virae,ia in HIV-1-Infected Patients with Plasma Viral Load £20 copies/ml is Associated with Increased Blood Levels of Soluble Immune Activation Markers, Scandinavian Journal of Immunology, 2008, pp. 652-660, vol. 68.

Persaud, a stable latent reservoir for HIV-1 in resting CD4+ T lymphocytes in infected children, The Journal of Clinical Investigation, 2000, pp. 995-1003, vol. 105, No. 7.

Picker, et al., Antibodies advance the search for a cure, Nature, 2013, pp. 207-208, vol. 503.

Prince, et al., Common Antiviral Agents, 2014, 9 pages.

Rasmussen, Eliminating the latent HIV reservoir by reactivation strategies, Human Vaccines & Immunotherapeutics, 2013, pp. 790-799, vol. 9, No. 4.

Roethle, et al., Identification and Optimization of Pteridinone Toll-like Receptor 7 (TLR7) Agonists for the Oral Treatment of Viral Hepatitis, Journal of Medicinal Chemistry, 2013, pp. 7324-7333, vol. 56, No. 18.

Scott, et al., Interferon-alpha-2b plus ribavirin: a review of its use in the management of chronic hepatistis C, Drugs, 2002, pp. 507-556, vol. 62.

Shingai, et al., Antibody-mediated immunotherapy of macaques chronically infected with SHIV suppresses viraemia, Nature, 2013, pp. 277-291, vol. 503.

Siliciano, et al., HIV Latency, Cold Spring Harb Perspect Med, 2011, 20 pages.

Smith et al., Developments in HIV-1 Immunotherapy and therapeutic vaccination, F1000Pripe Reports, 2014, vol. 6, No. 43.

Stahly, Diversity in Single-and Multiple-Component Crystals. The Search for and Prevalence of Polymorphs and Cocrystals, Crystal Growth & Design, 2007, pp. 1007-1026, vol. 7.

Sun, et al., Functional characterization of ex vivo blood myeloid and plasmacytoid dendritic cells after infection with dengue virus, Virology, 2009, pp. 207-215, vol. 383.

Susvilo, et al., Study on the reaction of methy N-Methyl-N-(6-substituted-5-nitropyrimidine-4-yl) glycinates with sodium alkoxides, J. Heterocyclic Chem., 2006, pp. 267-276, vol. 43.

Tennant, Animal models of hepatitis B virus infection, Clinics in Liver Disease, 1999, pp. 241-266, vol. 3.

Thomas, et al., Investigating toll-like receptor agonists for potential to treat hepatitis C virus infection, Antimicrobial Agents and Chemotherapy, 2007, pp. 2969-2978, vol. 51.

Van Der Sluis, et al, Dendritic Cell-induced Activation of Latent HIV-1 Provirus in Actively Proliferating Primary T Lymphocytes, PLOS Pathogens, 2013, 15 pages, vol. 9, No. 3.

Walker, et al., Broad neutralization coverage of HIV by multiple highly potent antibodies, Nature, 2011, pp. 466-471, vol. 477.

Whitney, Rapid seeding of the viral reservoir prior to SIV viraemia in rhesus monkeys, Nature, 2014, pp. 74-77, vol. 512.

XRPD PEAK LIST OF FORM I

| PEAK POSITION [02-THETA] | RELATIVE INTENSITY [%] |
|---|---|
| 5.83 | 100.0 |
| 11.42 | 26.2 |
| 11.55 | 37.9 |
| 17.74 | 10.0 |
| 20.09 | 7.7 |
| 20.92 | 4.9 |
| 22.28 | 16.3 |
| 23.87 | 14.6 |
| 26.01 | 11.9 |
| 26.79 | 7.8 |

*FIGURE 2*

XRPD PEAK LIST OF FORM II

| PEAK POSITION [°2-THETA] | RELATIVE INTENSITY [%] |
|---|---|
| 4.63 | 100.0 |
| 9.17 | 34.5 |
| 15.76 | 23.9 |
| 17.77 | 25.7 |
| 18.32 | 58.2 |
| 19.17 | 20.8 |
| 19.93 | 58.7 |
| 22.42 | 51.3 |
| 25.53 | 65.5 |
| 29.05 | 27.0 |

*FIGURE 6*

XRPD PEAK LIST OF FORM III

| PEAK POSITION [02-THETA] | RELATIVE INTENSITY [%] |
|---|---|
| 5.04 | 100.0 |
| 10.10 | 11.1 |
| 15.18 | 6.4 |
| 16.88 | 10.0 |
| 20.29 | 11.0 |
| 21.47 | 17.6 |
| 21.95 | 21.4 |
| 23.93 | 12.3 |
| 25.23 | 12.6 |
| 29.44 | 5.4 |

*FIGURE 10*

XRPD PEAK LIST OF FORM IV

| PEAK POSITION [02-THETA] | RELATIVE INTENSITY [%] |
|---|---|
| 4.14 | 100.0 |
| 8.78 | 9.3 |
| 16.77 | 8.5 |
| 18.14 | 12.4 |
| 18.74 | 10.3 |
| 19.74 | 8.2 |
| 21.08 | 9.1 |
| 21.41 | 8.3 |
| 23.80 | 16.0 |
| 26.64 | 11.9 |

*FIGURE 14*

XRPD PEAK LIST OF FORM IX

| POS. [°2TH.] | REL. INT. [%] |
|---|---|
| 5.3 | 100.0 |
| 9.8 | 92.8 |
| 15.6 | 92.7 |
| 13.1 | 76.6 |
| 17.0 | 44.3 |
| 21.9 | 42.7 |
| 20.0 | 33.4 |
| 20.7 | 29.1 |
| 24.9 | 26.8 |
| 19.6 | 25.2 |

*FIGURE 21*

XRPD PEAK LIST OF FORM X

| POS. [02TH.] | REL. INT. [%] |
|---|---|
| 5.5 | 100.0 |
| 16.0 | 77.1 |
| 10.8 | 70.5 |
| 19.0 | 69.4 |
| 12.9 | 62.4 |
| 9.4 | 56.5 |
| 14.4 | 52.0 |
| 23.9 | 49.8 |
| 21.9 | 47.7 |
| 11.9 | 39.5 |

FIGURE 24

XRPD PEAK LIST OF FORM XI

| POS. [02TH.] | REL. INT. [%] |
|---|---|
| 7.7 | 100.0 |
| 17.1 | 77.2 |
| 19.5 | 68.0 |
| 17.8 | 42.9 |
| 19.3 | 35.8 |
| 10.7 | 35.6 |
| 23.0 | 28.6 |
| 8.4 | 28.3 |
| 23.9 | 26.1 |
| 21.4 | 25.7 |

FIGURE 27

XRPD PEAK LIST OF FORM XII

| POS. [02TH.] | REL. INT. [%] |
|---|---|
| 20.3 | 100.0 |
| 21.9 | 71.6 |
| 21.1 | 56.5 |
| 18.7 | 55.5 |
| 9.0 | 55.4 |
| 25.8 | 49.2 |
| 17.1 | 44.8 |
| 10.9 | 39.1 |
| 13.7 | 37.6 |
| 6.0 | 35.9 |

*FIGURE 29*

| XRPD PEAK LIST OF FORM XIII | |
|---|---|
| POS. [°2TH.] | REL. INT. [%] |
| 4.6 | 100.0 |
| 18.4 | 8.9 |
| 9.2 | 5.1 |
| 20.0 | 2.8 |
| 13.8 | 1.8 |
| 15.8 | 1.6 |
| 8.9 | 1.5 |
| 26.9 | 1.4 |
| 23.1 | 1.3 |
| 16.0 | 1.3 |

FIGURE 32

XRPD PEAK LIST OF FORM XIV

| POS. [02TH.] | REL. INT. [%] |
|---|---|
| 9.5 | 100.0 |
| 24.6 | 50.6 |
| 14.3 | 44.9 |
| 7.1 | 35.9 |
| 16.8 | 33.7 |
| 17.6 | 27.7 |
| 22.0 | 26.4 |
| 26.2 | 22.6 |
| 24.9 | 22.2 |
| 10.6 | 21.1 |

*FIGURE 34*

SOLID FORMS OF A TOLL-LIKE RECEPTOR MODULATOR

CROSS-REFERENCES TO RELATED APPLICATIONS

This application is a Continuation of U.S. patent application Ser. No. 15/591,711, filed on May 10, 2017, which is a Continuation of U.S. patent application Ser. No. 14/853,855, filed on Sep. 14, 2015, now U.S. Pat. No. 9,738,646, issued on Aug. 22, 2017, which claims priority to U.S. Provisional Application No. 62/051,063, filed Sep. 16, 2014, which is incorporated in its entirety herein for all purposes.

BACKGROUND

The present disclosure relates generally to crystalline solid forms of the antiviral compound 4-amino-2-butoxy-8-(3-(pyrrolidin-1-ylmethyl)benzyl)-7,8-dihydropteridin-6(5H)-one, processes for making the forms, and their therapeutic methods of use.

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. One family of these receptors is known as Toll-like receptors (TLRs), due to their homology with receptors that were first identified and named in *Drosophila*, and are present in cells such as macrophages, dendritic cells, and epithelial cells.

There are at least ten different TLRs in mammals. Ligands and corresponding signaling cascades have been identified for some of these receptors. For example, TLR2 is activated by the lipoprotein of bacteria (e.g., *E. coli.*), TLR3 is activated by double-stranded RNA, TLR4 is activated by lipopolysaccharide (i.e., LPS or endotoxin) of Gram-negative bacteria (e.g., *Salmonella* and *E. coli* O157:H7), TLR5 is activated by flagellin of motile bacteria (e.g., *Listeria*), TLR7 recognizes and responds to imiquimod and TLR9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-α), interleukin-1 (IL-1), and certain chemokines. Agonists of TLR-7 are immunostimulants and induce the production of endogenous interferon-α in vivo.

There are a number of diseases, disorders, and conditions linked to TLRs such that therapies using a TLR agonist are believed promising, including but not limited to melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, and viral infections such as HBV, Flaviviridae viruses, HCV, HPV, RSV, SARS, HIV, or influenza.

The treatment of Flaviviridae virus infections with TLR agonists is particularly promising. Viruses of the Flaviviridae family comprise at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis encephalitis, Omsk hemorrhagic fever virus and Zika virus. Combined, infections from the Flaviviridae virus family cause significant mortality, morbidity and economic losses throughout the world. Therefore, there is a need to develop effective treatments for Flaviviridae virus infections.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., *J. Med. Chem.* 2005, 48, 1-20; Maradpour, D.; et al., *Nat. Rev. Micro.* 2007, 5(6), 453-463). A number of HCV treatments are reviewed by Bymock et al. in Antiviral Chemistry & Chemotherapy, 11:2; 79-95 (2000). Currently, there are several antiviral compounds, ribavirin, a nucleoside analog, interferon-alpha (α) (IFN), and sofosbuvir, another nucleoside analog, that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. *Drugs* 2002, 62, 507-556) but less than half the patients given this treatment show a persistent benefit.

HCV is recognized by innate virus-sensing mechanisms that induce a rapid IFN response (Dustin, et al., *Annu. Rev. Immunol.* 2007, 25, 71-99). It is likely that the sources of the IFN are, at least, the infected hepatocytes and particularly the plasmacytoid dendritic cells (pDC) that highly express TLR 7 receptors and secrete high amounts of IFN. Horsmans, et al. (*Hepatology*, 2005, 42, 724-731), demonstrated that a once daily 7-day treatment with the TLR 7 agonist isatoribine reduces plasma virus concentrations in HCV infected patients. Lee, et al. (*Proc. Natl. Acad. Sci. USA*, 2006, 103, 1828-1833), demonstrated that TLR 7 stimulation can induce HCV immunity by both an IFN and IFN-independent mechanisms. These workers also revealed that TLR 7 is expressed in normal as well as HCV infected hepatocytes. These combined results support the conclusion that stimulation of TLR 7 receptors, such as through the administration of a TLR 7 agonist, is a viable mechanism for effectively treating natural HCV infections. Given the need for more effective treatments for HCV infections, there is a need to develop safe and therapeutically effective TLR 7 agonists.

Similarly, despite the existence of efficient vaccines, hepatitis B virus (HBV) infection remains a major public health problem worldwide with 400 million chronic carriers. These infected patients are exposed to a risk of developing liver cirrhosis and hepatocellular carcinoma (Lee, W. M. 1997, N. Eng. J. Med., 337, 1733-1745). Currently, there are believed to be approximately 1.25 million chronic hepatitis B carriers just in the United States, with 200,000 people newly infected each year by contact with blood or body fluids.

Hepatitis B virus is second to tobacco as a cause of human cancer. The mechanism by which HBV induces cancer is unknown, although it is postulated that may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is in fact very similar to that of HIV, which accounts for why HBV infection is common among patients with AIDS or HIV-associated infections. However, HBV is more contagious than HIV. To ameliorate suffering and to prolong the lives of infected hosts new compounds and methods of treating AIDS and attacking the HIV virus continue to be sought.

The compound 4-amino-2-butoxy-8-(3-(pyrrolidin-1-yl-methyl)benzyl)-7,8-dihydropteridin-6(5H)-one, designated herein as Compound I, as described for example in WO 2010/077613 and U.S. Pat. No. 8,367,670, has been reported to be an inhibitor of toll-like receptor 7. Moreover, Compound I is being investigated for use in treating HBV and HIV. However, Compound I was not previously known in any crystalline form.

BRIEF SUMMARY OF THE INVENTION

In some embodiments, the present invention provides a crystalline form of Compound I having the structure:

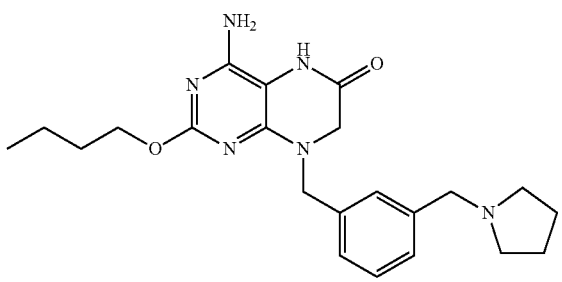 [SMILES: CCCCOc1nc(N)c2c(n1)N(Cc1cccc(CN3CCCC3)c1)CC(=O)N2]

and solvates or hydrates thereof.

In some embodiments, the present invention provides a crystalline Form I of Compound I, and solvates or hydrates thereof, characterized by an X-ray powder diffraction (XRPD) pattern comprising three or more peaks at 5.8, 11.4, 11.6, 17.7, 22.3, 23.9, or 26.0 degrees 2θ (±0.2 degrees 2θ), wherein the XRPD is made using CuK$_{\alpha1}$ radiation.

In some embodiments, the present invention provides a crystalline Form II of Compound I, and solvates or hydrates thereof, characterized by an X-ray powder diffraction (XRPD) pattern comprising three or more peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{\alpha1}$ radiation.

In some embodiments, the present invention provides a crystalline Form III of Compound I, and solvates or hydrates thereof, characterized by an X-ray powder diffraction (XRPD) pattern having three or more peaks at 5.0, 10.1, 16.9, 20.3, 21.5, 22.0, 23.9, or 25.2 degrees 2θ (±0.2 degrees 2θ), wherein the XRPD is made using CuK$_{\alpha1}$ radiation.

In some embodiments, the present invention provides a crystalline Form IV of Compound I, and solvates or hydrates thereof, characterized by an X-ray powder diffraction (XRPD) pattern having peaks at 4.1, 18.1, 18.7, 23.8, and 26.6 degrees 2θ (±0.2 degrees 2θ), wherein the XRPD is made using CuK$_{\alpha1}$ radiation.

In some embodiments, the present invention provides a crystalline Form IX of Compound I, and solvates or hydrates thereof, characterized by an X-ray powder diffraction (XRPD) pattern having three or more peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha1}$ radiation.

In some embodiments, the present invention provides a crystalline Form X of Compound I, and solvates or hydrates thereof, characterized by an X-ray powder diffraction (XRPD) pattern having three or more peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{\alpha1}$ radiation.

In some embodiments, the present invention provides a method of preparing a crystalline Form I of Compound I by forming a mixture of Compound I, and a solvent including a $C_1$-$C_3$ alcohol and dichloromethane, under conditions suitable to prepare Form I.

In some embodiments, the present invention provides a method of preparing a crystalline Form II of Compound I by forming a mixture of Compound I and chloroform, under conditions suitable to prepare Form II.

In some embodiments, the present invention provides a method of preparing a crystalline Form III of Compound I by heating a Form I of Compound I to a temperature of from about 130° C. to about 190° C., thereby forming Form III.

In some embodiments, the present invention provides a method of preparing a crystalline Form IV of Compound I by heating a Form II of Compound I to a temperature of from about 90° C. to about 250° C., thereby forming Form IV.

In some embodiments, the present invention provides a method of preparing a crystalline Form IX of Compound I by forming a mixture comprising a Form I of Compound I, water and trifluoroethanol, under conditions suitable to prepare Form IX.

In some embodiments, the present invention provides a method of preparing a crystalline Form X of Compound I by forming a mixture comprising a Form I of Compound I and chloroform, under conditions suitable to prepare Form X.

BRIEF DESCRIPTION OF THE DRAWINGS

FIG. 2 shows a table of X-ray powder diffraction peaks of Compound I Form I.

FIG. 6 shows a table of X-ray powder diffraction peaks of Compound I Form II.

FIG. 10 shows a table of X-ray powder diffraction peaks of Compound I Form III.

FIG. 14 shows a table of X-ray powder diffraction peaks of Compound I Form IV.

FIG. 21 shows a table of X-ray powder diffraction peaks of Compound I Form IX.

FIG. 24 shows a table of X-ray powder diffraction peaks of Compound I Form X.

FIG. 27 shows a table of X-ray powder diffraction peaks of Compound I Form XI.

FIG. 29 shows a table of X-ray powder diffraction peaks of Compound I Form XII.

FIG. 32 shows a table of X-ray powder diffraction peaks of Compound I Form XIII.

FIG. 34 shows a table of X-ray powder diffraction peaks of Compound I Form XIV.

DETAILED DESCRIPTION OF THE INVENTION

I. General

Figure 1:
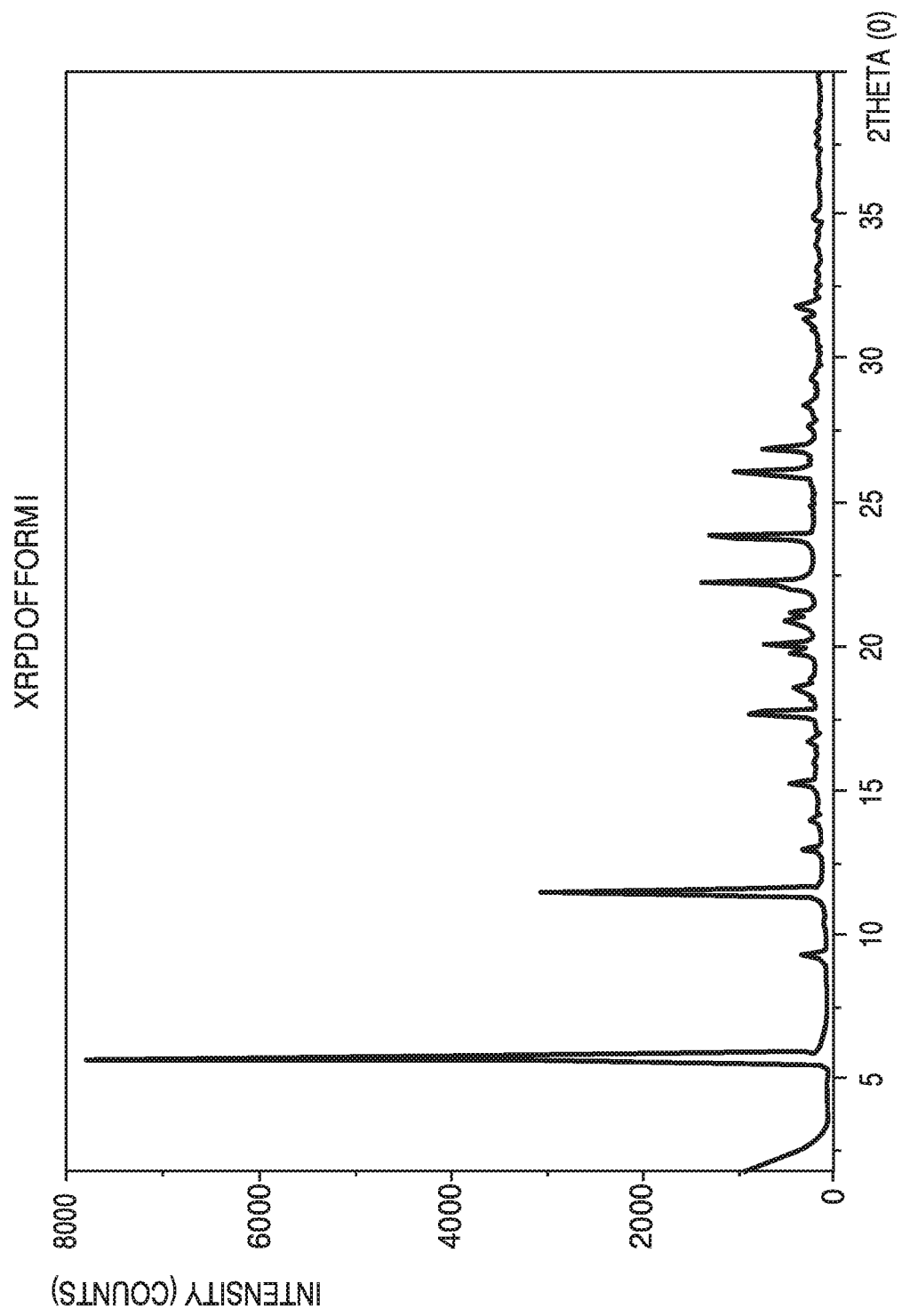
FIG. 1 shows an X-ray powder diffraction pattern of Compound I Form I.

The compound 4-amino-2-butoxy-8-(3-(pyrrolidin-1-yl-methyl)benzyl)-7,8-dihydropteridin-6(5H)-one (Compound I) is a selective and potent inhibitor of toll-like receptor 7 (TLR-7):

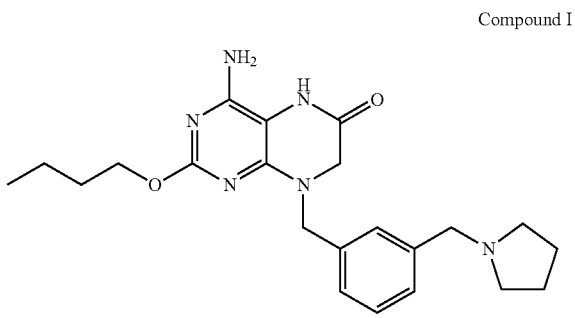 [SMILES: CCCCOc1nc(N)c2c(n1)N(Cc1cccc(CN3CCCC3)c1)CC(=O)N2]

Compound I

The present invention results from the surprising discoveries of the solid forms of Compound I, advantages attributed to the forms as described herein, and processes for making the solid forms. Crystalline materials are generally more stable physically and chemically. The superior stability of crystalline material may make them more suitable to be used in the final dosage form as shelf life of the product is directly correlated with stability. A crystallization step in API processing also means an opportunity to upgrade the drug substance purity by rejecting the impurities to the processing solvent.

II. Definitions

As used in the present specification, the following words and phrases are generally intended to have the meanings as set forth below, except to the extent that the context in which they are used indicates otherwise.

"Hydrate" refers to a complex formed by the combining of Compound I and water.

The term includes stoichiometric as well as non-stoichiometric hydrates.

"Solvate" refers to a complex formed by the combining of Compound I and a solvent.

"Desolvated" refers to a Compound I form that is a solvate as described herein, and from which solvent molecules have been partially or completely removed. Desolvation techniques to produce desolvated forms include, without limitation, exposure of a Compound I Form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

"Alcohol" refers to a solvent having a hydroxy group. Representative alcohols can have any suitable number of carbon atoms, such as $C_1$-$C_6$, and any suitable number of hydroxy groups, such as 1-3. Exemplary alcohols include, but are not limited to, methanol, ethanol, n-propanol, i-propanol, etc.

"Therapeutically effective amount" refers to an amount that is sufficient to effect treatment, as defined below, when administered to a mammal in need of such treatment. The therapeutically effective amount will vary depending upon the subject being treated, the weight and age of the subject, the severity of the disease condition, the manner of administration and the like, which can readily be determined by one of ordinary skill in the art.

"Substantially free of other crystalline forms of Compound I" refers to a crystalline form of Compound I that contains less than 10% of other crystalline forms of Compound I. For example, substantially free can refer to a crystalline form of Compound I that contains less than 9, 8, 7, 6, 5, 4, 3, 2, or 1% of other crystalline forms of Compound I. Preferably, substantially free refers to a crystalline form of Compound I that contains less than 5% of other crystalline forms of Compound I. Preferably, substantially free refers to a crystalline form of Compound I that contains less than 1% of other crystalline forms of Compound I.

III. Solid Forms of Compound I

The present invention provides solid forms of 4-amino-2-butoxy-8-(3-(pyrrolidin-1-ylmethyl)benzyl)-7,8-dihydropteridin-6(5H)-one (Compound I; see U.S. Pat. Nos. 8,367,670 and 8,809,527), including crystalline and amorphous forms, as well as solvate and hydrate forms. In some embodiments, the present invention provides a crystalline form of Compound I having the structure:

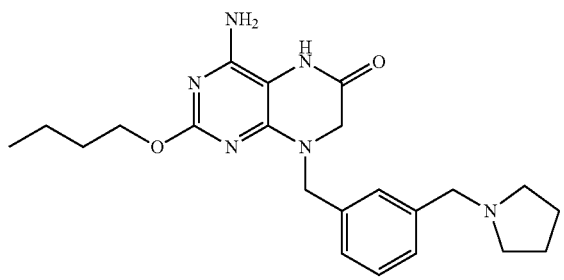 [SMILES: CCCCOc1nc(N)c2c(n1)N(Cc1cccc(CN3CCCC3)c1)CC(=O)N2]

and solvates or hydrates thereof.

Compound I can adopt a variety of solid forms, including, but not limited to, Form I, Form II, Form III, and Form IV. Other forms include Form V, Form VI, Form VII, Form VIII, Form IX, Form X, Form XI, Form XII, Form XIII and Form XIV. Compound I can form a mixture of two or more crystalline forms, or form a single crystalline form substantially free of other crystalline forms.

Form I

In some embodiments, crystalline Form I of Compound I can be characterized by an X-ray powder diffraction pattern having peaks at 5.8, 11.4, 11.6, 17.7, 20.1, 20.9, 22.3, 23.9, 26.0 and 26.8 degrees 2θ (±0.2 degrees 2θ), wherein the XRPD is made using $CuK_{\alpha 1}$ radiation, and a differential scanning calorimetry (DSC) plot having endotherms at about 133° C., 170° C. and 273° C.

Form I of Compound I can be characterized by an X-ray powder diffraction (XRPD) pattern having at least three, four, five, or more, peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation. In some embodiments, the crystalline Form I of Compound I can be characterized by an X-ray powder diffraction pattern having at least three peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation. In some embodiments, the crystalline Form I of Compound I can be characterized by an X-ray powder diffraction pattern having at least four peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation. In some embodiments, the crystalline Form I of Compound I can be characterized by an XRPD pattern having at least five peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation.

Form I of Compound I can also be characterized by an X-ray powder diffraction (XRPD) pattern having at least six, seven, eight, nine or more, peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation. In some embodiments, the crystalline Form I of Compound I can be characterized by an X-ray powder diffraction pattern having at least six peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation. In some embodiments, the crystalline Form I of Compound I can be characterized by an X-ray powder diffraction pattern having at least seven peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation. In some embodiments, the crystalline Form I of Compound I can be characterized by an XRPD pattern having at least eight peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation. In some embodiments, the crystalline Form I of Compound I can be characterized by an X-ray powder diffraction pattern having at least nine peaks at 5.8, 11.4, 11.6, 17.7, 20.1, 20.9, 22.3, 23.9, 26.0 or 26.8 degrees 2θ (±0.2 degrees 2θ), wherein the XRPD is made using $CuK_{\alpha 1}$ radiation.

In some embodiments, the crystalline Form I of Compound I can be characterized by an X-ray powder diffraction (XRPD) pattern having three or more peaks at 5.8, 11.4, 11.6, 17.7, 22.3, 23.9 or 26.0 degrees 2θ (±0.2 degrees 2θ), wherein the XRPD is made using $CuK_{\alpha 1}$ radiation. In some embodiments, the crystalline Form I of Compound I can be characterized by an XRPD pattern having peaks at 5.8, 11.4, and 11.6 degrees 2θ (±0.2 degrees 2θ), wherein the XRPD is made using $CuK_{\alpha 1}$ radiation. In some embodiments, the crystalline Form I of Compound I can be characterized by an X-ray powder diffraction (XRPD) pattern further comprising one or more peaks at 17.7, 22.3, 23.9 or 26.0 degrees 2θ (±0.2 degrees 2θ), wherein the XRPD is made using $CuK_{\alpha 1}$ radiation. In some embodiments, the crystalline Form I of Compound I can be characterized by an X-ray powder diffraction (XRPD) pattern further comprising two or more peaks at 17.7, 22.3, 23.9 or 26.0 degrees 2θ (±0.2 degrees 2θ), wherein the XRPD is made using $CuK_{\alpha 1}$ radiation. In some embodiments, the crystalline Form I of Compound I can be characterized by an X-ray powder diffraction (XRPD) pattern further comprising three or more peaks at 17.7, 22.3, 23.9 or 26.0 degrees 2θ (±0.2 degrees 2θ), wherein the XRPD is made using $CuK_{\alpha 1}$ radiation.

In some embodiments, the crystalline Form I of Compound I can be characterized by an XRPD pattern having peaks at 5.8, 11.6, 22.3, and 23.9 degrees 2θ (±0.2 degrees 2θ), wherein the XRPD is made using CuK$_{α1}$ radiation. In some embodiments, the crystalline Form I of Compound I can be characterized by an XRPD pattern having peaks at 5.8, 11.6, 17.7, 22.3, 23.9, 26.0 and 26.8 degrees 2θ (±0.2 degrees 2θ), wherein the XRPD is made using CuK$_{α1}$ radiation. In some embodiments, the crystalline Form I of Compound I can be characterized by an XRPD pattern having peaks at 17.7, 20.1, 20.9, 22.3, 23.9, 26.0 and 26.8 degrees 2θ (±0.2 degrees 2θ), wherein the XRPD is made using CuK$_{α1}$ radiation.

In some embodiments, the crystalline Form I of Compound I can be characterized by an XRPD pattern having peaks at 5.8, 11.4, 11.6, 17.7, 20.1, 20.9, 22.3, 23.9, 26.0 and 26.8 degrees 2θ (±0.2 degrees 2θ), wherein the XRPD is made using CuK$_{α1}$ radiation. In some embodiments, the crystalline Form I of Compound I can be characterized by the XRPD pattern substantially in accordance with that of FIG. 1. In some embodiments, the crystalline Form I of Compound I can be substantially free of other crystalline forms of Compound I. In some embodiments, the crystalline Form I of Compound I can be substantially free of Form II, Form III and Form IV. In some embodiments, the crystalline Form I of Compound I can also be substantially free of Form V, Form VI, Form VII, Form VIII, Form IX, Form X, Form XI, Form XII, Form XIII and Form XIV.

Form I of Compound I can be characterized by a differential scanning calorimetry (DSC) plot having at least one or more endotherms at about 133° C., about 170° C., or about 273° C. In some embodiments, the crystalline Form I of Compound I can be characterized by one or more differential scanning calorimetry (DSC) endotherms at about 133, 170, or about 273° C. In some embodiments, the crystalline Form I of Compound I can be characterized by one or more differential scanning calorimetry (DSC) endotherms at about 133° C. or about 170° C. In some embodiments, the crystalline Form I of Compound I can be characterized by DSC endotherms at about 133° C. and about 170° C. In some embodiments, the crystalline Form I of Compound I can be characterized by one or more differential scanning calorimetry (DSC) endotherms at about 133, 170, and about 273° C.

In some embodiments, the crystalline Form I of Compound I can be characterized by an XRPD pattern having peaks at 5.8, 11.4, 11.6, 17.7, 20.1, 20.9, 22.3, 23.9, 26.0 and 26.8 degrees 2θ (±0.2 degrees 2θ), wherein the XRPD is made using CuK$_{α1}$ radiation, and one or more DSC endotherms at about 133° C. and about 170° C.

Form II

Form II of Compound I can be characterized by an XRPD pattern having at least three, four, five, or more, peaks 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation. In some embodiments, the crystalline Form II of Compound I can be characterized by an XRPD pattern having at least three peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation. In some embodiments, the crystalline Form II of Compound I can be characterized by an XRPD pattern having at least four peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation. In some embodiments, the crystalline Form II of Compound I can be characterized by an XRPD pattern having at least five peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation.

Form II of Compound I can also be characterized by an XRPD pattern having at least six, seven, eight, nine, or more, peaks 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation. In some embodiments, the crystalline Form II of Compound I can be characterized by an XRPD pattern having at least six peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation. In some embodiments, the crystalline Form II of Compound I can be characterized by an XRPD pattern having at least seven peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation. In some embodiments, the crystalline Form II of Compound I can be characterized by an XRPD pattern having at least eight peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation. In some embodiments, the crystalline Form II of Compound I can be characterized by an XRPD pattern having at least nine peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation.

In some embodiments, the crystalline Form II of Compound I can be characterized by an X-ray powder diffraction (XRPD) pattern having three or more peaks at 4.6, 9.2, 15.8, 17.8, 18.3, 19.2, 19.9, 22.4, 25.5 or 29.1 degrees 2θ (±0.2 degrees 2θ), wherein the XRPD is made using CuK$_{α1}$ radiation. In some embodiments, the crystalline Form II of Compound I can be characterized by an XRPD pattern having peaks at 4.6, 18.3, 19.9, 22.4 and 25.5 degrees 2θ (±0.2 degrees 2θ), wherein the XRPD is made using CuK$_{α1}$ radiation. In some embodiments, the crystalline Form II of Compound I can be characterized by an X-ray powder diffraction (XRPD) pattern further comprising one or more peaks at 9.2, 15.8, 17.8, 19.2, or 29.1 degrees 2θ (±0.2 degrees 2θ), wherein the XRPD is made using CuK$_{α1}$ radiation. In some embodiments, the crystalline Form II of Compound I can be characterized by an X-ray powder diffraction (XRPD) pattern further comprising two or more peaks at 9.2, 15.8, 17.8, 19.2, or 29.1 degrees 2θ (±0.2 degrees 2θ), wherein the XRPD is made using CuK$_{α1}$ radiation. In some embodiments, the crystalline Form II of Compound I can be characterized by an X-ray powder diffraction (XRPD) pattern further comprising three or more peaks at 9.2, 15.8, 17.8, 19.2, or 29.1 degrees 2θ (±0.2 degrees 2θ), wherein the XRPD is made using CuK$_{α1}$ radiation. In some embodiments, the crystalline Form II of Compound I can be characterized by an X-ray powder diffraction (XRPD) pattern further comprising four or more peaks at 9.2, 15.8, 17.8, 19.2, or 29.1 degrees 2θ (±0.2 degrees 2θ), wherein the XRPD is made using CuK$_{α1}$ radiation.

In some embodiments, the crystalline Form II of Compound I can be characterized by an XRPD pattern having peaks at 4.6, 9.2, 15.8, 17.8, 18.3, 19.2, 19.9, 22.4, 25.5 and 29.1 degrees 2θ (±0.2 degrees 2θ), wherein the XRPD is made using CuK$_{α1}$ radiation. In some embodiments, the crystalline Form II of Compound I can be characterized by the XRPD pattern substantially in accordance with that of FIG. 5. In some embodiments, the crystalline Form II of Compound I can be substantially free of other crystalline forms of Compound I. In some embodiments, the crystalline Form II of Compound I can be substantially free of Form I, Form III and Form IV. In some embodiments, the crystalline Form II of Compound I can also be substantially free of Form V, Form VI, Form VII, Form VIII, Form IX, Form X, Form XI, Form XII, Form XIII and Form XIV.

Form II of Compound I can be characterized by a differential scanning calorimetry (DSC) plot having at least one or more endotherms at about 98, about 253° C., or about 273° C. In some embodiments, the crystalline Form II of Compound I can be characterized by one or more differential scanning calorimetry (DSC) endotherms at about 98, 253, or about 273° C. In some embodiments, the crystalline Form II of Compound I can be characterized by one or more differential scanning calorimetry (DSC) endotherms at about 98 or about 253° C. In some embodiments, the crystalline Form II of Compound I can be characterized by DSC endotherms at about 98° C. and about 253° C. In some embodiments, the crystalline Form II of Compound I can be characterized by one or more differential scanning calorimetry (DSC) endotherms at about 98, 253, and about 273° C.

In some embodiments, the crystalline Form II of Compound I can be characterized by an XRPD pattern having peaks at 4.6, 9.2, 15.8, 17.8, 18.3, 19.2, 19.9, 22.4, 25.5 and 29.1 degrees 2θ (±0.2 degrees 2θ), wherein the XRPD is made using CuK$_{α1}$ radiation, and DSC endotherms at about 98 and about 253° C.

Form III

Form III of Compound I can be characterized by an X-ray powder diffraction (XRPD) pattern having at least three, four, five, or more, peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation. In some embodiments, the crystalline Form III of Compound I can be characterized by an X-ray powder diffraction (XRPD) pattern having at least three peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation. In some embodiments, the crystalline Form III of Compound I can be characterized by an X-ray powder diffraction (XRPD) pattern having at least four peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation. In some embodiments, the crystalline Form III of Compound I can be characterized by an X-ray powder diffraction (XRPD) pattern having at least five peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation.

Form III of Compound I can also be characterized by an X-ray powder diffraction (XRPD) pattern having at least six, seven, eight, nine, or more, peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation. In some embodiments, the crystalline Form III of Compound I can be characterized by an X-ray powder diffraction (XRPD) pattern having at least six peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation. In some embodiments, the crystalline Form III of Compound I can be characterized by an X-ray powder diffraction (XRPD) pattern having at least seven peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation. In some embodiments, the crystalline Form III of Compound I can be characterized by an X-ray powder diffraction (XRPD) pattern having at least eight peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation. In some embodiments, the crystalline Form III of Compound I can be characterized by an X-ray powder diffraction (XRPD) pattern having at least nine peaks at 5.0, 10.1, 15.2, 16.9, 20.3, 21.5, 22.0, 23.9, 25.2 or 29.4 degrees 2θ (±0.2 degrees 2θ), wherein the XRPD is made using CuK$_{α1}$ radiation.

In some embodiments, the crystalline Form III of Compound I can be characterized by an XRPD pattern having three or more peaks at 5.0, 10.1, 16.9, 20.3, 21.5, 22.0, 23.9 or 25.2 degrees 2θ (±0.2 degrees 2θ), wherein the XRPD is made using CuK$_{α1}$ radiation. In some embodiments, the crystalline Form III of Compound I can be characterized by an X-ray powder diffraction (XRPD) pattern having peaks at 5.0, 21.5, and 22.0 degrees 2θ (±0.2 degrees 2θ), wherein the XRPD is made using CuK$_{α1}$ radiation. In some embodiments, the crystalline Form III of Compound I can be characterized by an XRPD pattern further comprising one or more peaks at 10.1, 16.9, 20.3, 23.9 or 25.2 degrees 2θ (±0.2 degrees 2θ), wherein the XRPD is made using CuK$_{α1}$ radiation. In some embodiments, the crystalline Form III of Compound I can be characterized by an XRPD pattern further comprising two or more peaks at 10.1, 16.9, 20.3, 23.9 or 25.2 degrees 2θ (±0.2 degrees 2θ), wherein the XRPD is made using CuK$_{α1}$ radiation. In some embodiments, the crystalline Form III of Compound I can be characterized by an XRPD pattern further comprising three or more peaks at 10.1, 16.9, 20.3, 23.9 or 25.2 degrees 2θ (±0.2 degrees 2θ), wherein the XRPD is made using CuK$_{α1}$ radiation. In some embodiments, the crystalline Form III of Compound I can be characterized by an XRPD pattern further comprising four or more peaks at 10.1, 16.9, 20.3, 23.9 or 25.2 degrees 2θ (±0.2 degrees 2θ), wherein the XRPD is made using CuK$_{α1}$ radiation.

Figure 9:
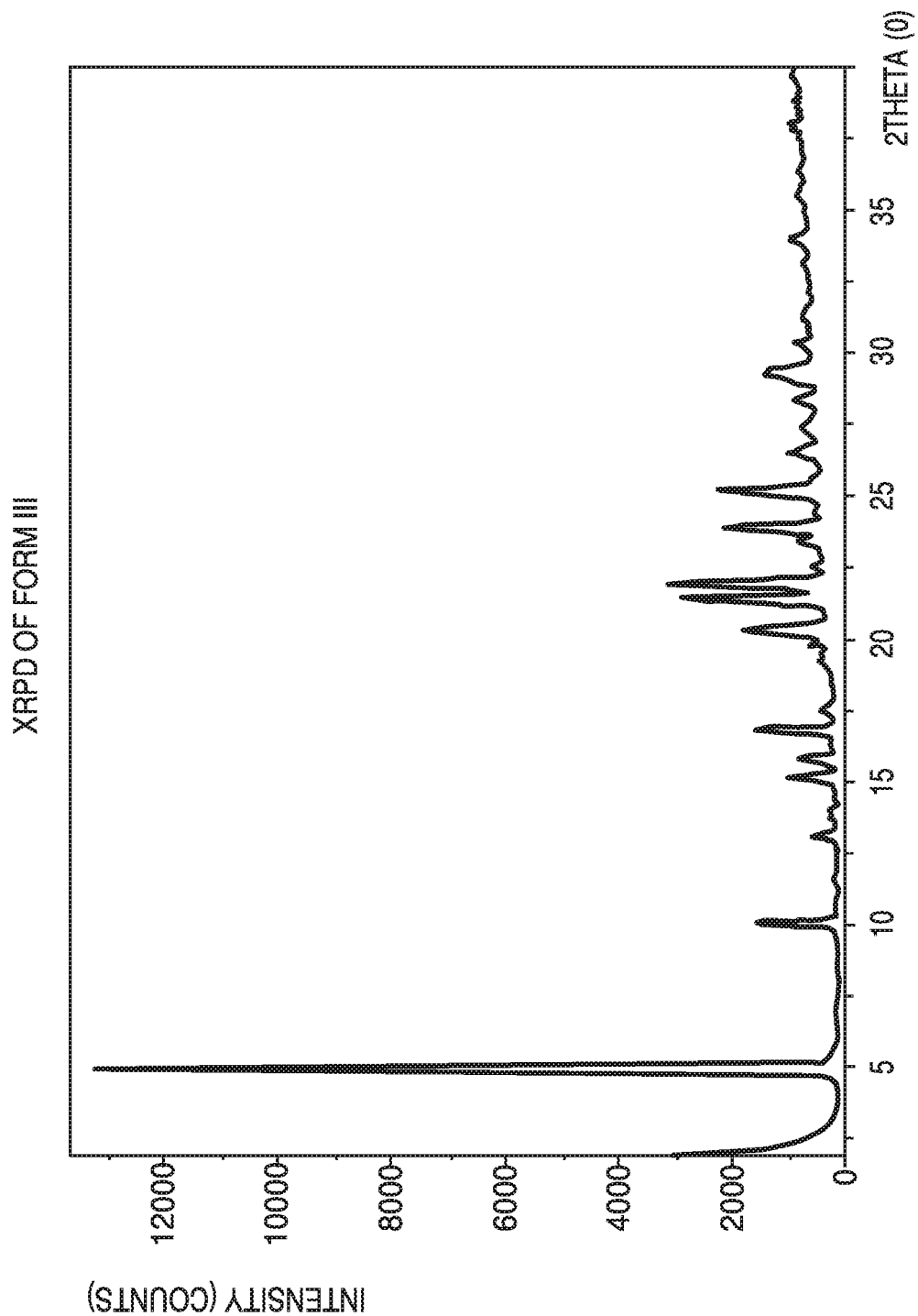
FIG. 9 shows an X-ray powder diffraction pattern of Compound I Form III.

In some embodiments, the crystalline Form III of Compound I can be characterized by an XRPD pattern having peaks at 5.0, 10.1, 15.2, 16.9, 20.3, 21.5, 22.0, 23.9, 25.2 and 29.4 degrees 2θ (±0.2 degrees 2θ), wherein the XRPD is made using CuK$_{α1}$ radiation. In some embodiments, the crystalline Form III of Compound I can be characterized by the XRPD pattern substantially in accordance with that of FIG. 9. In some embodiments, the crystalline Form III of Compound I can be substantially free of other crystalline forms of Compound I. In some embodiments, the crystalline Form III of Compound I can be substantially free of Form I, Form II and Form IV. In some embodiments, the crystalline Form III of Compound I can also be substantially free of Form V, Form VI, Form VII, Form VIII, Form IX, Form X, Form XI, Form XII, Form XIII and Form XIV.

Form III of Compound I can be characterized by a differential scanning calorimetry (DSC) plot having at least one or more endotherms at about 181° C. or about 272° C. In some embodiments, the crystalline Form III of Compound I can be characterized by a differential scanning calorimetry (DSC) endotherm at about 181° C. or about 272° C. In some embodiments, the crystalline Form III of Compound I can be characterized by a differential scanning calorimetry (DSC) endotherm at about 181° C. In some embodiments, the crystalline Form III of Compound I can be characterized by a differential scanning calorimetry (DSC) endotherm at about 181° C. and about 272° C.

In some embodiments, the crystalline Form III of Compound I can be characterized by an XRPD pattern having peaks at 5.0, 10.1, 15.2, 16.9, 20.3, 21.5, 22.0, 23.9, 25.2 and 29.4 degrees 2θ (±0.2 degrees 2θ), wherein the XRPD is made using CuK$_{α1}$ radiation, and a DSC endotherm at about 181° C.

Form IV

Form IV of Compound I can be characterized by an X-ray powder diffraction (XRPD) pattern having at least three, four, five, or more, peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation. In some embodiments, the crystalline Form IV of Compound I can be can be characterized by an X-ray powder diffraction (XRPD) pattern having at least three peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation. In some embodiments, the crystalline Form IV of Compound I can be can be characterized by an X-ray powder diffraction (XRPD) pattern having at least four peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation. In some embodiments, the crystalline Form IV of Compound I can be can be characterized by an X-ray powder diffraction (XRPD) pattern having at least five peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation.

Form IV of Compound I can also be characterized by an X-ray powder diffraction (XRPD) pattern having at least six, seven, eight, nine, or more, peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation. In some embodiments, the crystalline Form IV of Compound I can be can be characterized by an X-ray powder diffraction (XRPD) pattern having at least six peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation. In some embodiments, the crystalline Form IV of Compound I can be can be characterized by an X-ray powder diffraction (XRPD) pattern having at least seven peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation. In some embodiments, the crystalline Form IV of Compound I can be can be characterized by an X-ray powder diffraction (XRPD) pattern having at least eight peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation. In some embodiments, the crystalline Form IV of Compound I can be can be characterized by an X-ray powder diffraction (XRPD) pattern having at least nine peaks at 4.1, 8.8, 16.8, 18.1, 18.7, 19.7, 21.1, 21.4, 23.8, or 26.6 degrees 2θ (±0.2 degrees 2θ), wherein the XRPD is made using CuK$_{α1}$ radiation.

In some embodiments, the crystalline Form IV of Compound I can be characterized by an XRPD pattern having three or more peaks at 4.1, 18.1, 18.7, 23.8, and 26.6 degrees 2θ (±0.2 degrees 2θ), wherein the XRPD is made using CuK$_{α1}$ radiation. In some embodiments, the crystalline Form IV of Compound I can be characterized by an XRPD pattern further comprising one or more peaks at 8.8, 16.8, 19.7, 21.1, or 21.4 degrees 2θ (±0.2 degrees 2θ), wherein the XRPD is made using CuK$_{α1}$ radiation. In some embodiments, the crystalline Form IV of Compound I can be characterized by an XRPD pattern further comprising two or more peaks at 8.8, 16.8, 19.7, 21.1, or 21.4 degrees 2θ (±0.2 degrees 2θ), wherein the XRPD is made using CuK$_{α1}$ radiation. In some embodiments, the crystalline Form IV of Compound I can be characterized by an XRPD pattern further comprising three or more peaks at 8.8, 16.8, 19.7, 21.1, or 21.4 degrees 2θ (±0.2 degrees 2θ), wherein the XRPD is made using CuK$_{α1}$ radiation. In some embodiments, the crystalline Form IV of Compound I can be characterized by an XRPD pattern further comprising four or more peaks at 8.8, 16.8, 19.7, 21.1, or 21.4 degrees 2θ (±0.2 degrees 2θ), wherein the XRPD is made using CuK$_{α1}$ radiation.

Figure 13:
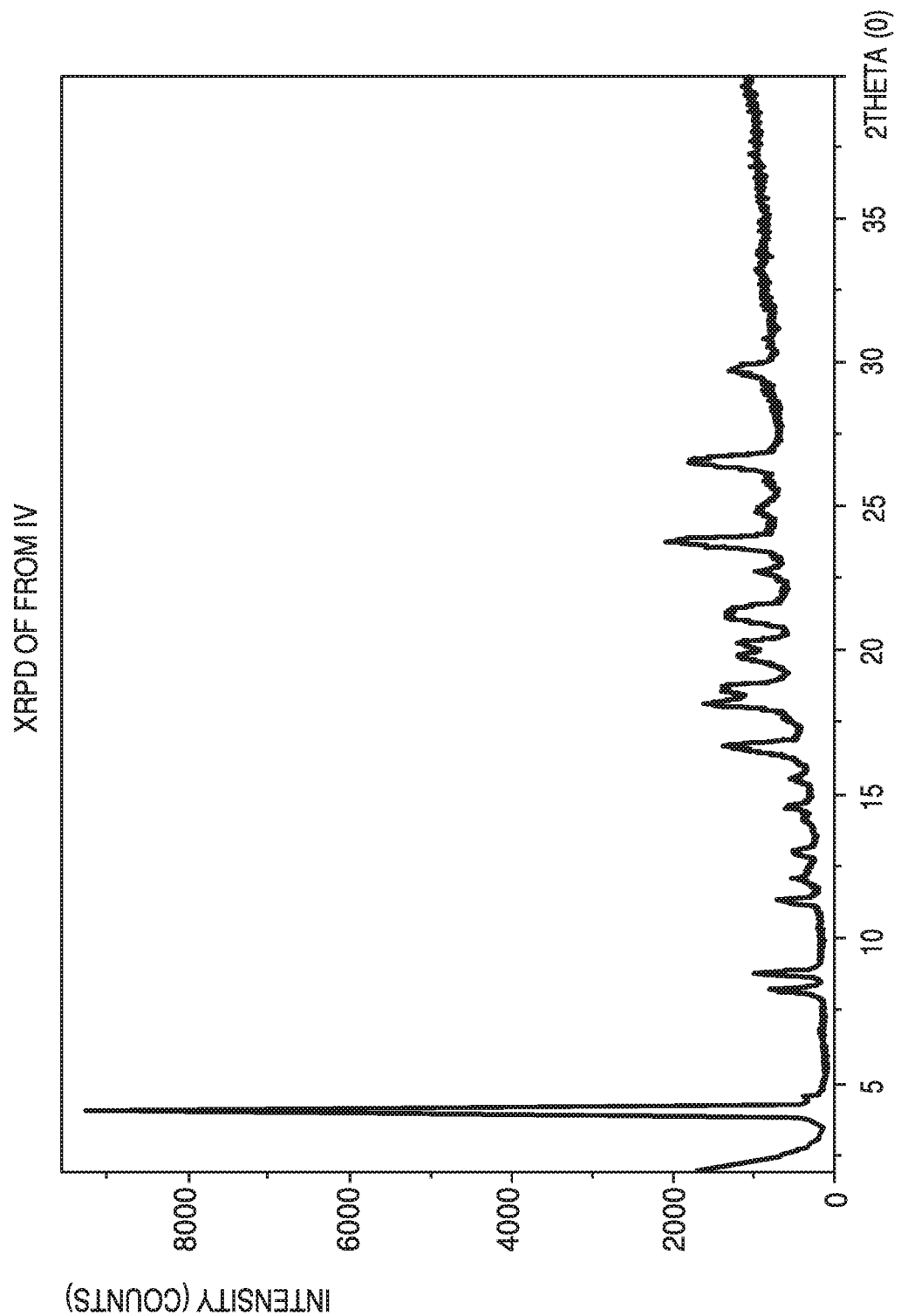
FIG. 13 shows an X-ray powder diffraction pattern of Compound I Form IV.
Figure 15:
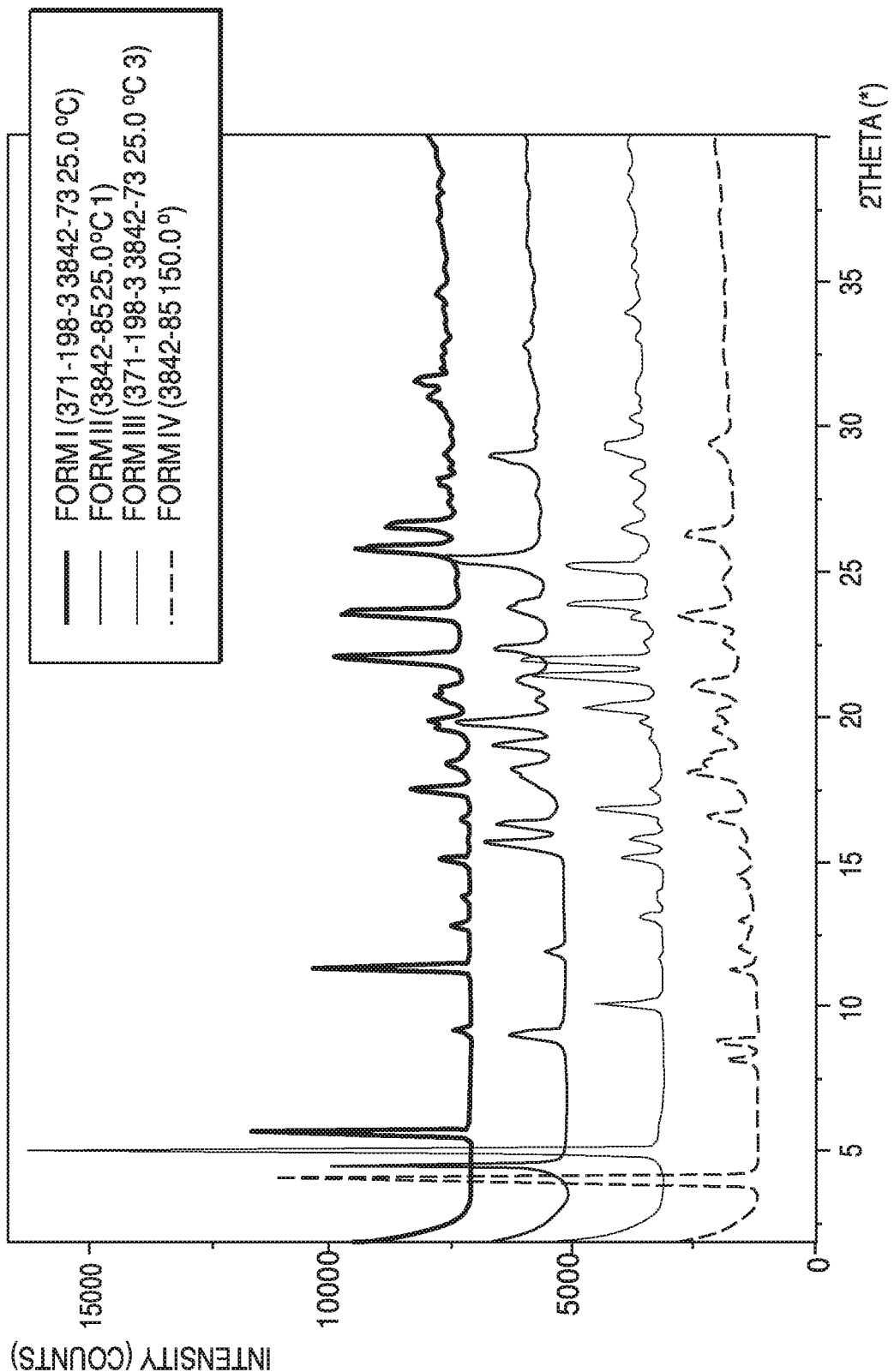
FIG. 15 shows an X-ray powder diffraction pattern of Compound I Forms I, II, III and IV.

In some embodiments, the crystalline Form IV of Compound I can be characterized by an XRPD pattern having peaks at 4.1, 8.8, 16.8, 18.1, 18.7, 19.7, 21.1, 21.4, 23.8, and 26.6 degrees 2θ (±0.2 degrees 2θ), wherein the XRPD is made using CuK$_{α1}$ radiation. In some embodiments, the crystalline Form IV of Compound I can be characterized by the XRPD pattern substantially in accordance with that of FIG. 13. In some embodiments, the crystalline Form IV of Compound I can be substantially free of other crystalline forms of Compound I. In some embodiments, the crystalline Form IV of Compound I can be substantially free of Form I, Form II and Form III. In some embodiments, the crystalline Form IV of Compound I can also be substantially free of Form V, Form VI, Form VII, Form VIII, Form IX, Form X, Form XI, Form XII, Form XIII and Form XIV.

Forms V to VIII

Figure 16:
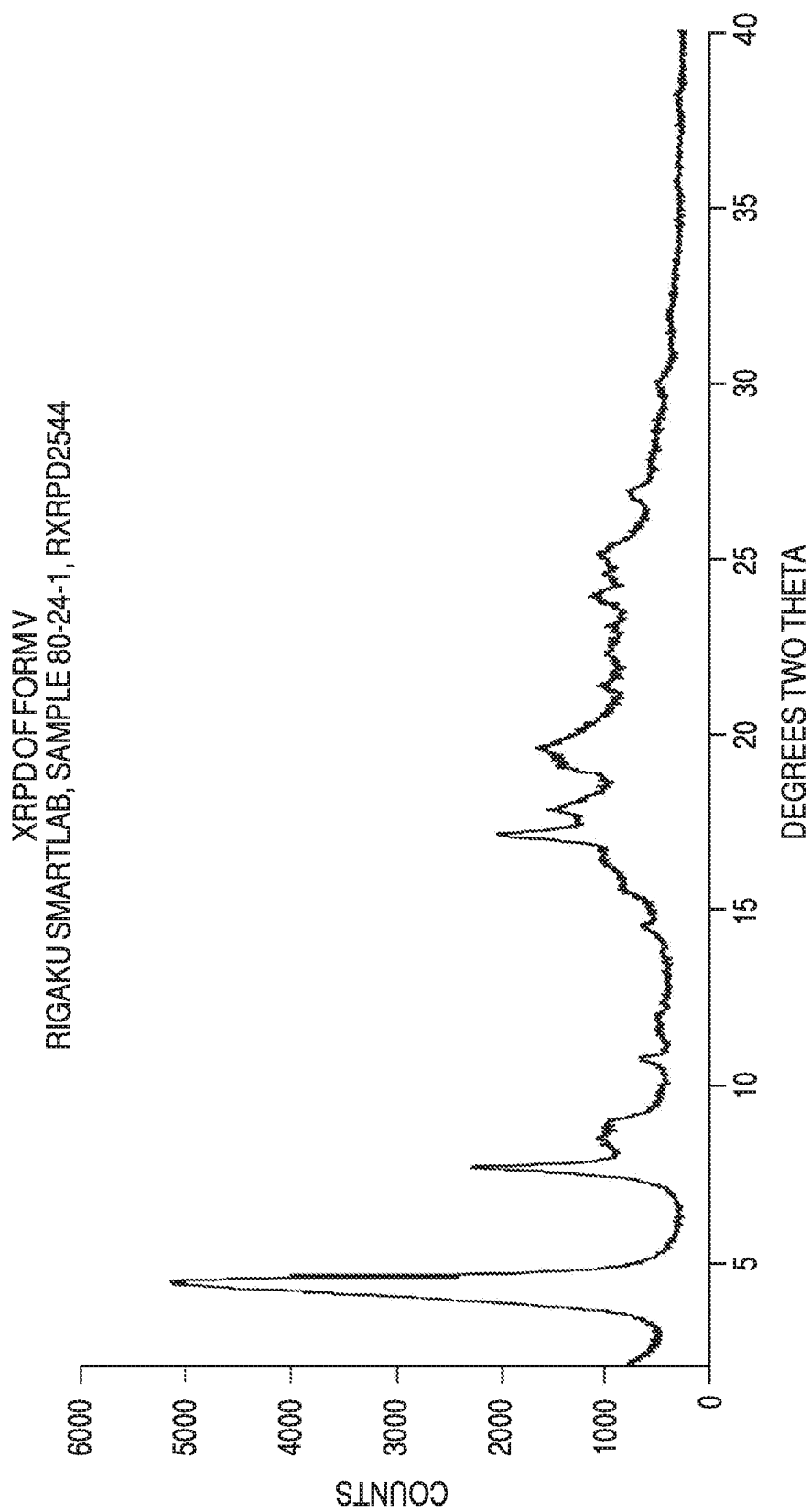
FIG. 16 shows an X-ray powder diffraction pattern of Compound I Form V.

Form V of Compound I can be characterized by an X-ray powder diffraction (XRPD) pattern substantially in accordance with that of FIG. 16. Form V can be any suitable solvate or hydrate form. In some embodiments, Form V of Compound I can be a solvate with hexafluoroisopropanol.

Figure 17:
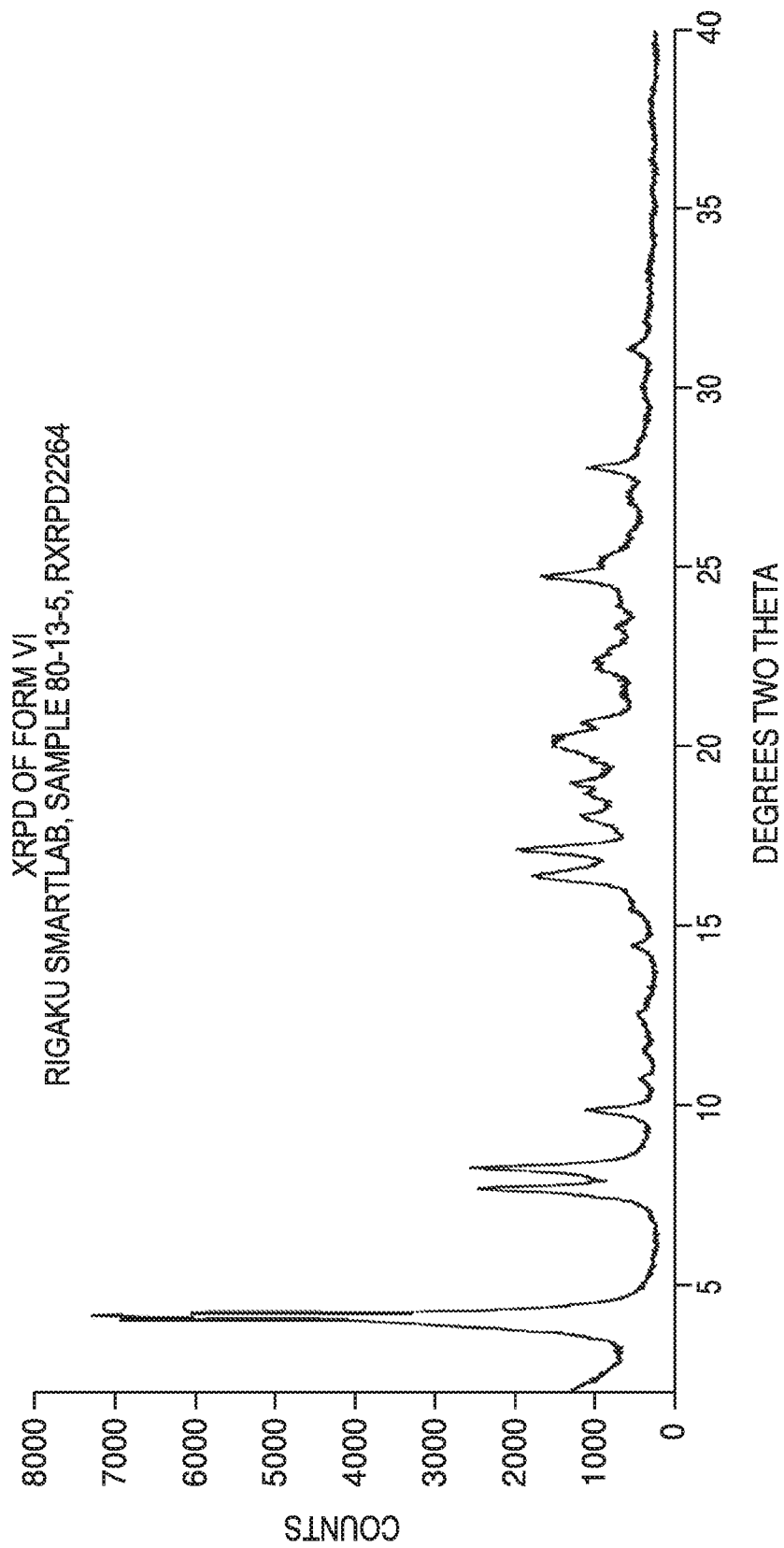
FIG. 17 shows an X-ray powder diffraction pattern of Compound I Form VI.

Form VI of Compound I can be characterized by an X-ray powder diffraction (XRPD) pattern substantially in accordance with that of FIG. 17. Form VI can be any suitable solvate or hydrate form.

Figure 18:
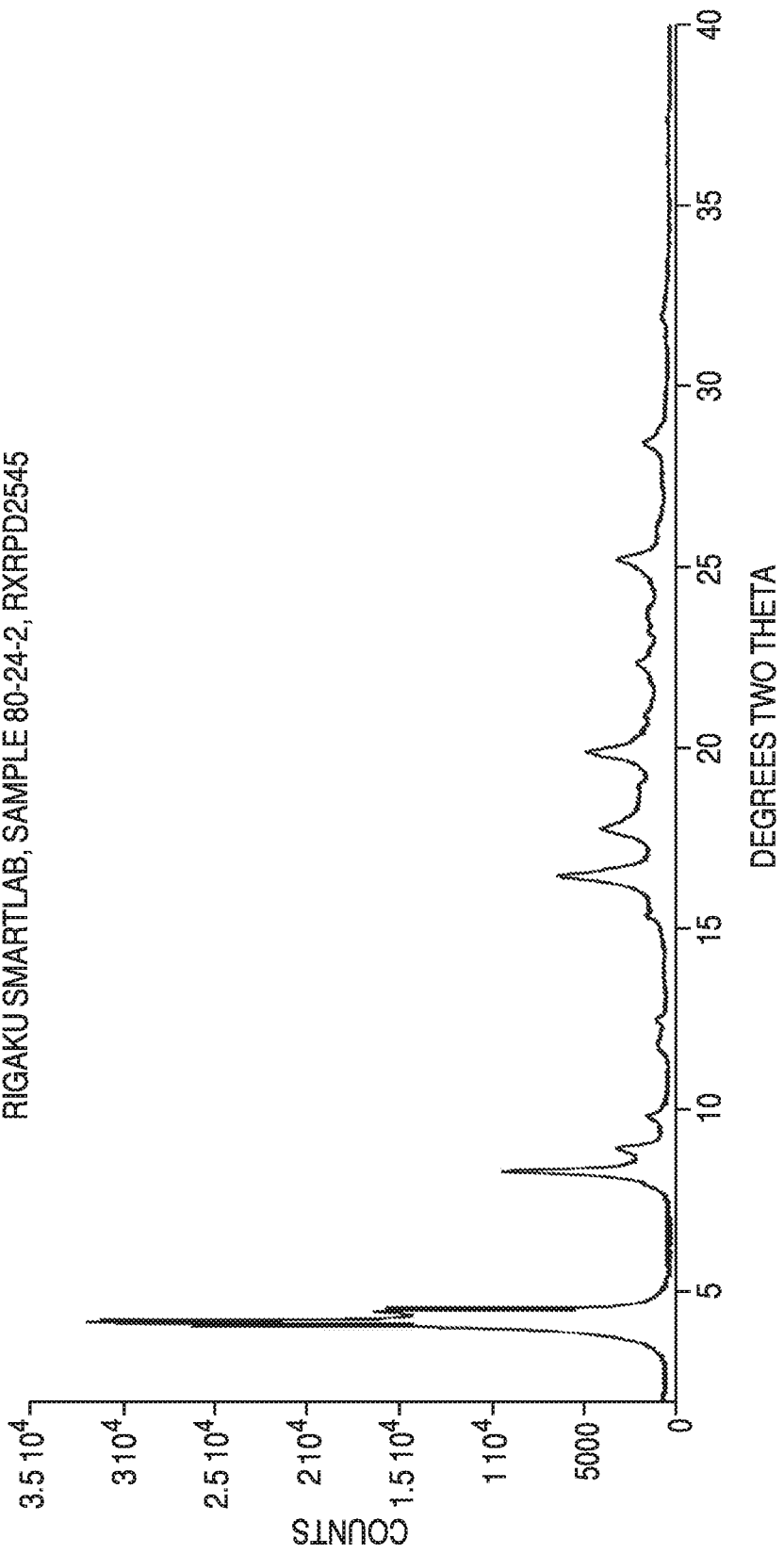
FIG. 18 shows an X-ray powder diffraction pattern of Compound I Form VII.

Form VII of Compound I can be characterized by an X-ray powder diffraction (XRPD) pattern substantially in accordance with that of FIG. 18. Form VII can be any suitable solvate or hydrate form. In some embodiments, Form VII of Compound I can be a solvate with trifluoroethanol.

Figure 19:
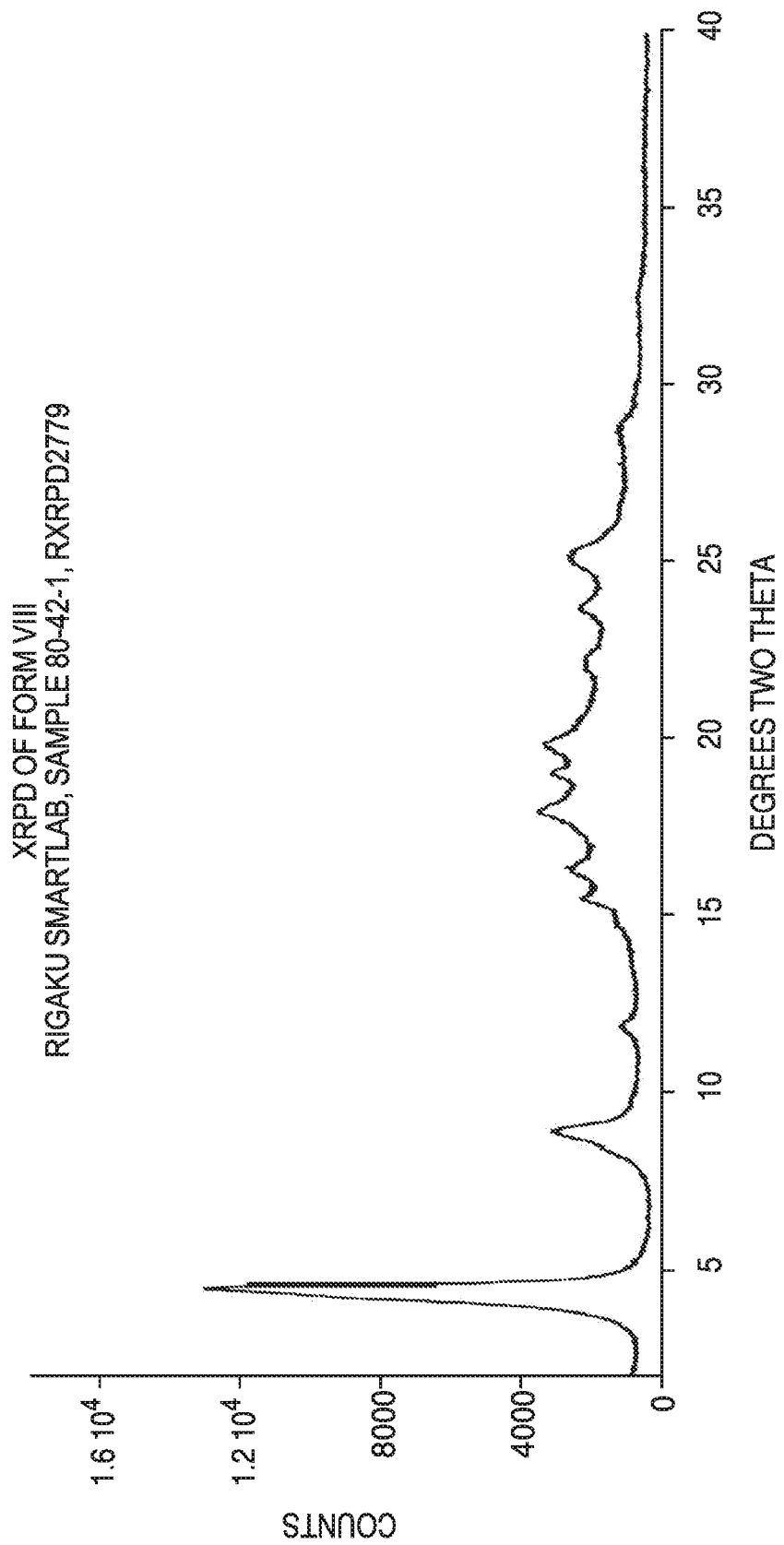
FIG. 19 shows an X-ray powder diffraction pattern of Compound I Form VIII.

Form VIII of Compound I can be characterized by an X-ray powder diffraction (XRPD) pattern substantially in accordance with that of FIG. 19. Form VIII can be any suitable solvate or hydrate form, such as a hemihydrate.

In some embodiments, the crystalline Form V of Compound I can be substantially free of Form I, Form II, Form III, Form IV, Form VI, Form VII, Form VIII, Form IX, Form X, Form XI, Form XII, Form XIII and Form XIV. In some embodiments, the crystalline Form VI of Compound I can be substantially free of Form I, Form II, Form III, Form IV, Form V, Form VII, Form VIII, Form IX, Form X, Form XI, Form XII, Form XIII and Form XIV. In some embodiments, the crystalline Form VII of Compound I can be substantially free of Form I, Form II, Form III, Form IV, Form V, Form VI, Form VIII, Form IX, Form X, Form XI, Form XII, Form XIII and Form XIV. In some embodiments, the crystalline Form VIII of Compound I can be substantially free of Form I, Form II, Form III, Form IV, Form V, Form VI, Form VII, Form IX, Form X, Form XI, Form XII, Form XIII and Form XIV.

Form IX

Form IX of Compound I can be characterized by an X-ray powder diffraction (XRPD) pattern having at least three, four, five, or more, peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{α1}$ radiation. In some embodiments, the crystalline Form IX of Compound I can be characterized by an X-ray powder diffraction (XRPD) pattern having at least three peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{α1}$ radiation. In some embodiments, the crystalline Form IX of Compound I can be characterized by an X-ray powder diffraction (XRPD) pattern having at least four peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an X-ray powder diffraction (XRPD) pattern having at least five peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation.

Form IX of Compound I can also be characterized by an X-ray powder diffraction (XRPD) pattern having at least six, seven, eight, nine, or more, peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an X-ray powder diffraction (XRPD) pattern having at least six peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an X-ray powder diffraction (XRPD) pattern having at least seven peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an X-ray powder diffraction (XRPD) pattern having at least eight peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an X-ray powder diffraction (XRPD) pattern having at least nine peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation.

In some embodiments, the crystalline Form IX of Compound I can be characterized by an XRPD pattern having three or more peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation.

In some embodiments, the crystalline Form IX of Compound I can be characterized by an X-ray powder diffraction (XRPD) pattern having peaks at 5.3, 9.8, and 15.6 degrees 2θ (±0.2 degrees 2θ), wherein the XRPD is made using CuK$_{\alpha 1}$ radiation. In some embodiments, the crystalline Form IX of Compound I can be characterized by an XRPD pattern further comprising one or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an XRPD pattern further comprising two or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an XRPD pattern further comprising three or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an XRPD pattern further comprising four or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystalline Form IX of Compound I can be characterized by an XRPD pattern further comprising five or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation. In some embodiments, the crystal-line Form IX of Compound I can be characterized by an XRPD pattern further comprising six or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation.

Figure 20:
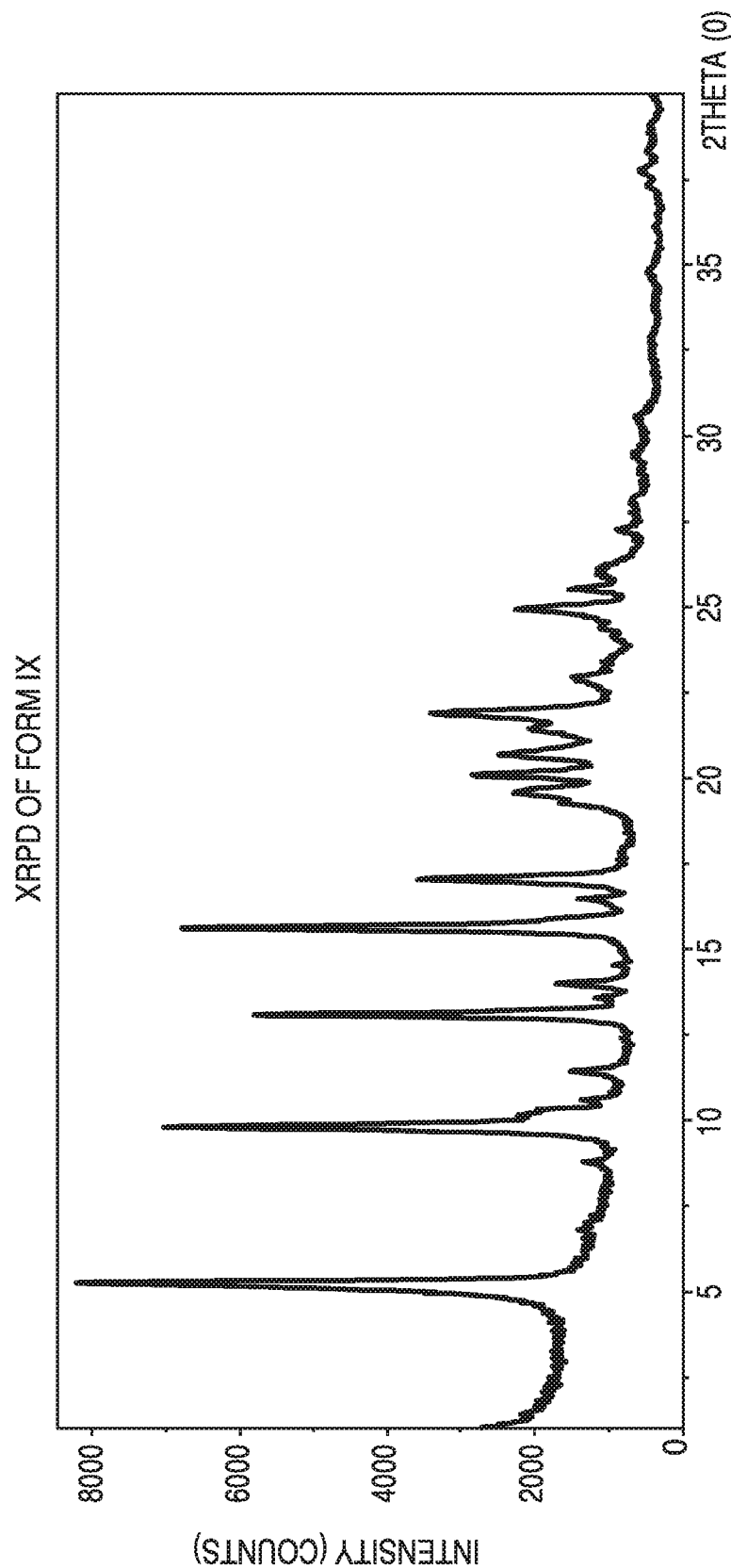
FIG. 20 shows an X-ray powder diffraction pattern of Compound I Form IX.
Figure 22:
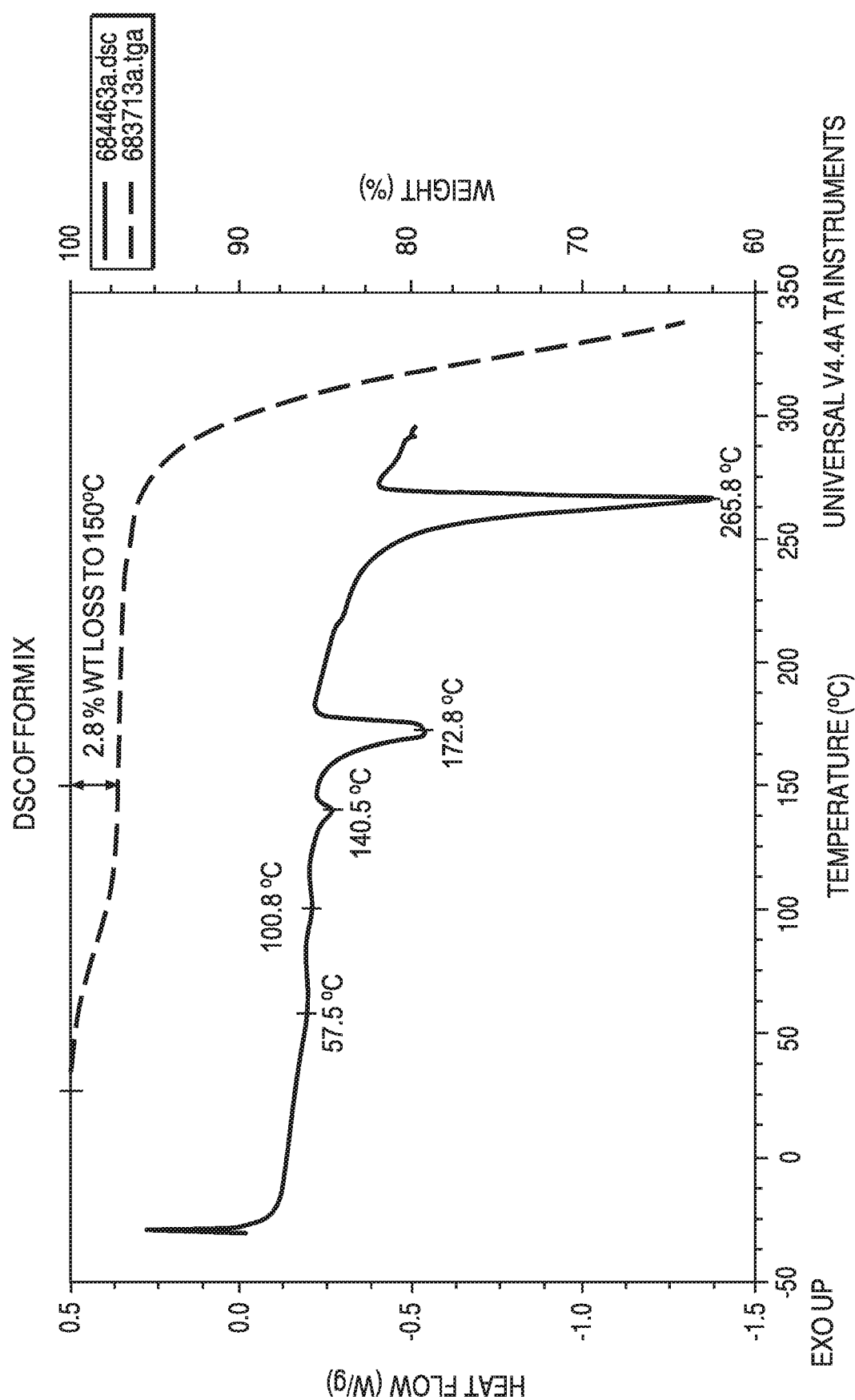
FIG. 22 shows a differential scanning calorimetry plot of Compound I Form IX.

In some embodiments, the crystalline Form IX of Compound I can be characterized by an XRPD pattern having peaks at 5.3, 9.8, 13.1, 15.6, 17.0, 19.6, 20.0, 20.7, 21.9 and 24.9 degrees 2θ (±0.2 degrees 2θ), wherein the XRPD is made using CuK$_{\alpha 1}$ radiation. In some embodiments, the crystalline Form IX of Compound I can be characterized by the XRPD pattern substantially in accordance with that of FIG. 20. In some embodiments, the crystalline Form IX of Compound I can be substantially free of other crystalline forms of Compound I. In some embodiments, the crystalline Form IX of Compound I can be substantially free of Form I, Form II, Form III, Form IV, Form V, Form VI, Form VII, Form VIII, Form X, Form XI, Form XII, Form XIII and Form XIV.

Form IX of Compound I can be characterized by a differential scanning calorimetry (DSC) plot having at least one or more endotherm at about 57, 101, 141, 173, or about 266° C. In some embodiments, the crystalline Form IX of Compound I can be characterized by a differential scanning calorimetry (DSC) endotherm at about 57, 101, 141, 173, or about 266° C. In some embodiments, the crystalline Form IX of Compound I can be characterized by a differential scanning calorimetry (DSC) endotherm at about 141 or about 173° C. In some embodiments, the crystalline Form IX of Compound I can be characterized by a differential scanning calorimetry (DSC) endotherm at about 141 and about 173° C. In some embodiments, the crystalline Form IX of Compound I can be characterized by a differential scanning calorimetry (DSC) endotherm at about 173 and about 266° C. In some embodiments, the crystalline Form IX of Compound I can be characterized by a differential scanning calorimetry (DSC) endotherm at about 173° C. In some embodiments, the crystalline Form IX of Compound I can be characterized by a differential scanning calorimetry (DSC) endotherm at about 57, 101, 141, 173, and about 266° C.

In some embodiments, the crystalline Form IX of Compound I can be characterized by an XRPD pattern having peaks at 5.3, 9.8, 13.1, 15.6, 17.0, 19.6, 20.0, 20.7, 21.9 and 24.9 degrees 2θ (±0.2 degrees 2θ), wherein the XRPD is made using CuK$_{\alpha 1}$ radiation, and a DSC endotherm at about 173° C.

The crystalline Form IX of Compound I can also have a solvate or hydrate form. In some embodiments, the crystalline Form IX of Compound I can be a hydrate.

Form X

Form X of Compound I can be characterized by an X-ray powder diffraction (XRPD) pattern having at least three, four, five, or more, peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{\alpha 1}$ radiation. In some embodiments, the crystalline Form X of Compound I can be characterized by an X-ray powder diffraction (XRPD) pattern having at least three peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{\alpha 1}$ radiation. In some embodiments, the crystalline Form X of Compound I can be characterized by an X-ray powder diffraction (XRPD) pattern having at least four peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{\alpha 1}$ radiation. In some embodiments, the crystalline Form X of Compound I can be characterized by an X-ray powder diffraction (XRPD) pattern having at least five peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{α1}$ radiation.

Form X of Compound I can also be characterized by an X-ray powder diffraction (XRPD) pattern having at least six, seven, eight, nine, or more, peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an X-ray powder diffraction (XRPD) pattern having at least six peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an X-ray powder diffraction (XRPD) pattern having at least seven peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an X-ray powder diffraction (XRPD) pattern having at least eight peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an X-ray powder diffraction (XRPD) pattern having at least nine peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{α1}$ radiation.

In some embodiments, the crystalline Form X of Compound I can be characterized by an XRPD pattern having three or more peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an X-ray powder diffraction (XRPD) pattern having peaks at 5.5, 10.8 and 16.0 degrees 2θ (±0.2 degrees 2θ), wherein the XRPD is made using CuK$_{α1}$ radiation. In some embodiments, the crystalline Form X of Compound I can be characterized by an XRPD pattern further comprising one or more peaks at 9.4, 11.9, 12.9, 14.4, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an XRPD pattern further comprising two or more peaks at 9.4, 11.9, 12.9, 14.4, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an XRPD pattern further comprising three or more peaks at 9.4, 11.9, 12.9, 14.4, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an XRPD pattern further comprising four or more peaks at 9.4, 11.9, 12.9, 14.4, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an XRPD pattern further comprising five or more peaks at 9.4, 11.9, 12.9, 14.4, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by an XRPD pattern further comprising six or more peaks at 9.4, 11.9, 12.9, 14.4, 19.0, 21.9, or 23.9 degrees 2θ (±0.2 degrees 2θ), wherein the XRPD is made using CuK$_{α1}$ radiation.

Figure 23:
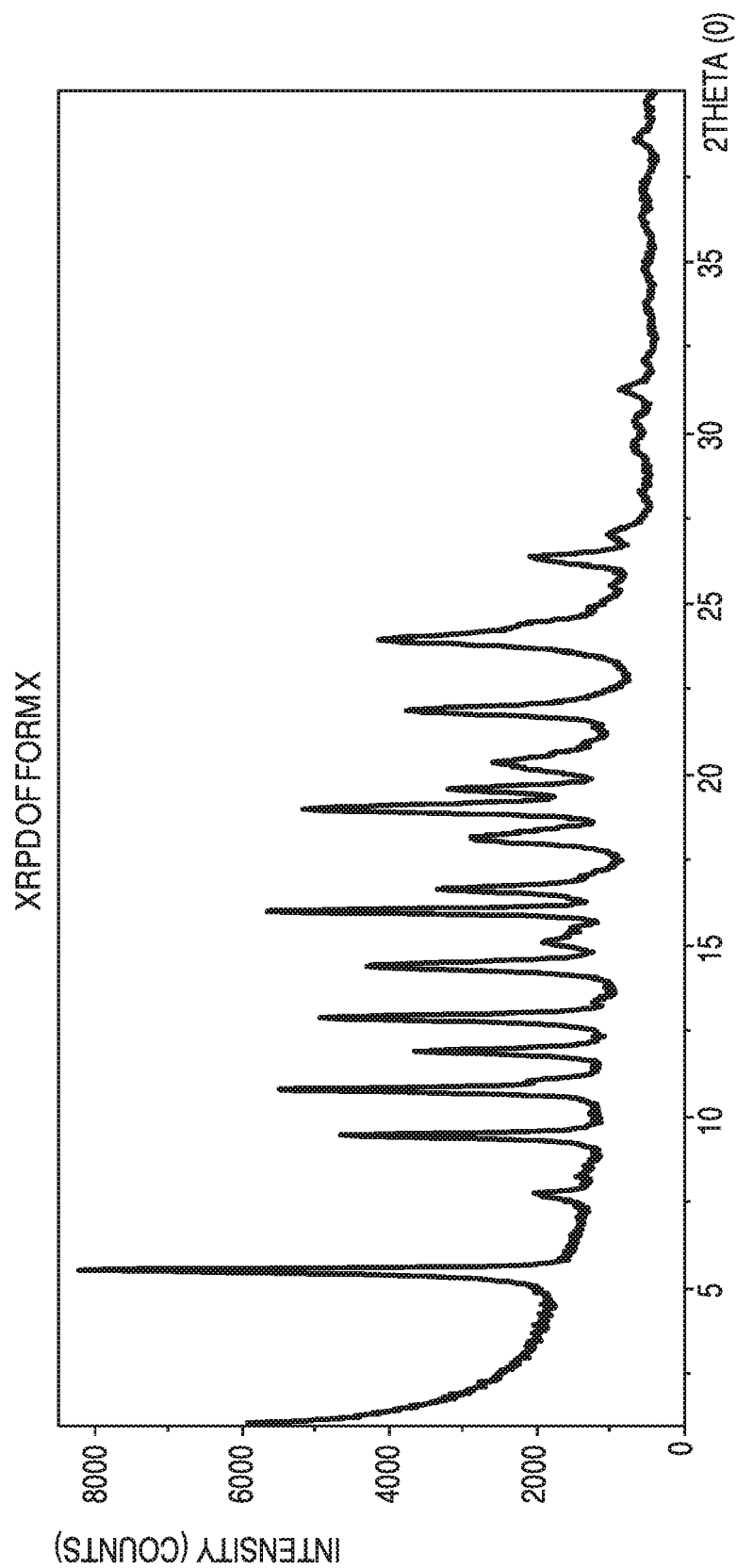
FIG. 23 shows an X-ray powder diffraction pattern of Compound I Form X.
Figure 25:
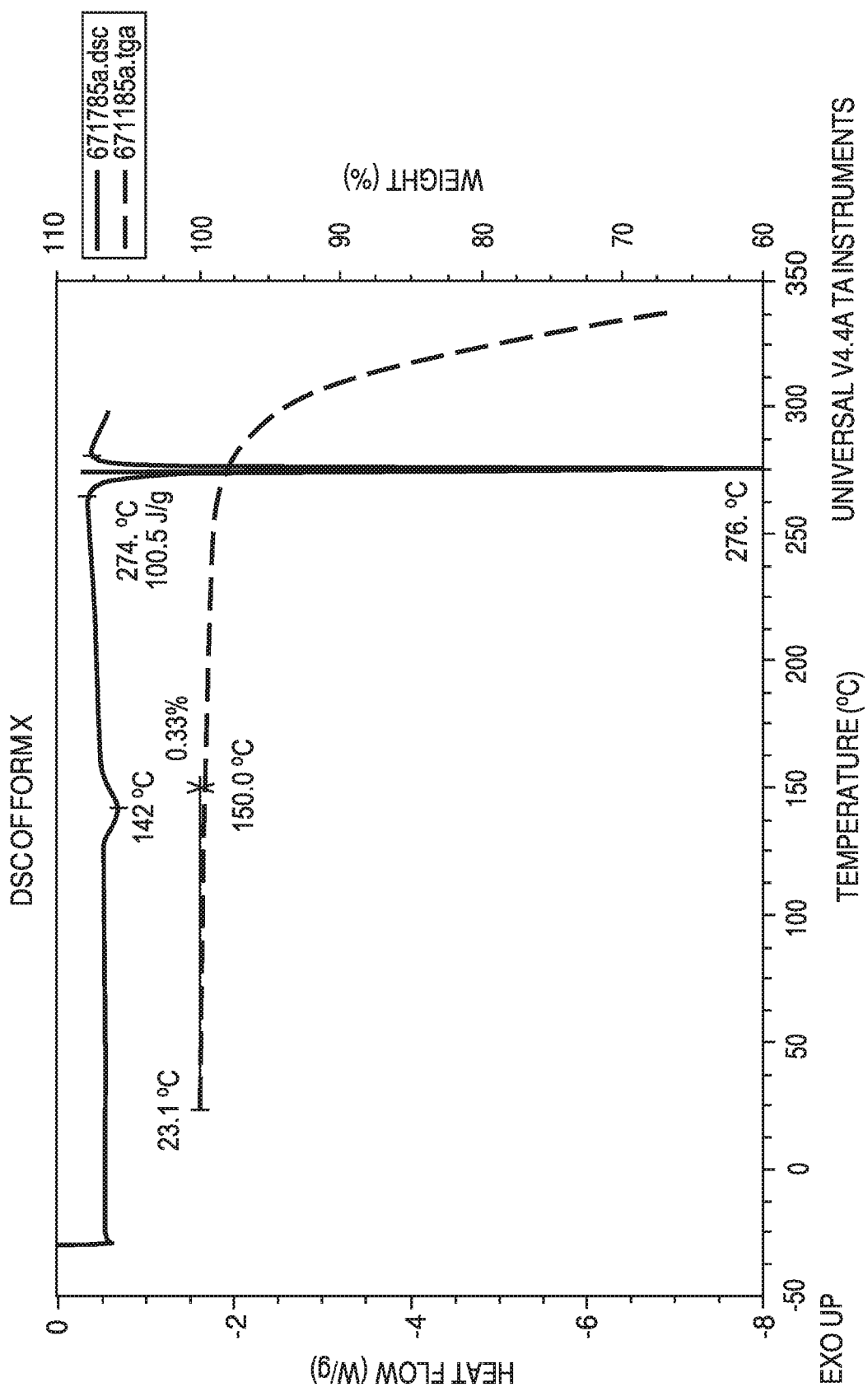
FIG. 25 shows a differential scanning calorimetry plot of Compound I Form X.

In some embodiments, the crystalline Form X of Compound I can be characterized by an XRPD pattern having peaks at 5.5, 9.4, 10.8, 11.9, 12.9, 14.4, 16.0, 19.0, 21.9, or 23.9 degrees 2θ (±0.2 degrees 2θ), wherein the XRPD is made using CuK$_{α1}$ radiation. In some embodiments, the crystalline Form X of Compound I can be characterized by the XRPD pattern substantially in accordance with that of FIG. 23. In some embodiments, the crystalline Form X of Compound I can be substantially free of other crystalline forms of Compound I. In some embodiments, the crystalline Form X of Compound I can be substantially free of Form I, Form II, Form III, Form IV, Form V, Form VI, Form VII, Form VIII, Form IX, Form XI, Form XII, Form XIII and Form XIV.

Form X of Compound I can be characterized by a differential scanning calorimetry (DSC) plot having at least one endotherm at about 142° C. or about 274° C. In some embodiments, the crystalline Form X of Compound I can be characterized by a differential scanning calorimetry (DSC) endotherm at about 142 or about 274° C. In some embodiments, the crystalline Form X of Compound I can be characterized by a differential scanning calorimetry (DSC) endotherm at about 142° C. In some embodiments, the crystalline Form X of Compound I can be characterized by a differential scanning calorimetry (DSC) endotherm at about 142 and about 274° C.

In some embodiments, the crystalline Form X of Compound I can be characterized by an XRPD pattern having peaks at 5.5, 9.4, 10.8, 11.9, 12.9, 14.4, 16.0, 19.0, 21.9, and 23.9 degrees 2θ (±0.2 degrees 2θ), wherein the XRPD is made using CuK$_{α1}$ radiation, and a DSC endotherm at about 142° C.

Form XI

Form XI of Compound I can be characterized by an X-ray powder diffraction (XRPD) pattern having at least three, four, five, or more, peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an X-ray powder diffraction (XRPD) pattern having at least three peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an X-ray powder diffraction (XRPD) pattern having at least four peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an X-ray powder diffraction (XRPD) pattern having at least five peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation.

Form XI of Compound I can also be characterized by an X-ray powder diffraction (XRPD) pattern having at least six, seven, eight, nine, or more, peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an X-ray powder diffraction (XRPD) pattern having at least six peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an X-ray powder diffraction (XRPD) pattern having at least seven peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an X-ray powder diffraction (XRPD) pattern having at least eight peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an X-ray powder diffraction (XRPD) pattern having at least nine peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation.

In some embodiments, the crystalline Form XI of Compound I can be characterized by an XRPD pattern having three or more peaks at 7.7, 8.4, 10.7, 17.1, 17.8, 19.3, 19.5, 21.4, 23.0 or 23.9 degrees 2θ (±0.2 degrees 2θ), wherein the XRPD is made using CuK$_{α1}$ radiation.

In some embodiments, the crystalline Form XI of Compound I can be characterized by an X-ray powder diffraction (XRPD) pattern having peaks at 7.7, 17.1 and 19.5 degrees 2θ (±0.2 degrees 2θ), wherein the XRPD is made using CuK$_{α1}$ radiation. In some embodiments, the crystalline Form XI of Compound I can be characterized by an XRPD pattern further comprising one or more peaks at 8.4, 10.7, 17.8, 19.3, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an XRPD pattern further comprising two or more peaks at 8.4, 10.7, 17.8, 19.3, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an XRPD pattern further comprising three or more peaks at 8.4, 10.7, 17.8, 19.3, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an XRPD pattern further comprising four or more peaks at 8.4, 10.7, 17.8, 19.3, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an XRPD pattern further comprising five or more peaks at 8.4, 10.7, 17.8, 19.3, 21.4, 23.0 or 23.9 degrees 2θ (±0.2 degrees 2θ), wherein the XRPD is made using CuK$_{α1}$ radiation. In some embodiments, the crystalline Form XI of Compound I can be characterized by an XRPD pattern further comprising six or more peaks at 8.4, 10.7, 17.8, 19.3, 21.4, 23.0 or 23.9 degrees 2θ (±0.2 degrees 2θ), wherein the XRPD is made using CuK$_{α1}$ radiation.

Figure 26:
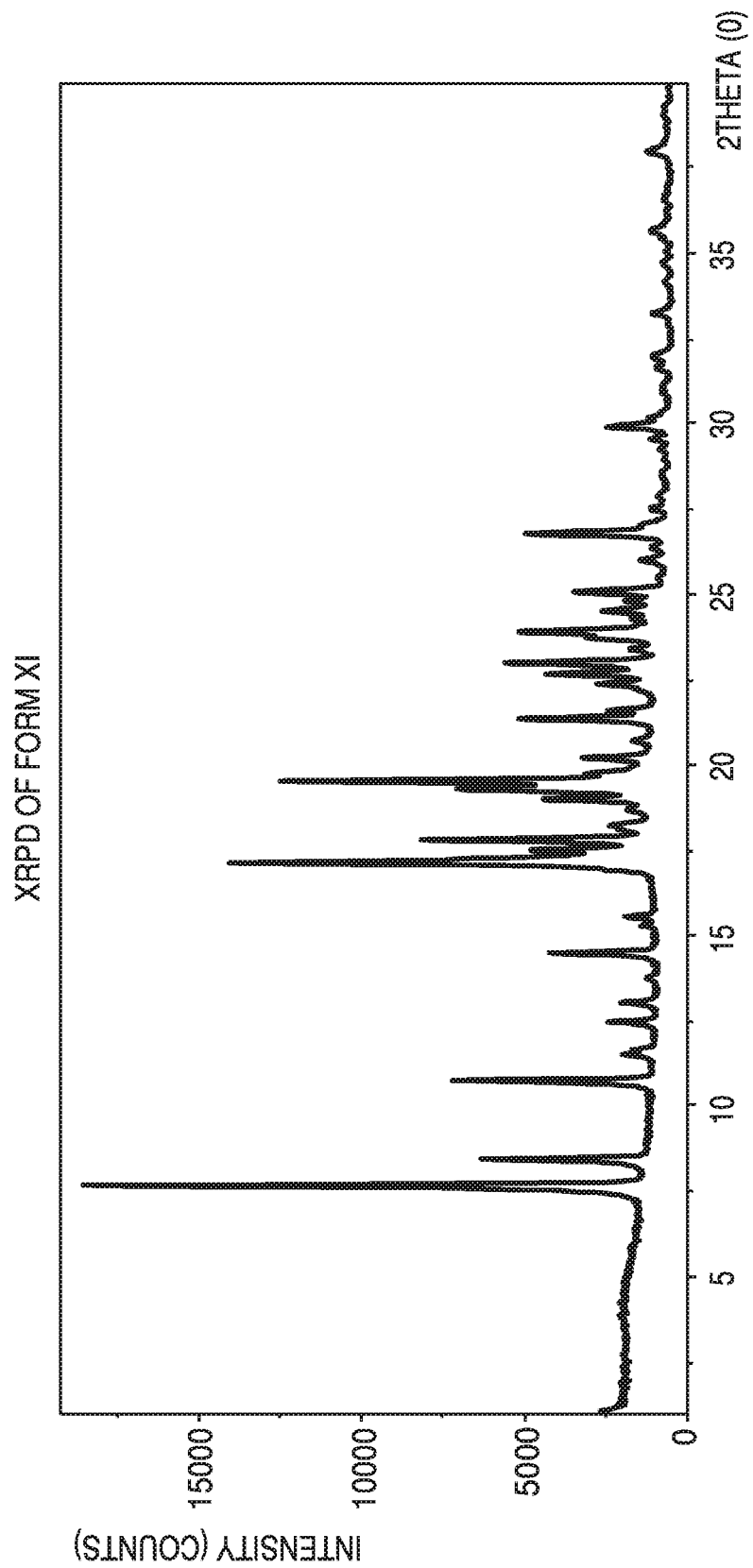
FIG. 26 shows an X-ray powder diffraction pattern of Compound I Form XI.

In some embodiments, the crystalline Form XI of Compound I can be characterized by an XRPD pattern having peaks at 7.7, 8.4, 10.7, 17.1, 17.8, 19.3, 19.5, 21.4, 23.0 and 23.9 degrees 2θ (±0.2 degrees 2θ), wherein the XRPD is made using CuK$_{α1}$ radiation. In some embodiments, the crystalline Form XI of Compound I can be characterized by the XRPD pattern substantially in accordance with that of FIG. 26. In some embodiments, the crystalline Form XI of Compound I can be substantially free of other crystalline forms of Compound I. In some embodiments, the crystalline Form XI of Compound I can be substantially free of Form I, Form II, Form III, Form IV, Form V, Form VI, Form VII, Form VIII, Form IX, Form X, Form XII, Form XIII, and Form XIV.

The crystalline Form XI of Compound I can also have a solvate or hydrate form. In some embodiments, the crystalline Form XI of Compound I can be a solvate with hexafluoroisopropanol (HFIPA).

Form XII

Form XII of Compound I can be characterized by an X-ray powder diffraction (XRPD) pattern having at least three, four, five, or more, peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation. In some embodiments, the crystalline Form XII of Compound I can be characterized by an X-ray powder diffraction (XRPD) pattern having at least three peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation. In some embodiments, the crystalline Form XII of Compound I can be characterized by an X-ray powder diffraction (XRPD) pattern having at least four peaks at 6.0, 9.0, 10.9, 13.7, 17.1, 18.7, 20.3, 21.1, 21.9 or 25.8 degrees 2θ (±0.2 degrees 2θ), wherein the XRPD is made using CuK$_{α1}$ radiation. In some embodiments, the crystalline Form XII of Compound I can be characterized by an X-ray powder diffraction (XRPD) pattern having at least five peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation.

Form XII of Compound I can also be characterized by an X-ray powder diffraction (XRPD) pattern having at least six, seven, eight, nine, or more, peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation. In some embodiments, the crystalline Form XII of Compound I can be characterized by an X-ray powder diffraction (XRPD) pattern having at least six peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation. In some embodiments, the crystalline Form XII of Compound I can be characterized by an X-ray powder diffraction (XRPD) pattern having at least seven peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation. In some embodiments, the crystalline Form XII of Compound I can be characterized by an X-ray powder diffraction (XRPD) pattern having at least eight peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation. In some embodiments, the crystalline Form XII of Compound I can be characterized by an X-ray powder diffraction (XRPD) pattern having at least nine peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation.

In some embodiments, the crystalline Form XII of Compound I can be characterized by an XRPD pattern having three or more peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation. In some embodiments, the crystalline Form XII of Compound I can be characterized by an X-ray powder diffraction (XRPD) pattern having peaks at 20.3, 21.1 and 21.9 degrees 2θ (±0.2 degrees 2θ), wherein the XRPD is made using CuK$_{α1}$ radiation. In some embodiments, the crystalline Form XII of Compound I can be characterized by an XRPD pattern further comprising at least one or more peaks at 6.0, 9.0, 10.9, 13.7, 17.1, 18.7, or 25.8 degrees 2θ (±0.2 degrees 2θ), wherein the XRPD is made using CuK$_{α1}$ radiation. In some embodiments, the crystalline Form XII of Compound I can be characterized by an XRPD pattern further comprising at least two or more peaks at 6.0, 9.0, 10.9, 13.7, 17.1, 18.7, or 25.8 degrees 2θ (±0.2 degrees 2θ), wherein the XRPD is made using CuK$_{α1}$ radiation. In some embodiments, the crystalline Form XII of Compound I can be characterized by an XRPD pattern further comprising at least three or more peaks at 6.0, 9.0, 10.9, 13.7, 17.1, 18.7, or 25.8 degrees 2θ (±0.2 degrees 2θ), wherein the XRPD is made using CuK$_{α1}$ radiation. In some embodiments, the crystalline Form XII of Compound I can be characterized by an XRPD pattern further comprising at least four or more peaks at 6.0, 9.0, 10.9, 13.7, 17.1, 18.7, or 25.8 degrees 2θ (±0.2 degrees 2θ), wherein the XRPD is made using CuK$_{α1}$ radiation. In some embodiments, the crystalline Form XII of Compound I can be characterized by an XRPD pattern further comprising at least five or more peaks at 6.0, 9.0, 10.9, 13.7, 17.1, 18.7, or 25.8 degrees 2θ (±0.2 degrees 2θ), wherein the XRPD is made using CuK$_{α1}$ radiation. In some embodiments, the crystalline Form XII of Compound I can be characterized by an XRPD pattern further comprising at least six or more peaks at 6.0, 9.0, 10.9, 13.7, 17.1, 18.7, or 25.8 degrees 2θ (±0.2 degrees 2θ), wherein the XRPD is made using CuK$_{α1}$ radiation.

Figure 28:
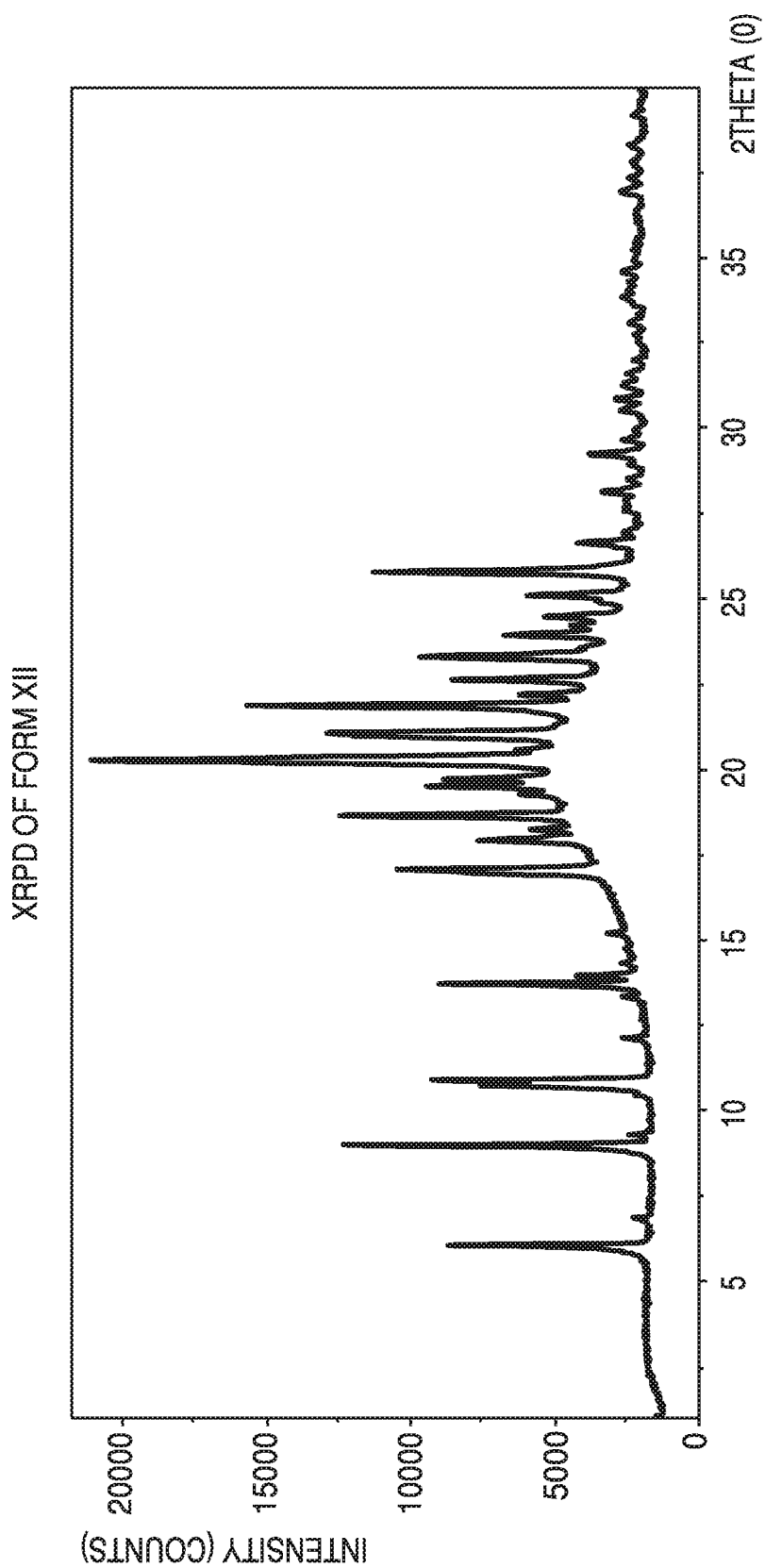
FIG. 28 shows an X-ray powder diffraction pattern of Compound I Form XII.
Figure 30:
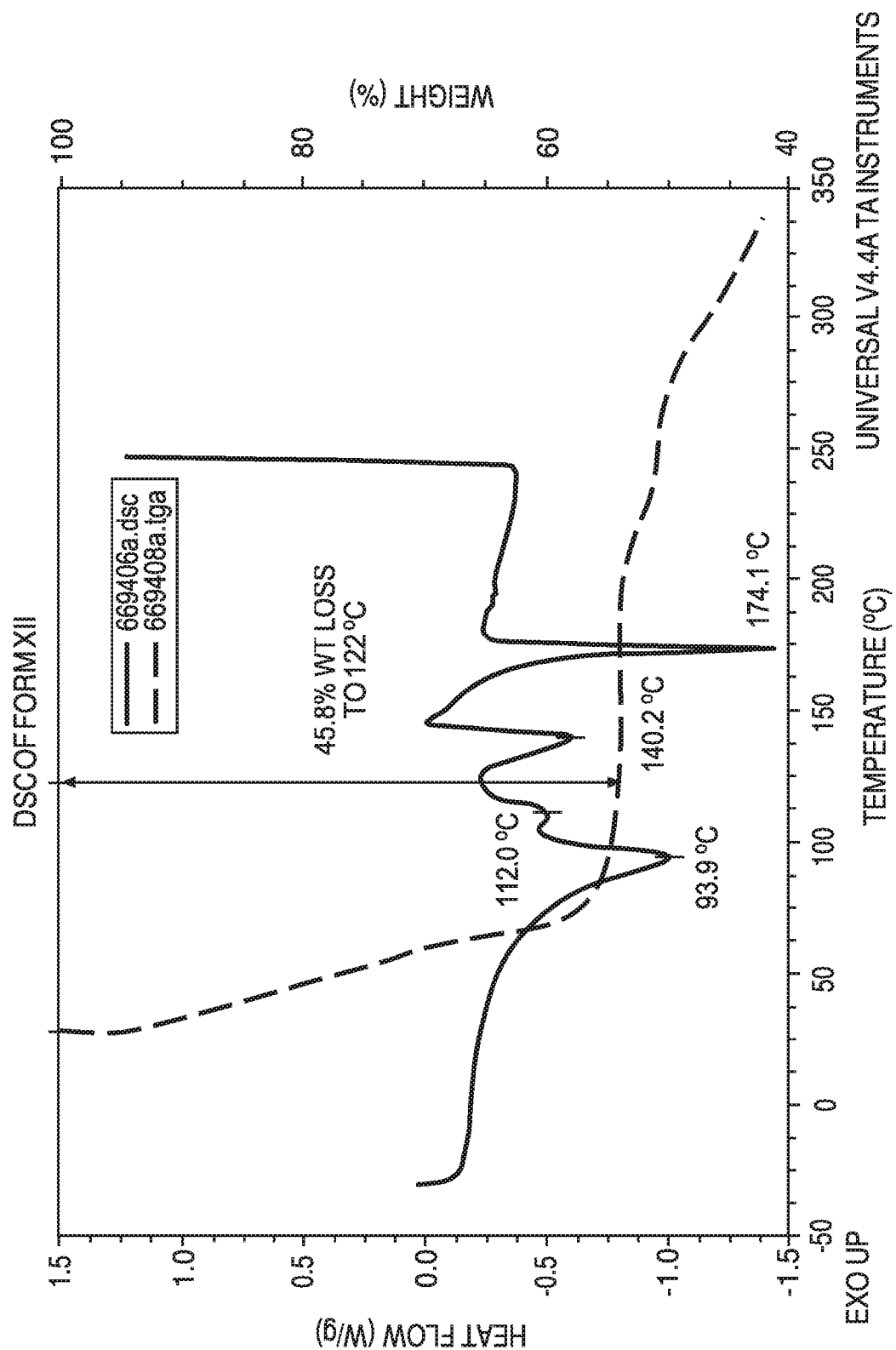
FIG. 30 shows a differential scanning calorimetry plot of Compound I Form XII.

In some embodiments, the crystalline Form XII of Compound I can be characterized by an XRPD pattern having peaks at 6.0, 9.0, 10.9, 13.7, 17.1, 18.7, 20.3, 21.1, 21.9, and 25.8 degrees 2θ (±0.2 degrees 2θ), wherein the XRPD is made using CuK$_{α1}$ radiation. In some embodiments, the crystalline Form XII of Compound I can be characterized by the XRPD pattern substantially in accordance with that of FIG. 28. In some embodiments, the crystalline Form XII of Compound I can be substantially free of other crystalline forms of Compound I. In some embodiments, the crystalline Form XII of Compound I can be substantially free of Form I, Form II, Form III, Form IV, Form V, Form VI, Form VII, Form VIII, Form IX, Form X, Form XI, Form XIII, and Form XIV.

Form XII of Compound I can be characterized by a differential scanning calorimetry (DSC) plot having an endotherm at about 94° C., 112° C., 140° C. or about 174° C. In some embodiments, the crystalline Form XII of Compound I can be characterized by a differential scanning calorimetry (DSC) endotherm at about 94° C., 112° C., 140° C. or about 174° C. In some embodiments, the crystalline Form XII of Compound I can be characterized by a differential scanning calorimetry (DSC) endotherm at about 174° C. In some embodiments, the crystalline Form XII of Compound I can be characterized by a differential scanning calorimetry (DSC) endotherm at about 94° C., 112° C., 140° C. and about 174° C.

In some embodiments, the crystalline Form XII of Compound I can be characterized by an XRPD pattern having peaks at 6.0, 9.0, 10.9, 13.7, 17.1, 18.7, 20.3, 21.1, 21.9, or 25.8 degrees 2θ (±0.2 degrees 2θ), wherein the XRPD is made using CuK$_{α1}$ radiation, and a DSC endotherm at about 174° C.

The crystalline Form XII of Compound I can also have a solvate or hydrate form. In some embodiments, the crystalline Form XII of Compound I can be a solvate with trifluoroethanol (TFE).

Form XIII

Form XIII of Compound I can be characterized by an X-ray powder diffraction (XRPD) pattern having at least three, four, five, or more, peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an X-ray powder diffraction (XRPD) pattern having at least three peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an X-ray powder diffraction (XRPD) pattern having at least four peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an X-ray powder diffraction (XRPD) pattern having at least five peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation.

Form XIII of Compound I can also be characterized by an X-ray powder diffraction (XRPD) pattern having at least six, seven, eight, nine, or more, peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an X-ray powder diffraction (XRPD) pattern having at least six peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an X-ray powder diffraction (XRPD) pattern having at least seven peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an X-ray powder diffraction (XRPD) pattern having at least eight peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an X-ray powder diffraction (XRPD) pattern having at least nine peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation.

In some embodiments, the crystalline Form XIII of Compound I can be characterized by an XRPD pattern having three or more peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an X-ray powder diffraction (XRPD) pattern having peaks at 4.6, 9.2, 18.4 and 20.0 degrees 2θ (±0.2 degrees 2θ), wherein the XRPD is made using CuK$_{α1}$ radiation. In some embodiments, the crystalline Form XIII of Compound I can be characterized by an XRPD pattern further comprising one or more peaks at 8.9, 13.8, 15.8, 16.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an XRPD pattern further comprising two or more peaks at 8.9, 13.8, 15.8, 16.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an XRPD pattern further comprising three or more peaks at 8.9, 13.8, 15.8, 16.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an XRPD pattern further comprising four or more peaks at 8.9, 13.8, 15.8, 16.0, 23.1 or 26.9 degrees 2θ (±0.2 degrees 2θ), wherein the XRPD is made using CuK$_{α1}$ radiation. In some embodiments, the crystalline Form XIII of Compound I can be characterized by an XRPD pattern further comprising five or more peaks at 8.9, 13.8, 15.8, 16.0, 23.1 or 26.9 degrees 2θ (±0.2 degrees 2θ), wherein the XRPD is made using CuK$_{α1}$ radiation.

Figure 31:
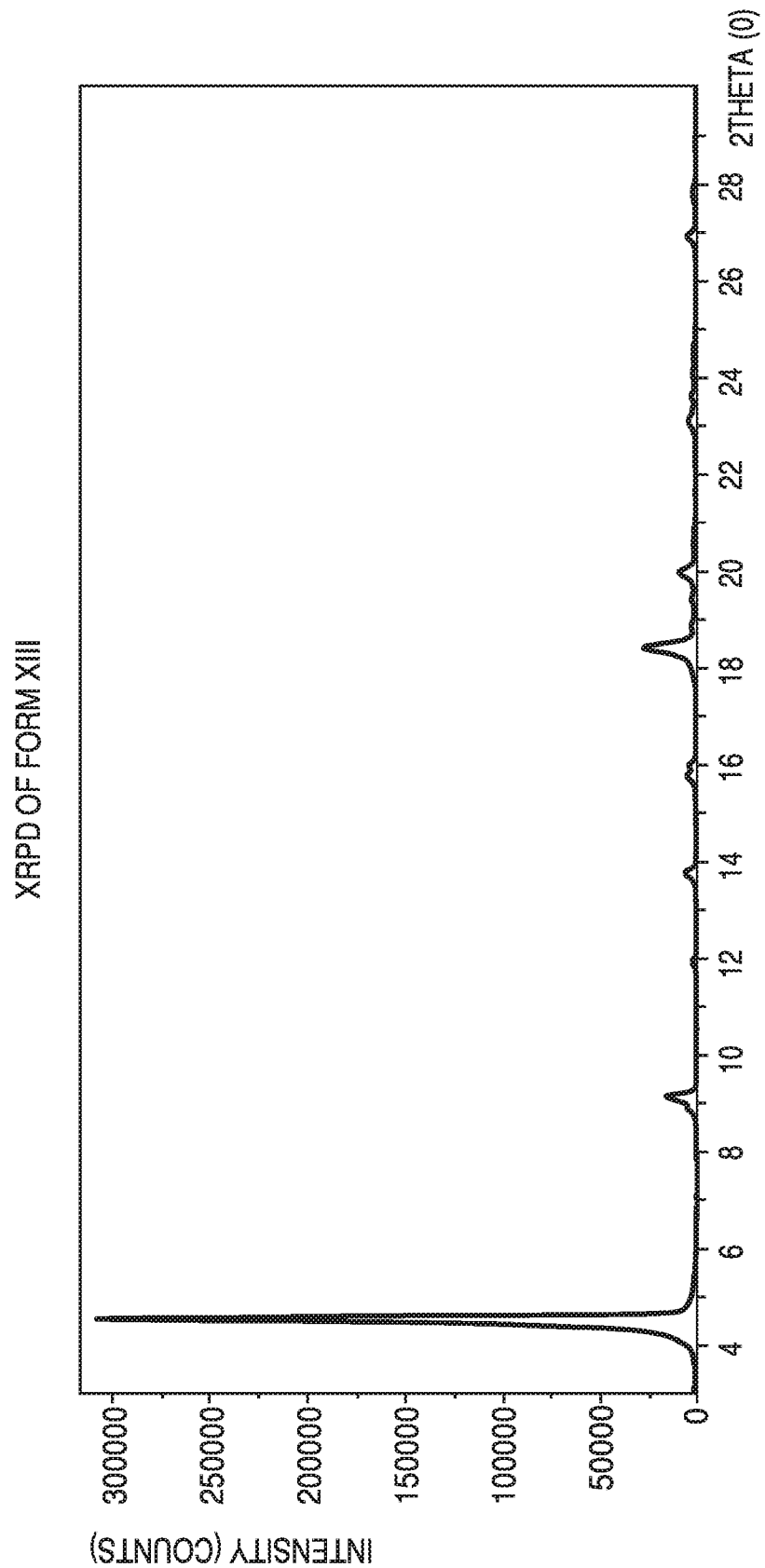
FIG. 31 shows an X-ray powder diffraction pattern of Compound I Form XIII.
Figure 33:
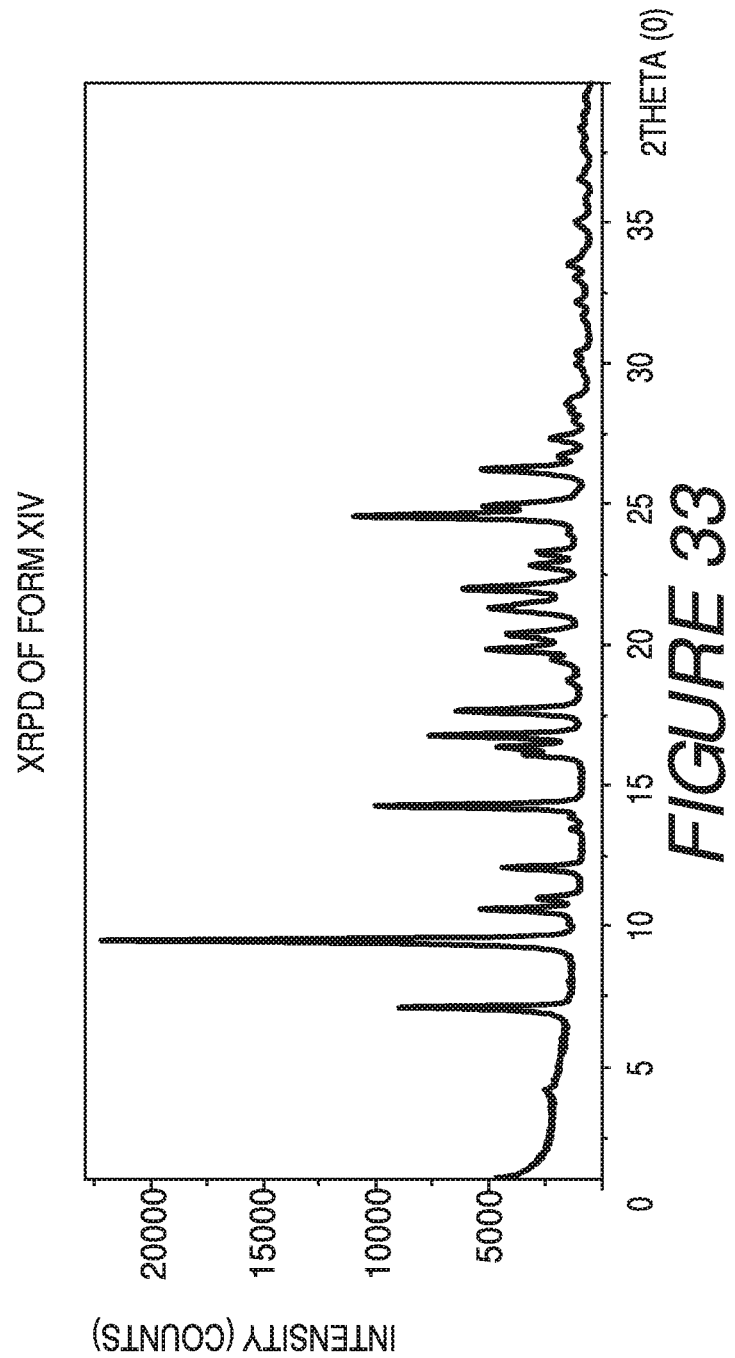
FIG. 33 shows an X-ray powder diffraction pattern of Compound I Form XIV.

In some embodiments, the crystalline Form XIII of Compound I can be characterized by an XRPD pattern having peaks at 4.6, 8.9, 9.2, 13.8, 15.8, 16.0, 18.4, 20.0, 23.1 or 26.9 degrees 2θ (±0.2 degrees 2θ), wherein the XRPD is made using CuK$_{α1}$ radiation. In some embodiments, the crystalline Form XIII of Compound I can be characterized by the XRPD pattern substantially in accordance with that of FIG. 31. In some embodiments, the crystalline Form XIII of Compound I can be substantially free of other crystalline forms of Compound I. In some embodiments, the crystalline Form XIII of Compound I can be substantially free of Form I, Form II, Form III, Form IV, Form V, Form VI, Form VII, Form VIII, Form IX, Form X, Form XI, Form XII, and Form XIV.

Form XIV

Form XIV of Compound I can be characterized by an X-ray powder diffraction (XRPD) pattern having at least three, four, five, or more, peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation. In some embodiments, the crystalline Form XIV of Compound I can be characterized by an X-ray powder diffraction (XRPD) pattern having at least three peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation. In some embodiments, the crystalline Form XIV of Compound I can be characterized by an X-ray powder diffraction (XRPD) pattern having at least four peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation. In some embodiments, the crystalline Form XIV of Compound I can be characterized by an X-ray powder diffraction (XRPD) pattern having at least five peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation.

Form XIV of Compound I can also be characterized by an X-ray powder diffraction (XRPD) pattern having at least six, seven, eight, nine, or more, peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation. In some embodiments, the crystalline Form XIV of Compound I can be characterized by an X-ray powder diffraction (XRPD) pattern having at least six peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation. In some embodiments, the crystalline Form XIV of Compound I can be characterized by an X-ray powder diffraction (XRPD) pattern having at least seven peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation. In some embodiments, the crystalline Form XIV of Compound I can be characterized by an X-ray powder diffraction (XRPD) pattern having at least eight peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation. In some embodiments, the crystalline Form XIV of Compound I can be characterized by an X-ray powder diffraction (XRPD) pattern having at least nine peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation.

In some embodiments, the crystalline Form XIV of Compound I can be characterized by an XRPD pattern having three or more peaks at 7.1, 9.5, 10.6, 14.3, 16.8, 17.6, 22.0, 24.6, 24.9 or 26.2 degrees 2θ (±0.2 degrees 2θ), wherein the XRPD is made using CuK$_{α1}$ radiation. In some embodiments, the crystalline Form XIV of Compound I can be characterized by an X-ray powder diffraction (XRPD) pattern having peaks at 7.1, 9.5, 14.3 and 24.6 degrees 2θ (±0.2 degrees 2θ), wherein the XRPD is made using CuK$_{α1}$ radiation. In some embodiments, the crystalline Form XIV of Compound I can be characterized by an XRPD pattern further comprising one or more peaks at 10.6, 16.8, 17.6, 22.0, 24.9 or 26.2 degrees 2θ (±0.2 degrees 2θ), wherein the XRPD is made using CuK$_{α1}$ radiation. In some embodiments, the crystalline Form XIV of Compound I can be characterized by an XRPD pattern further comprising two or more peaks at 10.6, 16.8, 17.6, 22.0, 24.9 or 26.2 degrees 2θ (±0.2 degrees 2θ), wherein the XRPD is made using CuK$_{α1}$ radiation. In some embodiments, the crystalline Form XIV of Compound I can be characterized by an XRPD pattern further comprising three or more peaks at 10.6, 16.8, 17.6, 22.0, 24.9 or 26.2 degrees 2θ (±0.2 degrees 2θ), wherein the XRPD is made using CuK$_{α1}$ radiation. In some embodiments, the crystalline Form XIV of Compound I can be characterized by an XRPD pattern further comprising four or more peaks at 10.6, 16.8, 17.6, 22.0, 24.9 or 26.2 degrees 2θ (±0.2 degrees 2θ), wherein the XRPD is made using CuK$_{α1}$ radiation. In some embodiments, the crystalline Form XIV of Compound I can be characterized by an XRPD pattern further comprising five or more peaks at 10.6, 16.8, 17.6, 22.0, 24.9 or 26.2 degrees 2θ (±0.2 degrees 2θ), wherein the XRPD is made using CuK$_{α1}$ radiation. In some embodiments, the crystalline Form XIV of Compound I can be characterized by an XRPD pattern further comprising six or more peaks at 10.6, 16.8, 17.6, 22.0, 24.9 or 26.2 degrees 2θ (±0.2 degrees 2θ), wherein the XRPD is made using CuK$_{α1}$ radiation.

In some embodiments, the crystalline Form XIV of Compound I can be characterized by an XRPD pattern having peaks at 7.1, 9.5, 10.6, 14.3, 16.8, 17.6, 22.0, 24.6, 24.9 and 26.2 degrees 2θ (±0.2 degrees 2θ), wherein the XRPD is made using CuK$_{α1}$ radiation. In some embodiments, the crystalline Form XIV of Compound I can be characterized by the XRPD pattern substantially in accordance with that of FIG. 28. In some embodiments, the crystalline Form XIV of Compound I can be substantially free of other crystalline forms of Compound I. In some embodiments, the crystalline Form XIV of Compound I can be substantially free of Form I, Form II, Form III, Form IV, Form V, Form VI, Form VII, Form VIII, Form IX, Form X, Form XI, Form XII, and Form XIII.

The crystalline Form XIV of Compound I can also have a solvate or hydrate form. In some embodiments, the crystalline Form XIV of Compound I can be a solvate with trifluoroethanol (TFE). In some embodiments, the crystalline Form XIV of Compound I can be a hydrate.

Any formula or structure given herein, including Compound I, is also intended to represent unlabeled forms as well as isotopically labeled forms of the compounds. Isotopically labeled compounds have structures depicted by the Formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}$H (deuterium, D), $^{3}$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^{3}$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes Compound I in which from 1 to "n" hydrogens attached to a carbon atom is/are replaced by deuterium, in which n is the number of hydrogens in the molecule. Such compounds exhibit increased resistance to metabolism and are thus useful for increasing the half-life of any Compound I when administered to a mammal. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent in Compound I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

IV. Methods of Preparing Solid Forms of Compound I

The solid forms of Compound I can be prepared by a variety of methods. For example, Compound I can be dissolved in a single solvent system and allowed to crystallize. Alternatively, Compound I can be crystallized from a two-solvent system by dissolving Compound I in a solvent, and then adding an anti-solvent to the mixture causing Compound I to crystallize.

The solvent can be any solvent suitable to form a solution. Typically the solvent can be a polar solvent, which in some embodiments is a protic solvent. Other suitable solvents include non-polar solvents. Suitable solvents include, but are not limited to, water, alkanes such as heptanes, hexanes, and cyclohexane, petroleum ether, $C_1$-$C_3$ alcohols (methanol, ethanol, propanol, isopropanol), ethylene glycol and polyethylene glycol such as PEG400, alkanoates such as ethyl acetate, propyl acetate, isopropyl acetate, and butyl acetate, acetonitrile, alkanones such as acetone, butanone, methyl ethyl ketone (MEK), methyl propyl ketone (MPK) and methyl iso-butyl ketone (MIBK), ethers such as diethyl ether, methyl-t-butyl ether, tetrahydrofuran, methyl-tetrahydrofuran, 1,2-dimethoxy ethane and 1,4-dioxane, aromatics such as benzene and toluene, halogenated solvents such as methylene chloride, chloroform and carbon tetrachloride, dimethylsulfoxide (DMSO), and dimethylformamide (DMF). Suitable solvents also include, but are not limited to halogenated $C_1$-$C_3$ alcohols (trifluoromethanol, trifluoroethanol (TFE), hexafluoroisopropanol (HFIPA)).

The methods of preparing crystalline forms of Compound I can be performed under any suitable reaction conditions. For example, the methods of preparing the crystalline forms of Compound I can be performed at any suitable temperature, such as, but not limited to, below room temperature, at room temperature, or above room temperature. In some embodiments, the temperature can be from about −78° C. to about 100° C., or from about 0° C. to about 50° C., or from about 10° C. to about 30° C. In some embodiments, the temperature can be the reflux temperature of the particular solvent used in the method. In other embodiments, crystalline forms of Compound I can be heated above about 100° C. such that one crystalline form of Compound I forms a second crystalline form of Compound I.

The methods of preparing crystalline forms of Compound I can be performed for any suitable time. For example, the time can be for minutes, hours or days. In some embodiments, the time can be several hours, such as overnight. The methods of preparing crystalline forms of Compound I can be also be performed at any suitable pressure. For example, the pressure can be below atmospheric pressure, at about atmospheric pressure, or above atmospheric pressure.

Form I

In some embodiments, the present invention provides a method of preparing a crystalline Form I of Compound I of the present invention, including forming a mixture of Compound I of the present invention, and a solvent, under conditions suitable to prepare Form I. Any suitable solvent can be used in the method of preparing Compound I Form I. In some embodiments, the solvent can be at least one of water, methanol, ethanol, isopropanol, methyl ethyl ketone, methyl iso-butyl ketone, acetonitrile, tetrahydrofuran, methyl-tetrahydrofuran, 1,2-dimethoxy ethane, ethyl acetate, 1,4-dioxane, or dichloromethane. In some embodiments, the solvent can be at least one of methanol, ethanol, isopropanol, or dichloromethane. In some embodiments, the solvent can include one of methanol, ethanol, or isopropanol. In some embodiments, the solvent can be at least one of methanol, ethanol, or isopropanol, in combination with dichloromethane. In some embodiments, the solvent can be methanol and dichloromethane.

In some embodiments, the present invention provides a method of preparing a crystalline Form I of Compound I by forming a mixture of Compound I, and a solvent including a $C_1$-$C_3$ alcohol and dichloromethane, under conditions suitable to prepare Form I. The $C_1$-$C_3$ alcohol can be methanol, ethanol, propanol or isopropanol. In some embodiments, the solvent includes one of methanol, ethanol or isopropanol. In some embodiments, the solvent includes methanol and dichloromethane. In some embodiments, the solvent includes ethanol and dichloromethane. In some embodiments, the solvent includes isopropanol and dichloromethane.

Any suitable ratio of the methanol and dichloromethane can be used. For example, the ratio of methanol and dichloromethane can be from 10:1 to about 1:10 (volume/volume), including about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or about 1:10 (volume/volume). In some embodiments, the ratio of methanol to dichloromethane can be from about 1:1 to about 1:5 (volume/volume). In some embodiments, the ratio of methanol to dichloromethane can be about 1:2 (volume/volume).

The method of preparing Form I of Compound I can include a variety of other steps. For example, the solvent can be evaporated, a seed crystal can be added to the mixture, the mixture can be heated and cooled a single time or repeatedly, etc. In some embodiments, the method of preparing Form I of Compound I also includes evaporating the solvent, thereby forming Form I. In some embodiments, the method of preparing Form I of Compound I includes forming a reaction mixture of Compound I, methanol and dichloromethane, wherein the ratio of methanol to dichloromethane is 1:2 (volume/volume), and removing the dichloromethane, thereby forming crystalline Form I of Compound I.

Form II

The present invention also provides methods for preparing Compound I Form II. In some embodiments, the present invention provides a method of preparing a crystalline Form II of Compound I by forming a mixture of Compound I and chloroform, under conditions suitable to prepare Form II. The conditions for preparing crystalline Form II of Compound I can include ambient temperature and pressure for a period of time of at least 1 day. The period of time for preparing crystalline Form II of Compound I can also be for at least 2, 3, 4, 5, or more days. In some embodiments, the method for preparing the crystalline Form II of Compound I can be for about 5 days.

Form III

The present invention also provides methods for preparing Compound I Form III. In some embodiments, the present invention provides a method of preparing a crystalline Form III of Compound I by heating a Form I of Compound I to a temperature of from about 130° C. to about 190° C., thereby forming Form III. In some embodiments, the method also includes cooling Form III to room temperature.

Form IV

The present invention also provides methods for preparing Compound I Form IV. In some embodiments, the present invention provides a method of preparing a crystalline Form IV of Compound I by heating a Form II of Compound I to a temperature of from about 90° C. to about 250° C., thereby forming Form IV.

Form V

The present invention also provides methods for preparing Compound I Form V. In some embodiments, the present invention provides a method of preparing a crystalline Form V of Compound I by forming a mixture of Compound I and hexafluoroisopropanol, and removing the hexafluoroisopropanol, under conditions suitable to prepare Form V. The hexafluoroisopropanol can be removed under any suitable conditions such as via vacuum, heating, or a combination of the two. Alternatively, Form V can be formed by combining a hot solution of Compound I with cold water and isolating the subsequent solid.

Form VI

The present invention also provides methods for preparing Compound I Form VI. In some embodiments, the present invention provides a method of preparing a crystalline Form VI of Compound I by forming a mixture of Compound I and trifluoroethanol, and removing the trifluoroethanol, under conditions suitable to prepare Form VI. The trifluoroethanol can be removed under any suitable conditions such as via vacuum, heating, or a combination of the two.

Form VII

The present invention also provides methods for preparing Compound I Form VII. In some embodiments, the present invention provides a method of preparing a crystalline Form VII of Compound I by forming a mixture of Compound I and trifluoroethanol, and removing the trifluoroethanol, under conditions suitable to prepare Form VII. The trifluoroethanol can be removed under any suitable conditions such as via vacuum, heating, or a combination of the two.

Form VIII

The present invention also provides methods for preparing Compound I Form VIII. In some embodiments, the present invention provides a method of preparing a crystalline Form VIII of Compound I by exposing Compound I Form V or Form VII to an atmosphere with a relative humidity greater than about 90%, under conditions suitable to prepare Form VIII. The relative humidity can be any suitable humidity, such as greater than about 50%, 55, 60, 65, 70, 75, 80, 85, 90, 91, 92, 93, 94, 95, 96, 97, 98 or greater than about 99%. In some embodiments, the relative humidity can be greater than about 95%. In some embodiments, the relative humidity can be about 97%.

Form IX

The present invention also provides methods for preparing Compound I Form IX. In some embodiments, the present invention provides a method of preparing a crystalline Form IX of Compound I by forming a mixture of a Form I of Compound I, water and trifluoroethanol, under conditions suitable to prepare Form IX. Any suitable ratio of the trifluoroethanol and water can be used. For example, the ratio of trifluoroethanol to water can be from 10:1 to about 1:1 (volume/volume), including about 10:1, 9:1, 8:1, 7:1, 6:1, 5:1, 4:1, 3:1, 2:1 or about 1:1 (volume/volume). In some embodiments, the ratio of trifluoroethanol to water can be from about 10:1 to about 1:1 (volume/volume). In some embodiments, the ratio of trifluoroethanol to water can be about 5:1 (volume/volume). The conditions for preparing crystalline Form IX of Compound I can include ambient temperature and pressure for a period of time of at least 1 day. The period of time for preparing crystalline Form IX of Compound I can also be for at least 2, 3, 4, 5, or more days. In some embodiments, the method for preparing the crystalline Form IX of Compound I can be for about 5 days.

Form X

The present invention also provides methods for preparing Compound I Form X. In some embodiments, the present invention provides a method of preparing a crystalline Form X of Compound I by forming a mixture of a Form I of Compound I and chloroform, under conditions suitable to prepare Form X. The suitable conditions for preparing the crystalline Form X of Compound I can include ambient temperature and pressure.

Form XI

The present invention also provides methods for preparing Compound I Form XI. In some embodiments, the present invention provides a method of preparing a crystalline Form XI of Compound I by forming a mixture of a Form I of Compound I and hexafluoroisopropanol, under conditions suitable to prepare Form XI.

Form XII

The present invention also provides methods for preparing Compound I Form XII. In some embodiments, the present invention provides a method of preparing a crystalline Form XII of Compound I by forming a mixture of a Form I of Compound I, water and trifluoroethanol, under conditions suitable to prepare Form XII. Any suitable ratio of the trifluoroethanol and water can be used. For example, the ratio of trifluoroethanol to water can be from 20:1 to about 1:1 (volume/volume), including about 20:1, 19:1, 18:1, 17:1, 16:1, 15:1, 14:1, 13:1, 12:1, 10:1, 9:1, 8:1, 7:1, 6:1, 5:1, 4:1, 3:1, 2:1 or about 1:1 (volume/volume). In some embodiments, the ratio of trifluoroethanol to water can be from about 20:1 to about 1:1 (volume/volume). In some embodiments, the ratio of trifluoroethanol to water can be from about 15:1 to about 5:1 (volume/volume). In some embodiments, the ratio of trifluoroethanol to water can be about 10:1 (volume/volume).

Form XIII

The present invention also provides methods for preparing Compound I Form XIII. In some embodiments, the present invention provides a method of preparing a crystalline Form XIII of Compound I by cooling Form II of Compound I to less than 0° C., under conditions suitable to prepare Form XIII. Form II of Compound I can be cooled to any suitable temperature less than 0° C., including, but not limited to, −5° C., −10, −15, −20, −25, −30, −40, −50, −60 and −70° C. In some embodiments, Form II of Compound I can be cooled to about −10° C. to prepare Form XIII.

Form XIV

The present invention also provides methods for preparing Compound I Form XIV. In some embodiments, the present invention provides a method of preparing a crystalline Form XIV of Compound I by drying Form XII under conditions suitable to prepare Form XIV. The drying can include heating Form XII to a suitable temperature for a suitable period of time, placing Form XII in a reduced atmosphere environment, or both. For example, Form XII can be heated to a temperature above room temperature, such as 30° C., 35, 40, 45, 50, 55, 60, 65, 70, 75, 80, 90, or 100° C. When Form XII is dried in a reduced atmosphere environment, the reduced atmosphere can have any suitable pressure less than 1 atmosphere, such as 0.9 atm, 0.8, 0.7, 0.6, 0.5, 0.4, 0.3, 0.2, 0.1, 0.05, 0.01, 0.005, 0.001 atm, or less. In some embodiments, preparing Form XIV includes drying Form XII at a pressure less than 1 atmosphere. In some embodiments, preparing Form XIV includes heating Form XII. In some embodiments, preparing Form XIV including drying Form XII at a pressure less than 1 atmosphere, and heating Form XII at a temperature of about 40° C.

The method of preparing crystalline Compound I can be carried out at temperatures generally from about 0° C. to the reflux temperature of the solvent. In some embodiments, the temperature can be room temperature. Alternatively, Compound I, or one of the crystalline forms of Compound I, can be heated in solid state form. For example, Compound I Form I can be heated to a temperature of from about 130° C. to about 200° C., or from about 130° C. to about 150° C. Compound I Form II can be heated to a temperature of from about 90° C. to about 200° C.

When multiple solvents are used in the methods of the present invention, the ratio of solvents in the above methods can be any suitable ratio from about 1:1 to about 1:9, including about 1:2, 1:3, 1:4, 1:5, 1:6, 1:7 and about 1:8 by volume. The range of solvent ratios is preferably from about 1:1 to about 1:9, more preferably from about 1:2 to about 1:7, even more preferably from about 1:2 to about 1:5 by volume.

The ratio of Compound I to solvent, can be any suitable ratio to promote crystallization. For example, the Compound I to solvent ratio can be from about 1:5 (weight/volume, or w/v) to about 1:50 (w/v), including about 1:6, 1:7, 1:8, 1:9, 1:10, 1:11, 1:12, 1:13, 1:14, 1:15, 1:20, 1:25, 1:30, 1:35, 1:40 and about 1:45 (w/v). The Compound I to solvent ratio is preferably from about 1:10 to about 1:25 (w/v), more preferably from about 1:10 to about 1:15 (w/v).

Crystallization can be induced by methods known in the art, for example by mechanical means such as scratching or rubbing the contact surface of the reaction vessel with e.g. a glass rod. Optionally the saturated or supersaturated solution may be inoculated with seed crystals. The mixture for crystallizing Compound I can also contain a seed crystal of crystalline Compound I.

Isolation of the desired crystalline form can be accomplished by removing the solvent and precipitating solvent from the crystals. Generally this is carried out by known methods, such as, filtration, suction filtration, decantation or centrifugation. Further isolation can be achieved by removing any excess of the solvent(s) from the crystalline form by methods known to the one skilled in the art as for example application of a vacuum, and/or by heating.

V. Pharmaceutical Compositions

The solid forms of Compound I provided herein can be administered in the form of pharmaceutical compositions. This disclosure provides pharmaceutical compositions that contain, as the active ingredient, one or more of the solid forms of Compound I described or a pharmaceutically acceptable salt or ester thereof and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents (as indicated in the Combination Therapy section below). Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously orally, topically, as an inhalant or via an impregnated or coated device such as a stent, for example or an artery-inserted cylindrical polymer.

One mode for administration is parenteral, particularly by injection. The forms in which the novel compositions of the present disclosure may be incorporated for administration by injection include aqueous or oil suspensions or emulsions, with sesame oil, corn oil, cottonseed oil or peanut oil, as well as elixirs, mannitol, dextrose or a sterile aqueous solution and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the general methods of preparation are vacuum-drying and freeze-drying techniques which yield a powder of the active ingredient plus any additional desired ingredient from a previously sterile-filtered solution thereof.

Oral administration is another route for administration of compounds in accordance with the disclosure. Administration may be via capsule or enteric coated tablets or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include: lubricating agents such as talc, magnesium stearate and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile or on demand delivery of pharmaceutical agents.

In some embodiments, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, each dosage unit contains from 1 mg to 2 g of a compound described herein and for parenteral administration, in some embodiments, from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation include solutions and suspensions in pharmaceutically acceptable, aqueous or organic solvents or mixtures thereof and powders. The liquid or solid compositions may contain suitable pharmaceutically acceptable excipients as described supra. In some embodiments, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent or intermittent positive pressure breathing machine. Solution, suspension or powder compositions may be administered, in some embodiments orally or nasally, from devices that deliver the formulation in an appropriate manner.

In one embodiment, this disclosure relates to a pharmaceutical composition comprising a pharmaceutically acceptable excipient or carrier and a therapeutically effective amount of the compound of Compound I as described above or a pharmaceutically acceptable salt, ester, prodrug, stereoisomer or hydrate thereof.

VI. Methods of Use

The solid forms of Compound I described herein can be administered to a subject suffering from a viral infection such as, but not limited to, hepatitis B virus (HBV), hepatitis C virus (HCV), and human immuno-deficiency virus (HIV) in either single or multiple doses by any of the accepted modes of administration known to those who are skilled in the art and as detailed above.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor.

As will be appreciated by those skilled in the art, when treating a viral infection such as HCV, HBV, or HIV, such treatment may be characterized in a variety of ways and measured by a variety of endpoints. The scope of the present invention is intended to encompass all such characterizations.

In one embodiment, the method can be used to induce an immune response against multiple epitopes of a viral infection in a human. Induction of an immune response against viral infection can be assessed using any technique that is known by those of skill in the art for determining whether an immune response has occurred. Suitable methods of detecting an immune response for the present invention include, among others, detecting a decrease in viral load or antigen in a subject's serum, detection of IFN-gamma-secreting peptide specific T cells, and detection of elevated levels of one or more liver enzymes, such as alanine transferase (ALT) and aspartate transferase (AST). In one embodiment, the detection of IFN-gamma-secreting peptide specific T cells is accomplished using an ELISPOT assay. Another embodiment includes reducing the viral load associated with HBV infection, including a reduction as measured by PCR testing.

In some embodiments, the present invention provides a method of treating a viral infection, comprising administering to a human in need thereof, a therapeutically effective amount of a crystalline form of Compound I or pharmaceutical composition of the present invention. In some embodiments, the present invention provides a crystalline form of Compound I for use in the treatment of a viral infection, comprising administering a therapeutically effective amount of a crystalline form of Compound I or a pharmaceutical composition of the present invention. In some embodiments, the present invention provides use of a crystalline form of Compound I for the treatment of a viral infection. In some embodiments, the present invention provides use of a crystalline form of Compound I for the manufacture of a medicament for the treatment of a viral infection.

In another aspect, the present invention provides methods for treating a hepatitis B viral infection or a hepatitis C viral infection, wherein each of the methods includes the step of administering to a human subject infected with hepatitis B virus or hepatitis C virus a therapeutically effective amount of a crystalline form of Compound I. Typically, the human subject is suffering from a chronic hepatitis B infection or a chronic hepatitis C infection, although it is within the scope of the present invention to treat people who are acutely infected with HBV or HCV.

In some embodiments, the present invention provides a crystalline form of Compound I for use in the treatment of a hepatitis B viral infection or a hepatitis C viral infection. In some embodiments, the present invention provides use of a crystalline form of Compound I for the manufacture of a medicament for the treatment of a hepatitis B viral infection or a hepatitis C viral infection.

In some embodiments, the present invention provides a crystalline form of Compound I for use in the treatment of a hepatitis B viral infection. In some embodiments, the present invention provides use of a crystalline form of Compound I for the manufacture of a medicament for the treatment of a hepatitis B viral infection.

Treatment in accordance with the present invention typically results in the stimulation of an immune response against HBV or HCV in a human being infected with HBV or HCV, respectively, and a consequent reduction in the viral load of HBV or HCV in the infected person. Examples of immune responses include production of antibodies (e.g., IgG antibodies) and/or production of cytokines, such as interferons, that modulate the activity of the immune system. The immune system response can be a newly induced response, or can be boosting of an existing immune response. In particular, the immune system response can be seroconversion against one or more HBV or HCV antigens.

The viral load can be determined by measuring the amount of HBV DNA or HCV DNA present in the blood. For example, blood serum HBV DNA can be quantified using the Roche COBAS Amplicor Monitor PCR assay (version 2.0; lower limit of quantification, 300 copies/mL [57 IU/mL]) and the Quantiplex bDNA assay (lower limit of quantification, 0.7 MEq/mL; Bayer Diagnostics, formerly Chiron Diagnostics, Emeryville, Calif.). The amount of antibodies against specific HBV or HCV antigens (e.g., hepatitis B surface antigen (HBsAG)) can be measured using such art-recognized techniques as enzyme-linked immunoassays and enzyme-linked immunoabsorbent assays. For example, the amount of antibodies against specific HBV or HCV antigens can be measured using the Abbott AxSYM microparticle enzyme immunoassay system (Abbott Laboratories, North Chicago, Ill.).

Compound I can be administered by any useful route and means, such as by oral or parenteral (e.g., intravenous) administration. Therapeutically effective amounts of Compound I are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 µg to about 30 mg per day, or such as from about 30 µg to about 300 µg per day.

Therapeutically effective amounts of Compound I are also from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of Compound I are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of Compound I are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks.

A single dose can also be administered once every month. The frequency of dosage of Compound I will be determined by the needs of the individual patient and can be, for example, once per day or twice, or more times, per day.

Administration of Compound I continues for as long as necessary to treat the HBV or HCV infection. For example, Compound I can be administered to a human being infected with HBV or HCV for a period of from 20 days to 180 days or, for example, for a period of from 20 days to 90 days or, for example, for a period of from 30 days to 60 days.

Administration can be intermittent, with a period of several or more days during which a patient receives a daily dose of Compound I, followed by a period of several or more days during which a patient does not receive a daily dose of Compound I. For example, a patient can receive a dose of Compound I every other day, or three times per week. Again by way of example, a patient can receive a dose of Compound I each day for a period of from 1 to 14 days, followed by a period of 7 to 21 days during which the patient does not receive a dose of Compound I, followed by a subsequent period (e.g., from 1 to 14 days) during which the patient again receives a daily dose of Compound I. Alternating periods of administration of Compound I, followed by non-administration of Compound I, can be repeated as clinically required to treat the patient.

As described more fully herein, crystalline forms of Compound I can be administered with one or more additional therapeutic agent(s) to a human being infected with hepatitis B virus or hepatitis C virus. The additional therapeutic agent(s) can be administered to the infected human being at the same time as the crystalline form of Compound I, or before or after administration of the crystalline form of Compound I. In some embodiments, the present invention provides a crystalline form of Compound I, for use in a method of treating or preventing a hepatitis B viral infection, wherein the crystalline form of Compound I is administered simultaneously, separately or sequentially with one or more additional therapeutic agents for treating a hepatitis B viral infection. In some embodiments, the present invention provides use of a crystalline form of Compound I for the manufacture of a medicament for the treatment of a hepatitis B viral infection, wherein the crystalline form of Compound I is administered simultaneously, separately or sequentially with one or more additional therapeutic agents for treating a hepatitis B viral infection.

In another aspect, the present invention provides a method for ameliorating a symptom associated with an HBV infection or HCV infection, wherein the method comprises administering to a human subject infected with hepatitis B virus or hepatitis C virus a therapeutically effective amount of the crystalline form of Compound I, wherein the therapeutically effective amount is sufficient to ameliorate a symptom associated with the HBV infection or HCV infection. Such symptoms include the presence of HBV virus particles (or HCV virus particles) in the blood, liver inflammation, jaundice, muscle aches, weakness and tiredness.

In some embodiments, the present invention provides a crystalline form of Compound I for use in ameliorating a symptom associated with an HBV infection or HCV infection, wherein the method comprises administering to a human subject infected with hepatitis B virus or hepatitis C virus a therapeutically effective amount of the crystalline form of Compound I, wherein the therapeutically effective amount is sufficient to ameliorate a symptom associated with the HBV infection or HCV infection. In some embodiments, the present invention provides use of a crystalline form of Compound I for the manufacture of a medicament for the ameliorating a symptom associated with an HBV infection or HCV infection, wherein the method comprises administering to a human subject infected with hepatitis B virus or hepatitis C virus a therapeutically effective amount of the crystalline form of Compound I, wherein the therapeutically effective amount is sufficient to ameliorate a symptom associated with the HBV infection or HCV infection In a further aspect, the present invention provides a method for reducing the rate of progression of a hepatitis B viral infection, or a hepatitis C virus infection, in a human being, wherein the method comprises administering to a human subject infected with hepatitis B virus or hepatitis C virus a therapeutically effective amount of Compound I, or a pharmaceutically acceptable salt thereof, wherein the therapeutically effective amount is sufficient to reduce the rate of progression of the hepatitis B viral infection or hepatitis C viral infection. The rate of progression of the infection can be followed by measuring the amount of HBV virus particles or HCV virus particles in the blood.

In another aspect, the present invention provides a method for reducing the viral load associated with HBV infection or HCV infection, wherein the method comprises administering to a human being infected with HBV or HCV a therapeutically effective amount of Compound I, or a pharmaceutically acceptable salt thereof, wherein the therapeutically effective amount is sufficient to reduce the HBV viral load or the HCV viral load in the human being.

In a further aspect, the present invention provides a method of inducing or boosting an immune response against Hepatitis B virus or Hepatitis C virus in a human being, wherein the method comprises administering a therapeutically effective amount of Compound I, or a pharmaceutically acceptable salt thereof, to the human being, wherein a new immune response against Hepatitis B virus or Hepatitis C virus is induced in the human being, or a preexisting immune response against Hepatitis B virus or Hepatitis C virus is boosted in the human being. Seroconversion with respect to HBV or HCV can be induced in the human being. Examples of immune responses include production of antibodies, such as IgG antibody molecules, and/or production of cytokine molecules that modulate the activity of one or more components of the human immune system.

Induction of seroconversion against HCV or HBV in patients chronically infected with either of these viruses is an unexpected property of Compound I. In clinical practice, an HBV patient, or HCV patient, is treated with Compound I, alone or in combination with one or more other therapeutic agents, until an immune response against HBV or HCV is induced or enhanced and the viral load of HBV or HCV is reduced. Thereafter, although the HBV or HCV virus may persist in a latent form in the patient's body, treatment with Compound I can be stopped, and the patient's own immune system is capable of suppressing further viral replication. In patients treated in accordance with the present invention and who are already receiving treatment with an antiviral agent that suppresses replication of the HBV virus or HCV virus, there may be little or no detectable viral particles in the body of the patient during treatment with the antiviral agent(s). In these patients, seroconversion will be evident when the antiviral agent(s) is no longer administered to the patient and there is no increase in the viral load of HBV or HCV.

In the practice of the present invention, an immune response is induced against one or more antigens of HBV or HCV. For example, an immune response can be induced against the HBV surface antigen (HBsAg), or against the small form of the HBV surface antigen (small S antigen), or against the medium form of the HBV surface antigen (medium S antigen), or against a combination thereof. Again by way of example, an immune response can be induced against the HBV surface antigen (HBsAg) and also against other HBV-derived antigens, such as the core polymerase or x-protein.

Induction of an immune response against HCV or HBV can be assessed using any technique that is known by those of skill in the art for determining whether an immune response has occurred. Suitable methods of detecting an immune response for the present invention include, among others, detecting a decrease in viral load in a subject's serum, such as by measuring the amount of HBV DNA or HCV DNA in a subject's blood using a PCR assay, and/or by measuring the amount of anti-HBV antibodies, or anti-HCV antibodies, in the subject's blood using a method such as an ELISA.

Additionally, the compounds of this invention may be useful in the treatment of cancer or tumors (including dysplasias, such as uterine dysplasia). These includes hematological malignancies, oral carcinomas (for example of the lip, tongue or pharynx), digestive organs (for example esophagus, stomach, small intestine, colon, large intestine, or rectum), liver and biliary passages, pancreas, respiratory system such as larynx or lung (small cell and non-small cell), bone, connective tissue, skin (e.g., melanoma), breast, reproductive organs (uterus, cervix, testicles, ovary, or prostate), urinary tract (e.g., bladder or kidney), brain and endocrine glands such as the thyroid. In summary, the compounds of this invention are employed to treat any neoplasm, including not only hematologic malignancies but also solid tumors of all kinds.

Hematological malignancies are broadly defined as proliferative disorders of blood cells and/or their progenitors, in which these cells proliferate in an uncontrolled manner. Anatomically, the hematologic malignancies are divided into two primary groups: lymphomas—malignant masses of lymphoid cells, primarily but not exclusively in lymph nodes, and leukemias—neoplasm derived typically from lymphoid or myeloid cells and primarily affecting the bone marrow and peripheral blood. The lymphomas can be subdivided into Hodgkin's Disease and Non-Hodgkin's lymphoma (NHL). The latter group comprises several distinct entities, which can be distinguished clinically (e.g. aggressive lymphoma, indolent lymphoma), histologically (e.g. follicular lymphoma, mantle cell lymphoma) or based on the origin of the malignant cell (e.g. B lymphocyte, T lymphocyte). Leukemias and related malignancies include acute myelogenous leukemia (AML), chronic myelogenous leukemia (CML), acute lymphoblastic leukemia (ALL) and chronic lymphocytic leukemia (CLL). Other hematological malignancies include the plasma cell dyscrasias including multiple myeloma, and the myelodysplastic syndromes.

VII. Combination Therapy

Subjects being treated by administration of the solid forms of Compound I described herein can benefit from treatment with additional therapeutic agents that are effective in treating HCV, or enhance the anti-HCV therapeutic effect of Compound I forms, in accordance with some embodiments. Additional therapeutic agents that may be useful for this purpose include, but are not limited to, ribavirin,

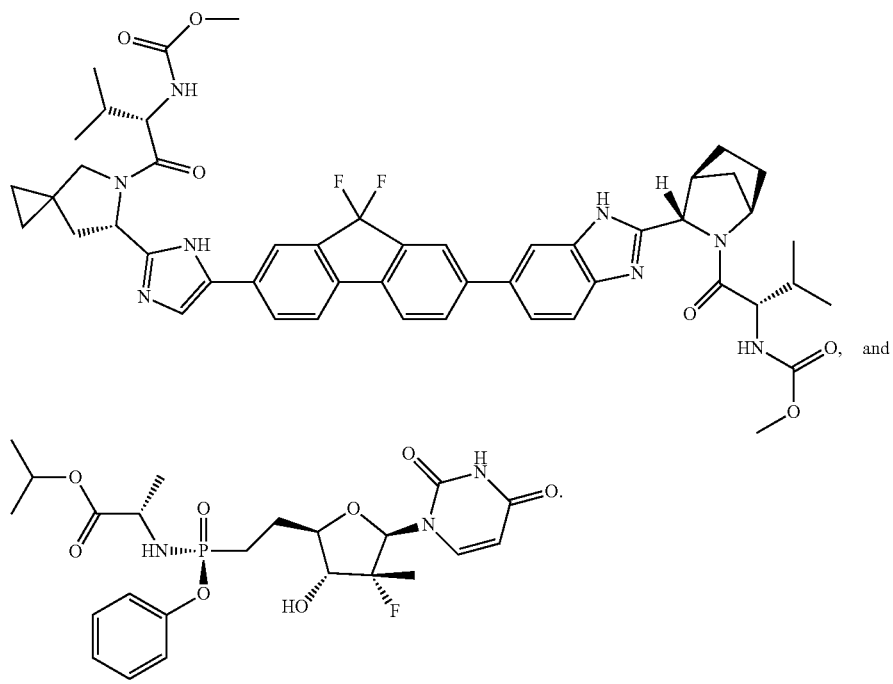

Other antiviral agents that may be useful in combination with the crystalline forms of Compound I of the present invention, include, but are not limited to: HCV NS3 protease inhibitors (see EP 1881001, US 2003187018, US 2005267018, WO 2003006490, WO 200364456, WO 2004094452, WO 2005028502, WO 2005037214, WO 2005095403, WO 2007014920, WO 2007014921, WO 2007014922, WO 2007014925, WO 2007014926, WO 2007015824, WO 2008010921, and WO 2008010921); HCV NS5B Inhibitors (see US 2004229840, US 2005154056, US 2005-98125, US 20060194749, US 20060241064, US 20060293306, US 2006040890, US 2006040927, US 2006166964, US 2007275947, U.S. Pat. No. 6,784,166, US20072759300, WO 2002057287, WO 2002057425, WO 2003010141, WO 2003037895, WO 2003105770, WO 2004000858, WO 2004002940, WO 2004002944, WO 2004002977, WO 2004003138, WO 2004041201, WO 2004065367, WO 2004096210, WO 2005021568, WO 2005103045, WO 2005123087, WO 2006012078, WO 2006020082, WO 2006065335, WO 2006065590, WO 2006093801, WO 200702602, WO 2007039142, WO 2007039145, WO 2007076034, WO 2007088148, WO 2007092000, and WO2007095269); HCV NS4 Inhibitors (see WO 2005067900 and WO 2007070556); HCV NS5a Inhibitors (see US 2006276511, WO 2006035061, WO 2006100310, WO 2006120251, and WO 2006120252); Toll-like receptor agonists (see WO 2007093901); other inhibitors (see WO 2000006529, WO 2003101993, WO 2004009020, WO 2004014313, WO 2004014852, and WO 2004035571); U.S. Pat. No. 7,429,572; US 2007/0197463; US 2010/0081628; US 2010/0016251; U.S. Ser. No. 12/783,680; telaprevir (also known as VX-950, which is disclosed in US 2010/0015090); boceprevir (disclosed in US 2006/0276405); BMS-790052 (disclosed in WO 2008/021927); ITMN-191 (disclosed in US 2009/0269305 at Example 62-1); ANA-598 (identified as compound 31 in F. Ruebasam et al. Biorg. Med. Chem. Lett. (2008) 18: 3616-3621; and TMC435 (formerly known as TMC435350); as well as, interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor.

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence.

In certain embodiments, a method for treating or preventing an HBV infection in a human having or at risk of having the infection is provided, comprising administering to the human a therapeutically effective amount of a compound disclosed herein (e.g. any crystalline form of Compound I), in combination with a therapeutically effective amount of one or more (e.g., one, two, three, four, one or two, or one to three, or one to four) additional therapeutic agents. In one embodiment, a method for treating an HBV infection in a human having or at risk of having the infection is provided, comprising administering to the human a therapeutically effective amount of a compound disclosed herein (e.g. any crystalline form of Compound I), in combination with a therapeutically effective amount of one or more (e.g., one, two, three, four, one or two, or one to three, or one to four) additional therapeutic agents.

In certain embodiments, the present disclosure provides a method for treating an HBV infection, comprising administering to a patient in need thereof a therapeutically effective amount of a compound disclosed herein (e.g. any crystalline form of Compound I), in combination with a therapeutically effective amount of one or more additional therapeutic agents which are suitable for treating an HBV infection.

In certain embodiments, a compound as disclosed herein (e.g., any crystalline form of Compound I) may be combined with one or more additional therapeutic agents in any dosage amount of the crystalline form of Compound I (e.g., from 1 mg to 1000 mg of compound).

In one embodiment, pharmaceutical compositions comprising a compound disclosed herein (e.g. any crystalline form of Compound I), in combination with one or more (e.g., one, two, three, four, one or two, or one to three, or one to four) additional therapeutic agents, and a pharmaceutically acceptable carrier, diluent or excipient are provided.

In one embodiment, kits comprising a compound disclosed herein (e.g. any crystalline form of Compound I), in combination with one or more (e.g., one, two, three, four, one or two, or one to three, or one to four) additional therapeutic agents are provided.

In the above embodiments, the additional therapeutic agent may be an anti-HBV agent. For example, in some embodiments, the additional therapeutic agent is selected from the group consisting of HBV combination drugs, HBV DNA polymerase inhibitors, immunomodulators, toll-like receptor modulators (modulators of TLR1, TLR2, TLR3, TLR4, TLR5, TLR6, TLR7, TLR8, TLR9, TLR10, TLR11, TLR12 and TLR13), interferon alpha receptor ligands, hyaluronidase inhibitors, recombinant IL-7, hepatitis B surface antigen (HBsAg) inhibitors, hepatitis B surface antigen (HBsAg) secretion or assembly inhibitors, compounds targeting hepatitis B core antigen (HBcAg), cyclophilin inhibitors, HBV therapeutic vaccines, HBV prophylactic vaccines, HBV viral entry inhibitors, NTCP (Na+-taurocholate cotransporting polypeptide) inhibitors, antisense oligonucleotide targeting viral mRNA, short interfering RNAs (siRNA), miRNA gene therapy agents, endonuclease modulators, inhibitors of ribonucleotide reductase, hepatitis B virus E antigen inhibitors, recombinant scavenger receptor A (SRA) proteins, Src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives, TCR-like antibodies), CCR2 chemokine antagonists, thymosin agonists, cytokines, nucleoprotein modulators (HBV core or capsid protein modulators), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 (CTLA4) inhibitors, IDO inhibitors, cccDNA epigenetic modifiers, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, Hepatitis B virus replication inhibitors compounds such as those disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), US20130217880 (Ono pharmaceutical), US20100015178 (Incyte) and other drugs for treating HBV, and combinations thereof.

In certain embodiments, the additional therapeutic is selected from the group consisting of HBV combination drugs, HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, hepatitis B surface antigen (HBsAg) secretion or assembly inhibitors, compounds targeting HBcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen inhibitors, HBx inhibitors, cccDNA inhibitors, HBV antibodies including HBV antibodies targeting the surface antigens of the hepatitis B virus, thymosin agonists, cytokines, nucleoprotein modulators (HBV core or capsid protein modulators), stimulators of retinoic acid-inducible gene 1, stimulators of NOD2, stimulators of NOD1, recombinant thymosin alpha-1, BTK inhibitors, IDO inhibitors, hepatitis B virus replication inhibitors, and combinations thereof.

In certain embodiments a crystalline form of Compound I is formulated as a tablet, which may optionally contain one or more other compounds useful for treating HBV. In certain embodiments, the tablet can contain another active ingredient for treating HBV, such as HBV DNA polymerase inhibitors, immunomodulators, toll-like receptor modulators (modulators of TLR1, TLR2, TLR3, TLR4, TLR5, TLR6, TLR7, TLR8, TLR9, TLR10, TLR11, TLR12 and TLR13), modulators of TLR7, modulators of TLR8, modulators of TLR7 and TLR8, interferon alpha receptor ligands, hyaluronidase inhibitors, hepatitis B surface antigen (HBsAg) inhibitors, hepatitis B surface antigen (HBsAg) secretion or assembly inhibitors, compounds targeting hepatitis B core antigen (HBcAg), cyclophilin inhibitors, HBV viral entry inhibitors, NTCP (Na+-taurocholate cotransporting polypeptide) inhibitors, endonuclease modulators, inhibitors of ribonucleotide reductase, hepatitis B virus E antigen inhibitors, Src kinase inhibitors, HBx inhibitors, cccDNA inhibitors, CCR2 chemokine antagonists, thymosin agonists, nucleoprotein modulators (HBV core or capsid protein modulators), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 (CTLA4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, BTK inhibitors, modulators of TIGIT, cccDNA epigenetic modifiers, modulators of CD47, modulators of SIRP alpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, IAPs inhibitors, SMAC mimetics, IDO inhibitors, and Hepatitis B virus replication inhibitors, and combinations thereof.

In certain embodiments, such tablets are suitable for once daily dosing.

In certain embodiments, the additional therapeutic agent is selected from one or more of:

(1) Combination drugs selected from the group consisting of tenofovir disoproxil fumarate+emtricitabine (TRU-VADA®), ABX-203+lamivudine+PEG-IFNalpha, and ABX-203+adefovir+PEG-IFNalpha, INO-9112+RG7944 (INO-1800);

(2) HBV DNA polymerase inhibitors selected from the group consisting of besifovir, entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, telbivudine (Tyzeka®), pradefovir, Clevudine, emtricitabine (Emtriva®), ribavirin, lamivudine (Epivir-HBV®), phosphazide, famciclovir, SNC-019754, FMCA, fusolin, AGX-1009, AR-II-04-26, HS-10234 and metacavir;

(3) Immunomodulators selected from the group consisting of rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765 and IR-103;

(4) Toll-like receptor 7 modulators selected from the group consisting of GS-9620, GSK-2245035, imiquimod, resiquimod, DSR-6434, DSP-3025, IMO-4200, MCT-465, 3M-051, SB-9922, 3M-052, Limtop, TMX-30X, TMX-202 RG-7863 and RG-7795;

(5) Toll-like receptor 8 modulators selected from the group consisting of motolimod, resiquimod, 3M-051, 3M-052, MCT-465, IMO-4200, VTX-763, VTX-1463;

(6) Toll-like receptor 3 modulators selected from the group consisting of rintatolimod, poly-ICLC, MCT-465, MCT-475, Riboxxon, Riboxxim and ND-1.1;

(7) Interferon alpha receptor ligands selected from the group consisting of interferon alpha-2b (Intron A®), pegylated interferon alpha-2a (Pegasys®), interferon alpha 1b (Hapgen®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-Intron®), Bioferon, Novaferon, Inmutag (Inferon), Multiferon®, interferon alfa-n1 (Humoferon®), interferon beta-1a (Avonex®), Shaferon, interferon alfa-2b (AXXO), Alfaferone, interferon alfa-2b (BioGeneric Pharma), interferon-alpha 2 (CJ), Laferonum, VIPEG, BLAUFERON-B, BLAUFERON-A, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, Pegi-Hep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b and Interapo (Interapa);

(8) Hyaluronidase inhibitors selected from the group consisting of astodrimer;

(9) Modulators of IL-10;

(10) HBsAg inhibitors selected from the group consisting of HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006 and REP-9AC';

(11) Toll like receptor 9 modulators selected from CYT003 and CYT-003-QbG10;

(12) Cyclophilin inhibitors selected from the group consisting of OCB-030, SCY-635 and NVP-018;

(13) HBV Prophylactic vaccines selected from the group consisting of Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, Engerix B®, recombinant hepatitis B vaccine (intramuscular, Kangtai Biological Products), recombinant hepatitis B vaccine (Hansenual polymorpha yeast, intramuscular, Hualan Biological Engineering), Bimmugen, Euforavac, Eutravac, anrix-DTaP-IPV-Hep B, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine;

(14) HBV Therapeutic vaccines selected from the group consisting of HBsAG-HBIG complex, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, and Lm HBV;

(15) HBV viral entry inhibitor selected from the group consisting of Myrcludex B;

(16) Antisense oligonucleotide targeting viral mRNA selected from the group consisting of ISIS-HBVRx;

(17) short interfering RNAs (siRNA) selected from the group consisting of TKM-HBV (TKM-HepB), ALN-HBV, SR-008, ddRNAi and ARC-520;
(18) Endonuclease modulators selected from the group consisting of PGN-514;
(19) Inhibitors of ribonucleotide reductase selected from the group consisting of Trimidox;
(20) Hepatitis B virus E antigen inhibitors selected from the group consisting of wogonin;
(21) HBV antibodies targeting the surface antigens of the hepatitis B virus selected from the group consisting of GC-1102, XTL-17, XTL-19, XTL-001, KN-003, IV Hepabulin SN, and fully human monoclonal antibody therapy (hepatitis B virus infection, Humabs BioMed);
(22) HBV antibodies including monoclonal antibodies and polyclonal antibodies selected from the group consisting of Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products) and Fovepta (BT-088);
(23) CCR2 chemokine antagonists selected from the group consisting of propagermanium;
(24) Thymosin agonists selected from the group consisting of Thymalfasin;
(25) Cytokines selected from the group consisting of recombinant IL-7, CYT-107, interleukin-2 (IL-2, Immunex); recombinant human interleukin-2 (Shenzhen Neptunus), IL-15, IL-21, IL-24 and celmoleukin;
(26) Nucleoprotein modulators (HBV core or capsid protein modulators) selected from the group consisting of NVR-1221, NVR-3778, BAY 41-4109, morphothiadine mesilate and DVR-23;
(27) Stimulators of retinoic acid-inducible gene 1 selected from the group consisting of SB-9200, SB-40, SB-44, ORI-7246, ORI-9350, ORI-7537, ORI-9020, ORI-9198 and ORI-7170;
(28) Stimulators of NOD2 selected from the group consisting of SB-9200;
(29) Recombinant thymosin alpha-1 selected from the group consisting of NL-004 and PEGylated thymosin alpha 1;
(30) Hepatitis B virus replication inhibitors selected from the group consisting of isothiafludine, IQP-HBV, RM-5038 and Xingantie;
(31) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;
(32) cccDNA inhibitors selected from the group consisting of BSBI-25;
(33) PD-L1 inhibitors selected from the group consisting of MEDI-0680, RG-7446, durvalumab, KY-1003, KD-033, MSB-0010718C, TSR-042, ALN-PDL, STI-A1014 and BMS-936559;
(34) PD-1 inhibitors selected from the group consisting of nivolumab, pembrolizumab, pidilizumab, BGB-108 and mDX-400;
(35) BTK inhibitors selected from the group consisting of ACP-196, dasatinib, ibrutinib, PRN-1008, SNS-062, ONO-4059, BGB-3111, MSC-2364447, X-022, spebrutinib, TP-4207, HM-71224, KBP-7536 and AC-0025;
(36) IDO inhibitors selected from the group consisting of epacadostat (INCB24360), F-001287, resminostat (4SC-201), SN-35837, NLG-919, GDC-0919, and indoximod;
(37) Other drugs for treating HBV selected from the group consisting of gentiopicrin (gentiopicroside), nitazoxanide, birinapant, NOV-205 (Molixan; BAM-205), Oligotide, Mivotilate, Feron, levamisole, Ka Shu Ning, Alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbama, IBPB-006IA, Hepuyinfen, DasKloster 0014-01, Jiangantai (Ganxikang), picroside, DasKloster-0039, hepulantai, IMB-2613, TCM-800B, reduced glutathione, RO-6864018 and ZH-2N; and
(37) The compounds disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), and US20130217880 (Ono pharmaceutical), and US20100015178 (Incyte).

In certain embodiments, a compound disclosed herein (e.g. any crystalline form of Compound I), is combined with one, two, three, four or more additional therapeutic agents. In certain embodiments, a compound disclosed herein (e.g. any crystalline form of Compound I), is combined with two additional therapeutic agents. In other embodiments, a compound disclosed herein (e.g. any crystalline form of Compound I), is combined with three additional therapeutic agents. In further embodiments, a compound disclosed herein (e.g. any crystalline form of Compound I), is combined with four additional therapeutic agents. The one, two, three, four or more additional therapeutic agents can be different therapeutic agents selected from the same class of therapeutic agents, and/or they can be selected from different classes of therapeutic agents.

In a specific embodiment, a compound disclosed herein (e.g. any crystalline form of Compound I), is combined with an HBV DNA polymerase inhibitor. In another specific embodiment, a compound disclosed herein (e.g. any crystalline form of Compound I), is combined with an HBV DNA polymerase inhibitor and at least one additional therapeutic agent selected from the group consisting of: immunomodulators, toll-like receptor modulators (modulators of TLR1, TLR2, TLR3, TLR4, TLR5, TLR6, TLR7, TLR8, TLR9, TLR10, TLR11, TLR12 and TLR13), interferon alpha receptor ligands, hyaluronidase inhibitors, recombinant IL-7, HBsAg inhibitors, hepatitis B surface antigen (HBsAg) secretion or assembly inhibitors, compounds targeting HBcAg, cyclophilin inhibitors, HBV therapeutic vaccines, HBV prophylactic vaccines HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives, TCR-like antibodies), CCR2 chemokine antagonists, thymosin agonists, cytokines, nucleoprotein modulators (HBV core or capsid protein modulators), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 (CTLA4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, cccDNA epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, IDO inhibitors, and Hepatitis B virus replication inhibitors.

In another specific embodiment, a compound disclosed herein (e.g. any crystalline form of Compound I), is combined with an HBV DNA polymerase inhibitor and at least a second additional therapeutic agent selected from the group consisting of: immunomodulators, toll-like receptor modulators (modulators of TLR1, TLR2, TLR3, TLR4, TLR5, TLR6, TLR7, TLR8, TLR9, TLR10, TLR11, TLR12 and TLR13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives, TCR-like antibodies), cyclophilin inhibitors, stimulators of retinoic acid-inducible gene 1, PD-1 inhibitors, PD-L1 inhibitors, Arginase-1 inhibitors, PI3K inhibitors, IDO inhibitors, and stimulators of NOD2.

In another specific embodiment, a compound disclosed herein (e.g. any crystalline form of Compound I), is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein modulators (HBV core or capsid protein modulators).

In another specific embodiment, a compound disclosed herein (e.g. any crystalline form of Compound I), is combined with an HBV DNA polymerase inhibitor, one or two additional therapeutic agents selected from the group consisting of: immunomodulators, toll-like receptor modulators (modulators of TLR1, TLR2, TLR3, TLR4, TLR5, TLR6, TLR7, TLR8, TLR9, TLR10, TLR11, TLR12 and TLR13), HBsAg inhibitors, hepatitis B surface antigen (HBsAg) secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives, TCR-like antibodies), cyclophilin inhibitors, stimulators of retinoic acid-inducible gene 1, PD-1 inhibitors, PD-L1 inhibitors, Arginase-1 inhibitors, PI3K inhibitors, IDO inhibitors, and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein modulators (HBV core or capsid protein modulators).

In a particular embodiment, a compound disclosed herein (e.g. any crystalline form of Compound I), is combined with one, two, three, four or more additional therapeutic agents selected from adefovir (Hepsera®), tenofovir disoproxil fumarate+emtricitabine (TRUVADA®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin.

In a particular embodiment, a compound disclosed herein (e.g. any crystalline form of Compound I), is combined with entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®).

In a particular embodiment, a compound disclosed herein (e.g. any crystalline form of Compound I), is combined with entecavir (Baraclude®), adefovir (Hepsera®), tenofovir disoproxil fumarate (Viread®), tenofovir alafenamide hemifumarate, telbivudine (Tyzeka®) or lamivudine (Epivir- HBV®). In a particular embodiment, a compound disclosed herein (e.g. any crystalline form of Compound I) is combined with a PD-1 inhibitor. In a particular embodiment, a compound disclosed herein (e.g. any crystalline form of Compound I) is combined with a PD-L1 inhibitor. In a particular embodiment, a compound disclosed herein (e.g. any crystalline form of Compound I) is combined with an IDO inhibitor. In a particular embodiment, a compound disclosed herein (e.g. any crystalline form of Compound I) is combined with an IDO inhibitor and a PD-1 inhibitor. In a particular embodiment, a compound disclosed herein (e.g. any crystalline form of Compound I) is combined with an IDO inhibitor and a PD-L1 inhibitors.

In a particular embodiment, a compound disclosed herein (e.g. any crystalline form of Compound I), is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of immunomodulators, toll-like receptor modulators (modulators of TLR1, TLR2, TLR3, TLR4, TLR5, TLR6, TLR7, TLR8, TLR9, TLR10, TLR11, TLR12 and TLR13), interferon alpha receptor ligands, hyaluronidase inhibitors, recombinant IL-7, HBsAg inhibitors, hepatitis B surface antigen (HBsAg) secretion or assembly inhibitors, compounds targeting HbcAg, cyclophilin inhibitors, HBV Therapeutic vaccines, HBV prophylactic vaccines, HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives, TCR-like antibodies), CCR2 chemokine antagonists, thymosin agonists, cytokines, nucleoprotein modulators (HBV core or capsid protein modulators), stimulators of retinoic acid-inducible gene 1, stimulators of NOD2, stimulators of NOD1, IDO inhibitors, recombinant thymosin alpha-1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 (CTLA4) inhibitors, CD137 inhibitors, Killer cell lectin-like receptor subfamily G member 1 inhibitors, TIM-3 inhibitors, B- and T-lymphocyte attenuator inhibitors, cccDNA epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, and Hepatitis B virus replication inhibitors.

In a particular embodiment, a compound disclosed herein (e.g. any crystalline form of Compound I), is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin;

In a particular embodiment, a compound disclosed herein (e.g. any crystalline form of Compound I), is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of immunomodulators, toll-like receptor modulators (modulators of TLR1, TLR2, TLR3, TLR4, TLR5, TLR6, TLR7, TLR8, TLR9, TLR10, TLR11, TLR12 and TLR13), HBsAg inhibitors, hepatitis B surface antigen (HBsAg) secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives, TCR-like antibodies), cyclophilin inhibitors, stimulators of retinoic acid-inducible gene 1, Arginase-1 inhibitors, PI3K inhibitors, PD-1 inhibitors, PD-L1 inhibitors, IDO inhibitors, and stimulators of NOD2.

In a particular embodiment, a compound disclosed herein (e.g. any crystalline form of Compound I), is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein modulators (HBV core or capsid protein modulators).

In a particular embodiment, a compound disclosed herein (e.g. any crystalline form of Compound I), is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®), one or two additional therapeutic agents selected from the group consisting of: immunomodulators, toll-like receptor modulators (modulators of TLR1, TLR2, TLR3, TLR4, TLR5, TLR6, TLR7, TLR8, TLR9, TLR10, TLR11, TLR12 and TLR13), HBsAg inhibitors, hepatitis B surface antigen (HBsAg) secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives, TCR-like antibodies), cyclophilin inhibitors, stimulators of retinoic acid-inducible gene 1, PD-1 inhibitors, PD-L1 inhibitors, Arginase-1 inhibitors, P13K inhibitors, IDO inhibitors, and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein modulators (HBV core or capsid protein modulators).

In certain embodiments, a compound disclosed herein (e.g. any crystalline form of Compound I), is combined with 5-30 mg tenofovir alafenamide fumarate, tenofovir alafenamide hemifumarate, or tenofovir alafenamide. In certain embodiments, a compound disclosed herein (e.g. any crystalline form of Compound I), is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein (e.g. any crystalline form of Compound I), is combined with 10 mg tenofovir alafenamide fumarate, tenofovir alafenamide hemifumarate, or tenofovir alafenamide. In certain embodiments, a compound disclosed herein (e.g. any crystalline form of Compound I), is combined with 25 mg tenofovir alafenamide fumarate, tenofovir alafenamide hemifumarate, or tenofovir alafenamide. A compound as disclosed herein (e.g., a crystalline form of Compound I) may be combined with the agents provided herein in any dosage amount of the compound (e.g., from 1 mg to 500 mg of compound) the same as if each combination of dosages were specifically and individually listed.

In certain embodiments, a compound disclosed herein (e.g. any crystalline form of Compound I), is combined with 100-400 mg tenofovir disoproxil fumarate, tenofovir disoproxil hemifumarate, or tenofovir disoproxil. In certain embodiments, a compound disclosed herein (e.g. any crystalline form of Compound I), is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein (e.g. any crystalline form of Compound I), is combined with 300 mg tenofovir disoproxil fumarate, tenofovir disoproxil hemifumarate, or tenofovir disoproxil. In certain embodiments, a compound disclosed herein (e.g. any crystalline form of Compound I), is combined with 250 mg tenofovir disoproxil fumarate, tenofovir disoproxil hemifumarate, or tenofovir disoproxil. In certain embodiments, a compound disclosed herein (e.g. any crystalline form of Compound I), is combined with 150 mg tenofovir disoproxil fumarate, tenofovir disoproxil hemifumarate, or tenofovir disoproxil. A compound as disclosed herein (e.g., a crystalline form of Compound I) may be combined with the agents provided herein in any dosage amount of the compound (e.g., from 1 mg to 500 mg of compound) the same as if each combination of dosages were specifically and individually listed.

In certain embodiments, a method for treating or preventing an HIV infection in a human having or at risk of having the infection is provided, comprising administering to the human a therapeutically effective amount of a compound disclosed herein (e.g. any crystalline form of Compound I), in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein (e.g. any crystalline form of Compound I), in combination with a therapeutically effective amount of one or more (e.g., one, two, three, one or two, or one to three) additional therapeutic agents.

In certain embodiments, the present disclosure provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

A compound as disclosed herein (e.g. any crystalline form of Compound I) may be combined with one or more additional therapeutic agents in any dosage amount of the compound of Formula I (e.g., from 1 mg to 1000 mg of compound).

In one embodiment, pharmaceutical compositions comprising a compound disclosed herein (e.g. any crystalline form of Compound I), in combination with one or more (e.g., one, two, three, one or two, or one to three) additional therapeutic agents, and a pharmaceutically acceptable carrier, diluent or excipient are provided.

In one embodiment, kits comprising a compound disclosed herein (e.g. any crystalline form of Compound I), in combination with one or more (e.g., one, two, three, one or two, or one to three) additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists,), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, reverse transcriptase priming complex inhibitors, HIV gene therapy, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a crystalline form of Compound I is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing. In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® (EVIPLERA®, rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, TRIUMEQ® (dolutegravir+abacavir+lamivudine), lamivudine+nevirapine+zidovudine, dolutegravir+rilpivirine, dolutegravir+rilpivirine hydrochloride, atazanavir sulfate+cobicistat, atazanavir+cobicistat, darunavir+cobicistat, efavirenz+lamivudine+tenofovir disoproxil fumarate, tenofovir alafenamide hemifumarate+emtricitabine+cobicistat+elvitegravir, tenofovir alafenamide hemifumarate+emtricitabine, tenofovir alafenamide+emtricitabine, tenofovir alafenamide hemifumarate+emtricitabine+rilpivirine, tenofovir alafenamide+emtricitabine+rilpivirine, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Livexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), doravirine+lamivudine+tenofovir disoproxil fumarate, doravirine+lamivudine+tenofovir disoproxil, tenofovir+lamivudine and lamivudine+tenofovir disoproxil fumarate;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddI), zidovudine, emtricitabine, didanosine, stavudine, zalcitabine, lamivudine, censavudine, abacavir, abacavir sulfate, elvucitabine, alovudine, phosphazid, fozivudine tidoxil, apricitabine, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir and cabotegravir;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), nifeviroc (TD-0232), TD-0680, and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;
(13) Pharmacokinetic enhancers selected from the group consisting of cobicistat and ritonavir;
(14) Immune-based therapies selected from the group consisting of dermaVir, interleukin-7, plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-12, polymer polyethyleneimine (PEI), Gepon, VGV-1, MOR-22, BMS-936559, toll-like receptors modulators (TLR1, TLR2, TLR3, TLR4, TLR5, TLR6, TLR7, TLR8, TLR9, TLR10, TLR11, TLR12 and TLR13), rintatolimod and IR-103;
(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine (Novartis), Remune, ITV-1, Contre Vir, Ad5-ENVA-48, DCVax-001 (CDX-2401), PEP-6409, Vacc-4x, Vacc-C5, VAC-3S, multiclade DNA recombinant adenovirus-5 (rAd5), Pennvax-G, VRC-HIV MAB060-00-AB, AVX-101, HIV-TriMix-mRNA vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, ThV-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, Combi-HIVvac, ADVAX, MYM-V201, MVA-CMDR, MVATG-17401, ETV-01, CDX-1401, rcAd26.MOS1.HIV-Env and DNA-Ad5 gag/pol/nef/nev (HVTN505);
(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523 and VRC07;
(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;
(18) HIV nucleocapsid p7 (NCp7) inhibitors selected from the group consisting of azodicarbonamide;
(19) HIV maturation inhibitors selected from the group consisting of BMS-955176 and GSK-2838232;
(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;
(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and
(22) other drugs for treating HIV selected from the group consisting of BanLec, MK-8507, AG-1105, TR-452, MK-8591, REP 9, CYT-107, alisporivir, NOV-205, IND-02, metenkefalin, PGN-007, Acemannan, Gamimune, Prolastin, 1,5-dicaffeoylquinic acid, BIT-225, RPI-MN, VSSP, Hlviral, IMO-3100, SB-728-T, RPI-MN, VIR-576, HGTV-43, MK-1376, rHIV7-shl-TAR-CCR5RZ, MazF gene therapy, BlockAide, ABX-464, SCY-635, naltrexone, AAV-eCD4-Ig gene therapy, TEV-90110, TEV-90112, TEV-90111, TEV-90113, deferiprone, HS-10234, and PA-1050040 (PA-040).

In certain embodiments, a compound disclosed herein (e.g. any crystalline form of Compound I), is combined with one, two, three, four or more additional therapeutic agents. In certain embodiments, a compound disclosed herein (e.g. any crystalline form of Compound I), is combined with two additional therapeutic agents. In other embodiments, a compound disclosed herein (e.g. any crystalline form of Compound I), is combined with three additional therapeutic agents. In further embodiments, a compound disclosed herein (e.g. any crystalline form of Compound I), is combined with four additional therapeutic agents. The one, two, three, four or more additional therapeutic agents can be different therapeutic agents selected from the same class of therapeutic agents, and/or they can be selected from different classes of therapeutic agents. In a specific embodiment, a compound disclosed herein (e.g. any crystalline form of Compound I), is combined with an HIV nucleoside or nucleotide inhibitor of reverse transcriptase and an HIV non-nucleoside inhibitor of reverse transcriptase. In another specific embodiment, a compound disclosed herein (e.g. any crystalline form of Compound I), is combined with an HIV nucleoside or nucleotide inhibitor of reverse transcriptase, and an HIV protease inhibiting compound. In a further embodiment, a compound disclosed herein (e.g. any crystalline form of Compound I), is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein (e.g. any crystalline form of Compound I), is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein (e.g. any crystalline form of Compound I), is combined with at least one HIV nucleoside inhibitor of reverse transcriptase, an integrase inhibitor, and a pharmacokinetic enhancer. In another embodiment, a compound disclosed herein (e.g. any crystalline form of Compound I), is combined with two HIV nucleoside or nucleotide inhibitors of reverse transcriptase.

In a particular embodiment, a compound disclosed herein (e.g. any crystalline form of Compound I), is combined with one, two, three, four or more additional therapeutic agents selected from Triumeq® (dolutegravir+abacavir+lamivudine), dolutegravir+abacavir sulfate+lamivudine, raltegravir, raltegravir+lamivudine, Truvada® (tenofovir disoproxil fumarate+emtricitabine, TDF+FTC), maraviroc, enfuvirtide, Epzicom® (Livexa®, abacavir sulfate+lamivudine, ABC+ 3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+ emtricitabine), rilpivirine, rilpivirine hydrochloride, Complera® (Eviplera®, rilpivirine+tenofovir disoproxil fumarate+emtricitabine), Cobicistat, atazanavir sulfate+cobicistat, atazanavir+cobicistat, darunavir+cobicistat, Atripla® (efavirenz+tenofovir disoproxil fumarate+emtricitabine), atazanavir, atazanavir_sulfate, dolutegravir, elvitegravir, Aluvia® (Kaletra®, lopinavir+ritonavir), ritonavir, emtricitabine, atazanavir_sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, darunavir+cobicistat, atazanavir sulfate+cobicistat, atazanavir+cobicistat, tenofovir alafenamide and tenofovir alafenamide hemifumarate.

In a particular embodiment, a compound disclosed herein (e.g. any crystalline form of Compound I), is combined with abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound disclosed herein (e.g. any crystalline form of Compound I), is combined with tenofovir, tenofovir disoproxil, tenofovir disoproxil fumarate, tenofovir alafenamide, or tenofovir alafenamide hemifumarate.

In a particular embodiment, a compound disclosed herein (e.g. any crystalline form of Compound I), is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound disclosed herein (e.g. any crystalline form of Compound I), is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound disclosed herein (e.g. any crystalline form of Compound I), is combined with 5-30 mg tenofovir alafenamide fumarate, tenofovir alafenamide hemifumarate, or tenofovir alafenamide and 200 mg emtricitabine. In certain embodiments, a compound disclosed herein (e.g. any crystalline form of Compound I), is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound disclosed herein (e.g. any crystalline form of Compound I), is combined with 10 mg tenofovir alafenamide fumarate, tenofovir alafenamide hemifumarate, or tenofovir alafenamide and 200 mg emtricitabine. In certain embodiments, a compound disclosed herein (e.g. any crystalline form of Compound I), is combined with 25 mg tenofovir alafenamide fumarate, tenofovir alafenamide hemifumarate, or tenofovir alafenamide and 200 mg emtricitabine. A compound as disclosed herein (e.g., any crystalline form of Compound I) may be combined with the agents provided herein in any dosage amount of the compound (e.g., from 50 mg to 500 mg of compound) the same as if each combination of dosages were specifically and individually listed.

In certain embodiments, a compound disclosed herein (e.g. any crystalline form of Compound I), is combined with 200-400 mg tenofovir disoproxil fumarate, tenofovir disoproxil hemifumarate, or tenofovir disoproxil and 200 mg emtricitabine. In certain embodiments, a compound disclosed herein (e.g. any crystalline form of Compound I), is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In certain embodiments, a compound disclosed herein (e.g. any crystalline form of Compound I), is combined with 300 mg tenofovir disoproxil fumarate, tenofovir disoproxil hemifumarate, or tenofovir disoproxil and 200 mg emtricitabine. A compound as disclosed herein (e.g. any crystalline form of Compound I) may be combined with the agents provided herein in any dosage amount of the compound (e.g., from 1 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

VIII. Examples

Abbreviations as used herein have respective meanings as follows:

| | |
|---|---|
| Ac | Acetate |
| ACN | Acetonitrile |
| BippyPhos | 5-(di-tert-butylphosphino)-1',3',5'-triphenyl-1'H-[1,4']bipyrazole |
| Bn | Benzyl |
| br. s | Broad singlet |
| Bu | Butyl |
| dba | Dibenzylideneacetone |
| DCM | Dichloromethane |
| dd | Doublet of doublets |
| ddd | Doublet of doublet of doublets |
| DIPE | diisopropyl ether |
| DMF | Dimethylformamide |
| DMSO | Dimethylsulfoxide |
| dr | Diastereomeric ratio |
| DSC | Differential scanning calorimetry |
| DVS | Dynamic vapor sorption |
| ee | Enantiomeric excess |
| equiv | Equivalents |
| Et | Ethyl |
| EtOAc | Ethyl acetate |
| EtOH | Ethanol |
| ft | Foot (length) |
| g | Gram |
| GC | Gas chromatography |
| h | Hour |
| HBV | Hepatitis B virus |
| HCV | Hepatitis C virus |
| HFIPA | hexafluoroisopropanol |
| HIV | Human Immunodeficiency virus |
| HPLC | High-pressure liquid chromatography |
| IPA | Isopropyl alcohol |
| IPAc | Isopropyl acetate |
| iPr | Isopropyl |
| iPrOAc or IPAc | isopropyl acetate |
| kg | Kilogram |
| L | Liter |
| m | Multiplet |
| M | Molar |
| Me | Methyl |
| MEK | methyl ethyl ketone |
| MeOH | methanol |
| Me—THF | 2 methyl tetrahydrofuran |
| mg | Milligram |
| MHz | Mega hertz |
| MIBK | Methylisobutyl ketone |
| min | Minute |
| mL | Milliliter |
| mmol | Millimole |
| mol | Mole |
| MTBE | Methyl-tert-butyl ether |
| N | Normal |
| NLT | No less than |
| NMR | Nuclear magnetic resonance |
| Ph | Phenyl |
| RH | Relative humidity |
| s | Singlet |
| t-Bu | tert-Butyl |
| td | Triplet of doublets |
| Tf | Trifluoromethanesulfonate |
| TFE | trifluoroethanol |
| TGA | Thermogravimetric analysis |
| THF | Tetrahydrofuran |
| TMS | Trimethylsilyl |
| vol | Volume |
| wt | Weight |
| XRPD | X-ray powder diffraction |
| δ | Chemical shift |
| µL | Microliter |

The solid forms (polymorphs, solvates and hydrates) of Compound I were characterized by a variety of the following methods.

X-ray Powder Diffraction (XRPD). The Rigaku Smart-Lab® X-ray diffraction system was configured for reflection BraggBrentano geometry using a line source X-ray beam. The x-ray source is a Cu Long Fine Focus tube that was operated at 40 kV and 44 mA. That source provides an incident beam profile at the sample that changes from a narrow line at high angles to a broad rectangle at low angles. Beam conditioning slits were used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. The single-crystal, Si, low-background holder has a small circular recess (7 mm diameter and about 1 mm depth) that holds between 5 and 10 mg of powdered material. Each sample was analyzed from 2 to 40°2θ using a continuous scan of 3° 2θ per minute with an effective step size of 0.02° 2θ.

Solubility Estimations. Solubilities were estimated by treating a weighed sample of Compound I with measured aliquots of the test solvent at ambient temperature, with shaking and/or sonication between aliquots. Dissolution was determined by visual inspection. Solubility numbers were calculated by dividing the total amount of solvent used to dissolve the sample by the weight of the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than" if dissolution occurred on addition of the first solvent aliquot.

Differential Scanning Calorimetry (DSC). DSC analyses were carried out using a TA Instruments Q2000 instrument. The instrument temperature calibration was performed using indium. The DSC cell was kept under a nitrogen purge of ~50 mL per minute during each analysis. The sample was placed in a standard, crimped, aluminum pan and was heated from 20° C. to 350° C. at a rate of 10° C. per minute.

Thermogravimetric (TGA) Analysis. The TGA analysis was carried out using a TA Instruments Q50 instrument. The instrument balance was calibrated using class M weights and the temperature calibration was performed using alumel. The nitrogen purge was ~40 ml per minute at the balance and ~60 ml per minute at the furnace. Each sample was placed into a pretared platinum pan and heated from 20° C. to 350° C. at a rate of 10° C. per minute.

Karl Fischer (KF) Analyses. Karl Fischer analyses were carried out using a Mettler-Toledo C20 Coulometric KF titrator. The instrument was calibrated with a standard of known water concentration.

Dynamic Vapor Sorption (DVS). DVS analyses were carried out in a TA Instruments 05000 Dynamic Vapor Sorption analyzer. The instrument was calibrated with standard weights and a sodium bromide standard for humidity. Samples were analyzed at 25° C. with a maximum equilibration time of 60 minutes in 10% relative humidity (RH) steps from 5 to 95% RH (adsorption cycle) and from 95 to 5% RH (desorption cycle).

Example 1. Stable Form Screening of Compound I

Method I.

50 mg of Compound I was dissolved in 1 mL of methanol/dichloromethane, agitated, and then evaporated.

Method II.

A solution of Compound I, methanol and dichloromethane, was concentrated under vacuum at 40° C. to about 10 volumes. Methanol was charged and the reaction mixture was concentrated under vacuum at 40° C. to about 10 volumes (and repeated once). The slurry was agitated at 20° C. for at least 2 hours. The slurry was filtered and the filter cake was rinsed with methanol and ethyl acetate. The wet product was dried under vacuum at NMT 40° C.

Figure 3:
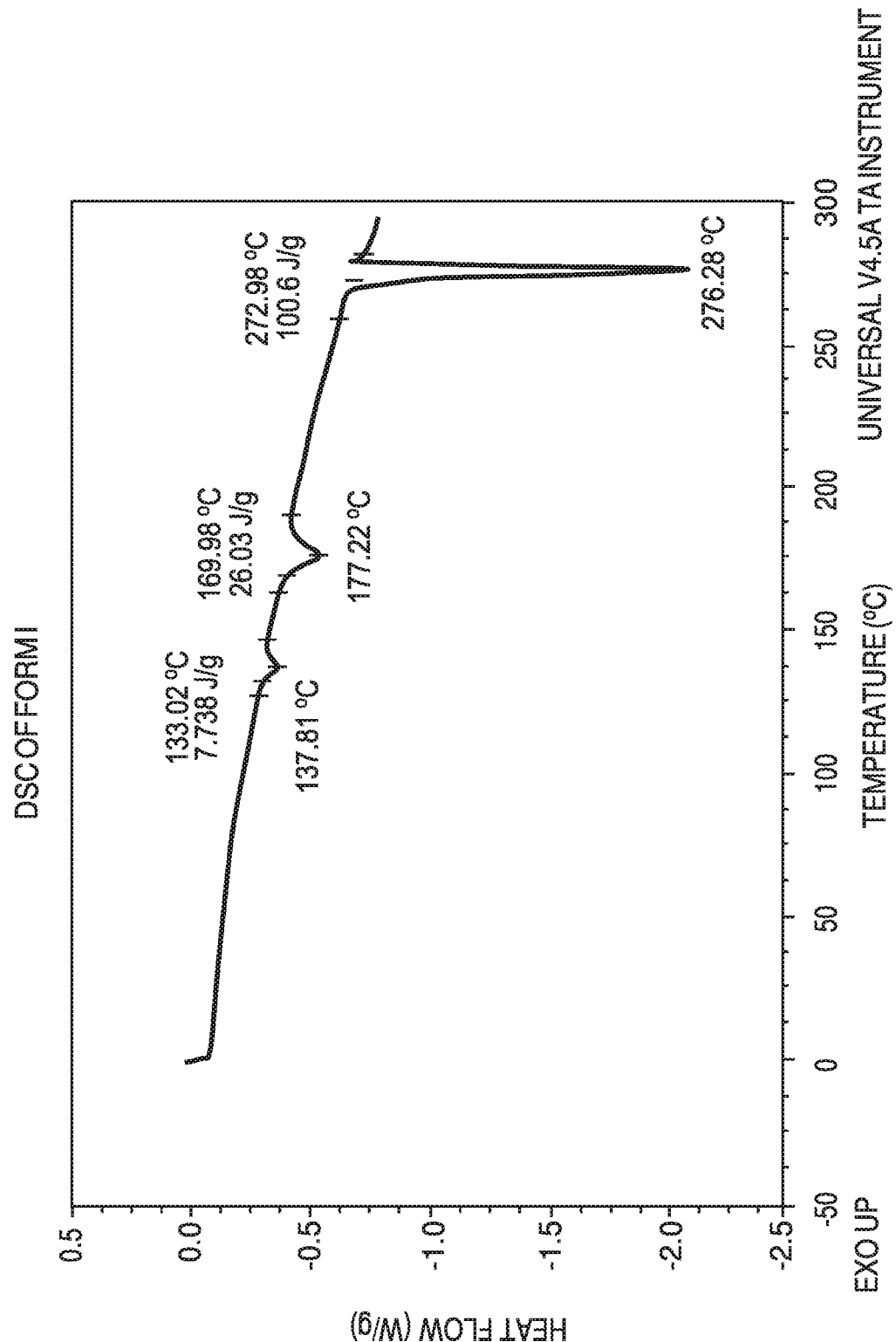
FIG. 3 shows a differential scanning calorimetry plot of Compound I Form I showing endotherms at about 133° C., about 170° C. and about 273° C.
Figure 4:
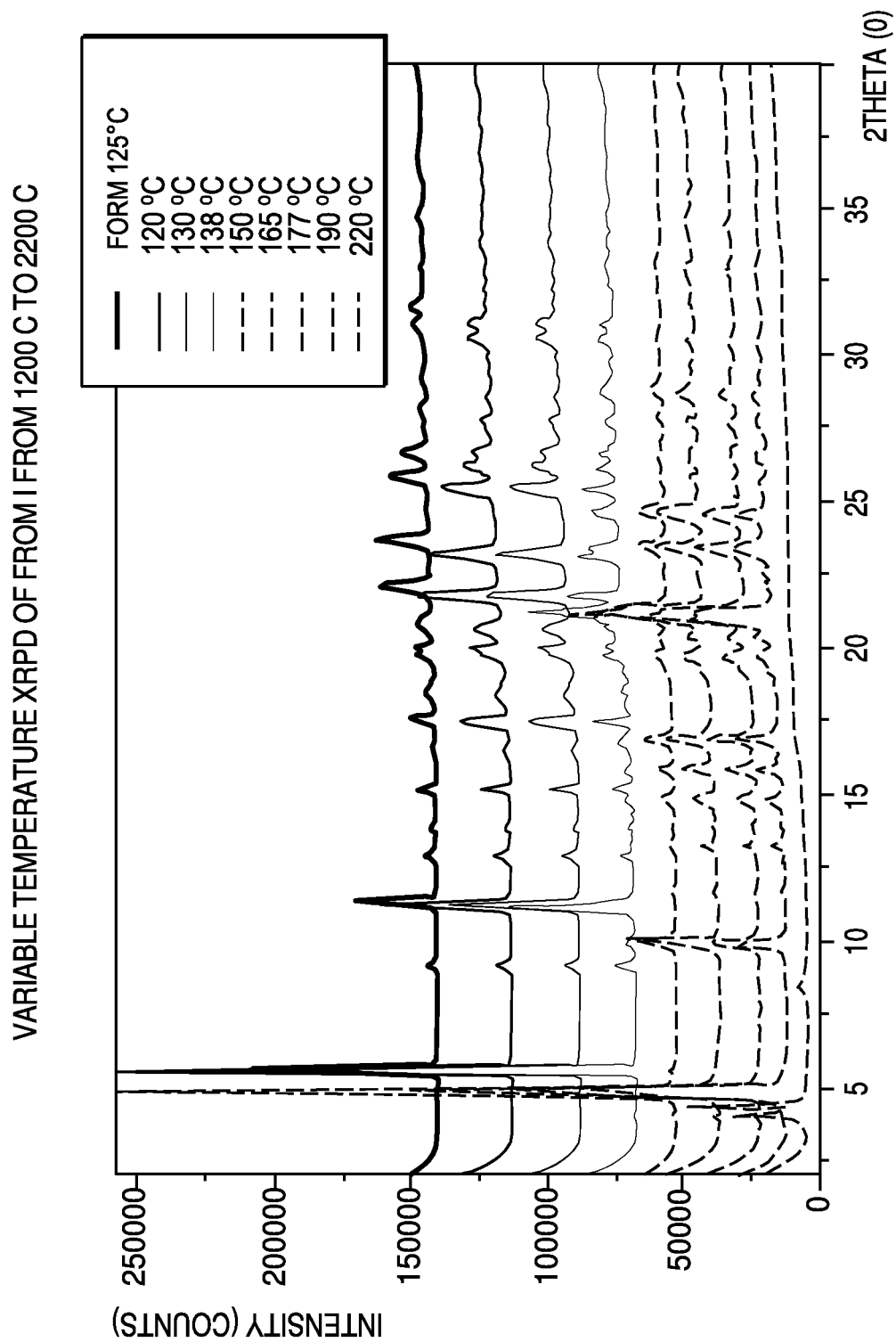
FIG. 4 shows a variable temperature XRPD plot of Compound I Form I converting to Form III at about 138° C.

Form I is characterized by the X-ray powder diffraction pattern in FIG. 1, and the differential scanning calorimetry plot in FIG. 3 showing endotherms at about 133 (conversion to Form III), 170 and 273° C. (decomposition).

Figure 5:
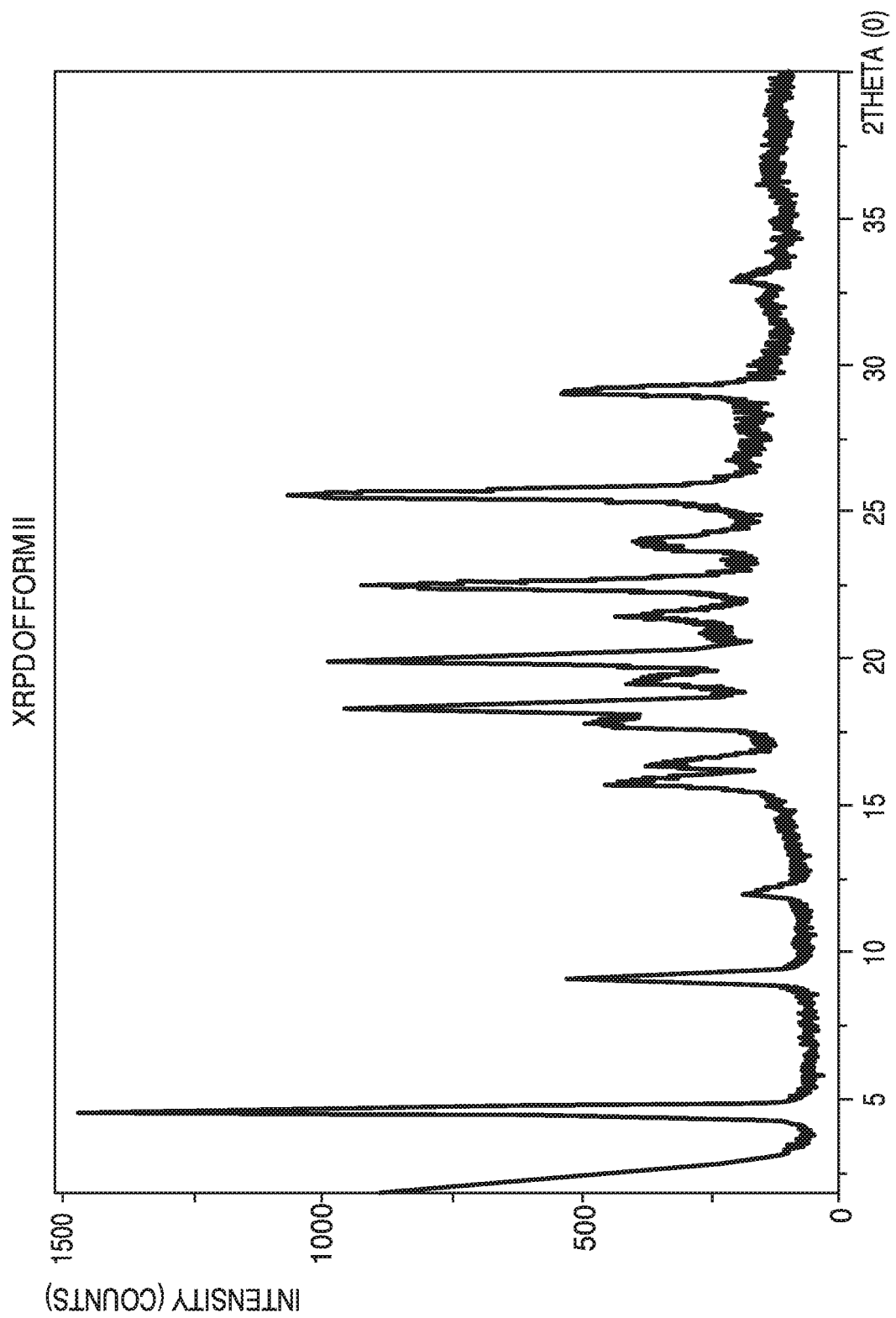
FIG. 5 shows an X-ray powder diffraction pattern of Compound I Form II.
Figure 7:
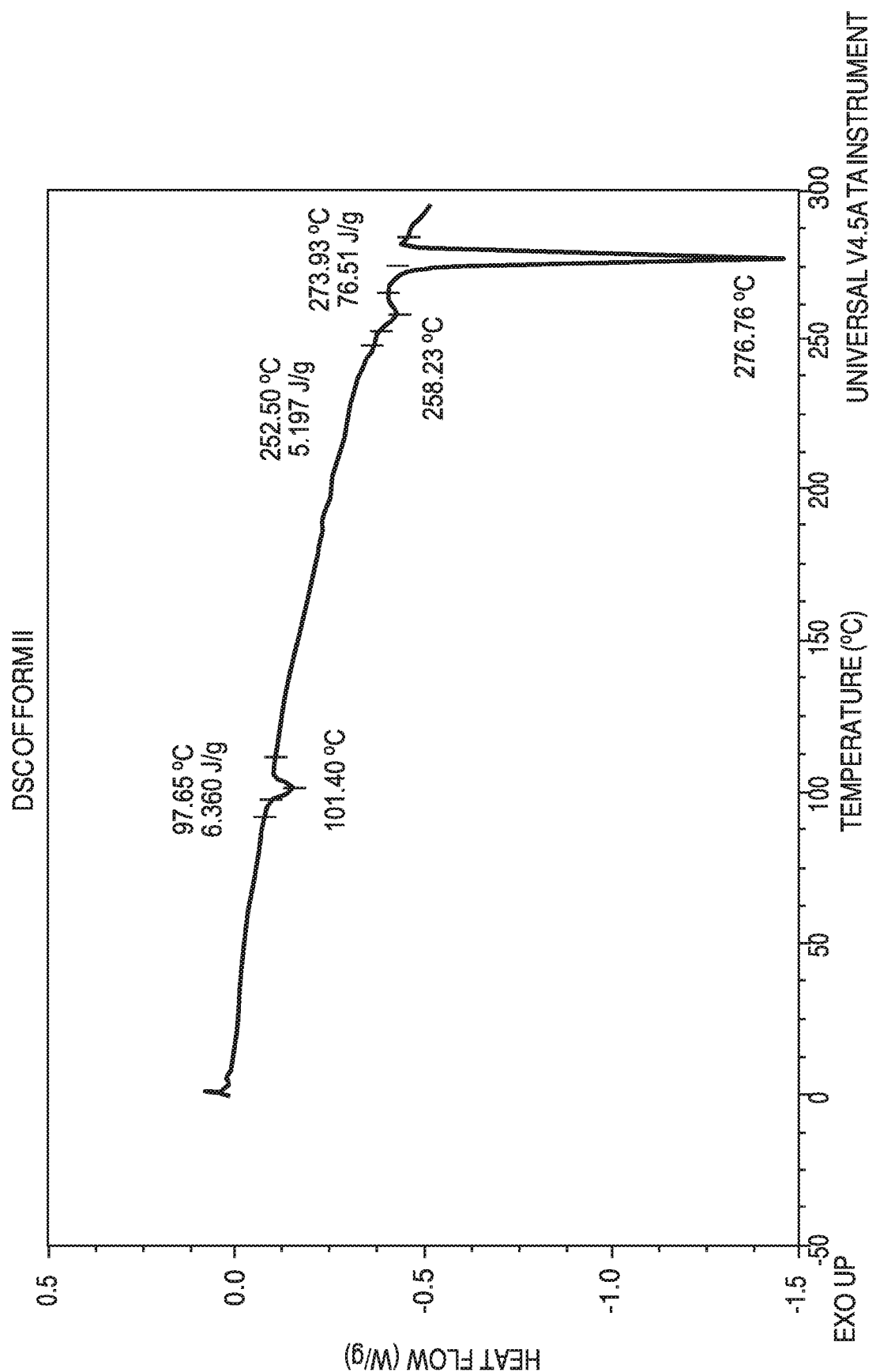
FIG. 7 shows a differential scanning calorimetry plot of Compound I Form II showing endotherms at about 98° C., about 253° C. and about 274° C.
Figure 8:
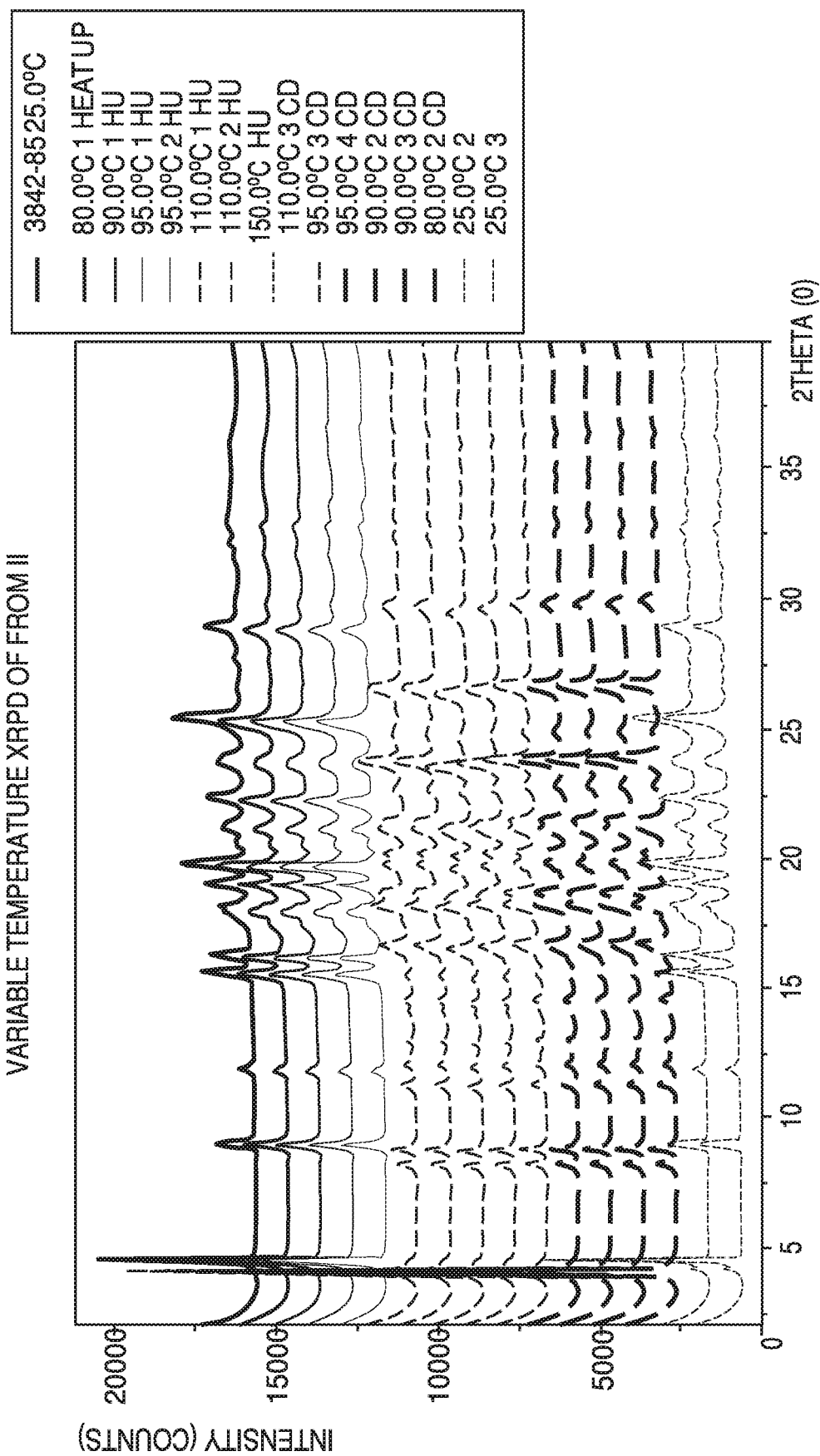
FIG. 8 shows a variable temperature XRPD plot of Compound I Form II converting to Form IV at about 110° C., and then reverting to Form II upon cooling to about 25° C.

Form II is characterized by the X-ray powder diffraction pattern in FIG. 5, and the differential scanning calorimetry plot in FIG. 7 showing endotherms at about 98° C. (conversion to Form IV), 253° C. and 274° C. (decomposition).

Figure 11:
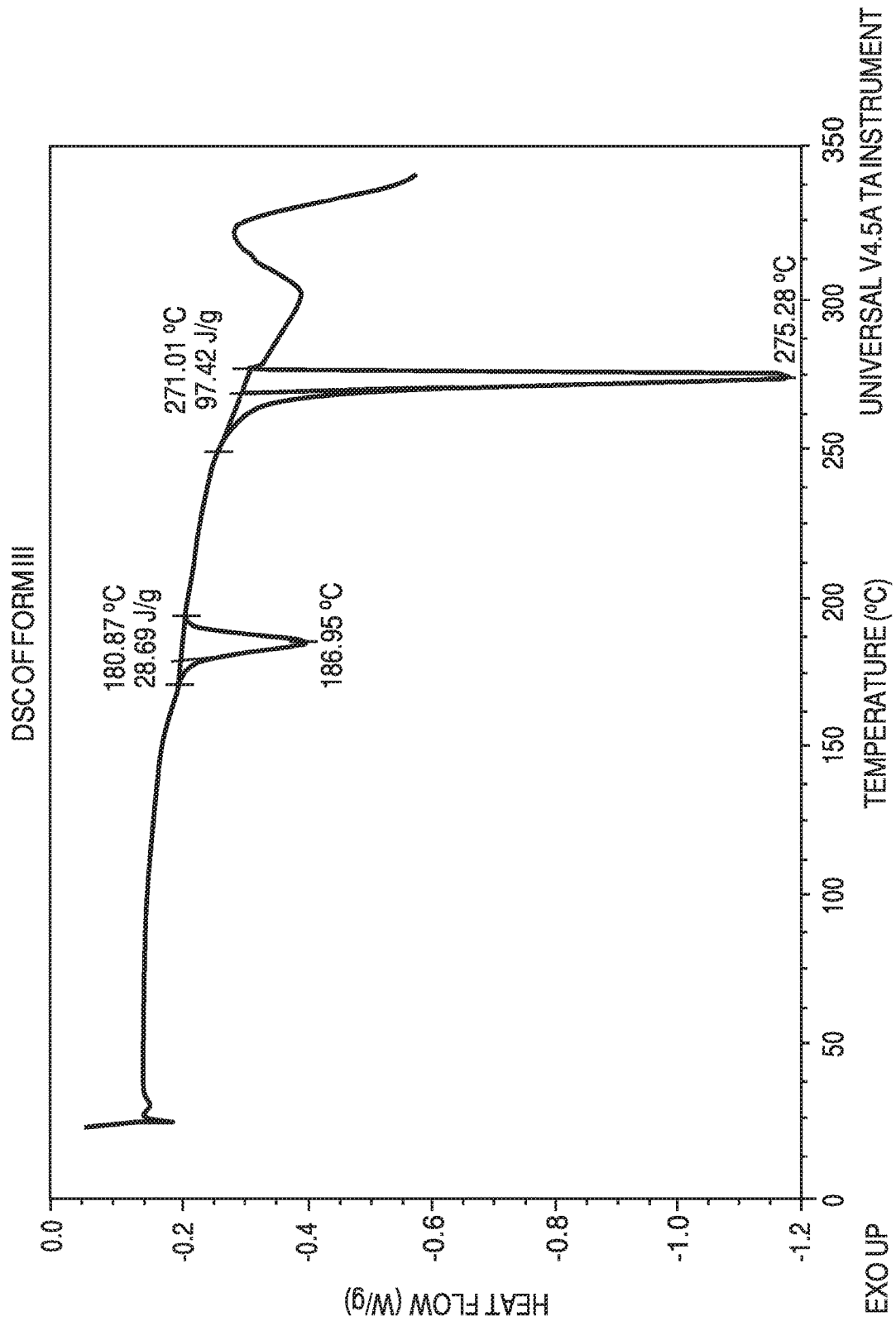
FIG. 11 shows a differential scanning calorimetry plot of Compound I Form III showing endotherms at about 181 and about 271° C.
Figure 12:
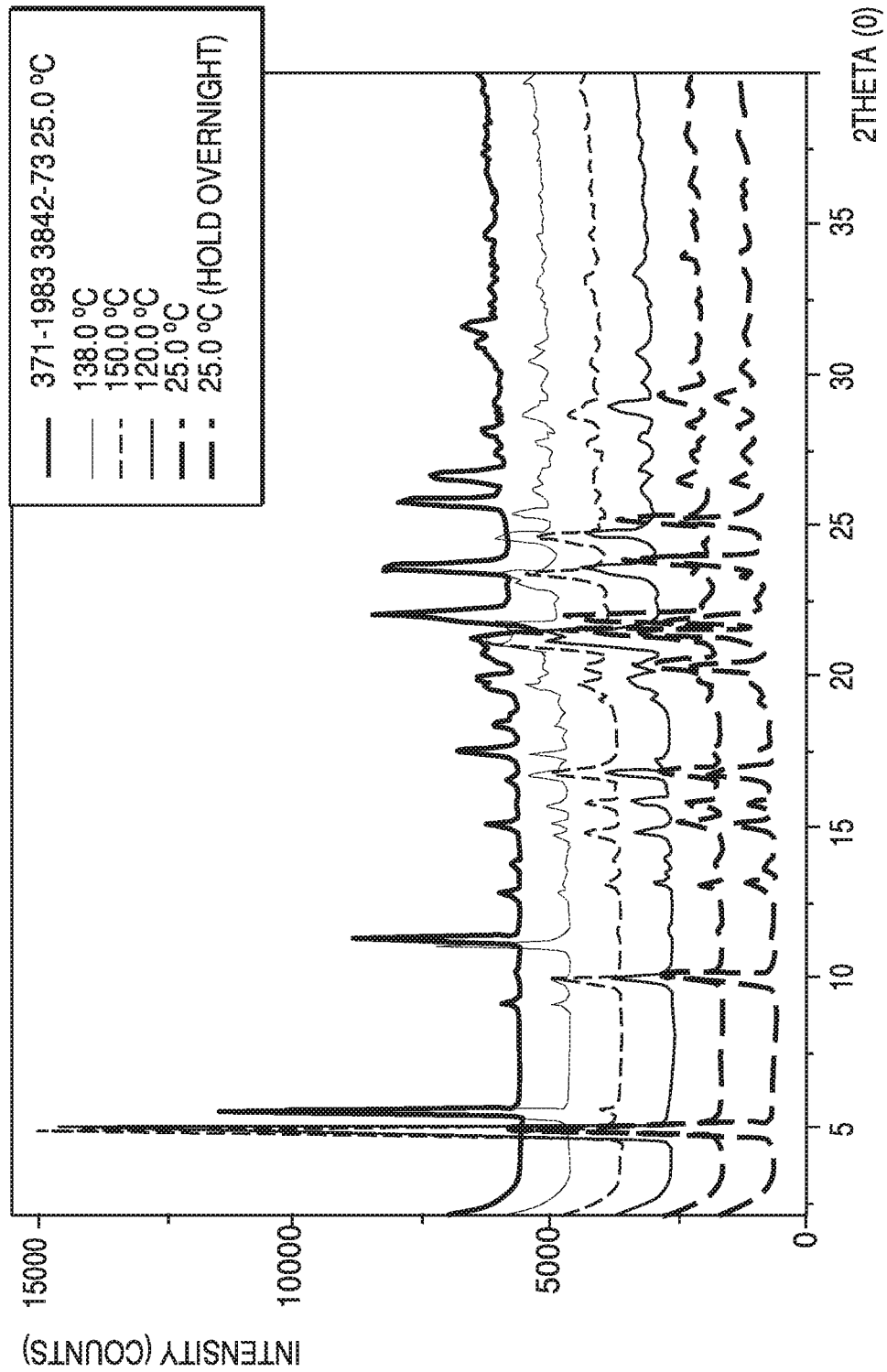
FIG. 12 shows a variable temperature XRPD plot of Compound I Form III from about 150° C. to about 25° C., and that Compound I remains as Form III.

Form III was generated at 138° C. from Form I in a variable temperature XRD (VT XRD) experiment. Form III is stable when cooled to 25° C. and does not convert back to Form I. Form III was converted back to Form I in a competition slurry experiment with Form I in methanol within about 2 weeks (10 mg of each of Form I and Form III in methanol). Form III is characterized by the X-ray powder diffraction pattern in FIG. 9, and the differential scanning calorimetry plot in FIG. 11 showing endotherms at about 181 and 271° C. (decomposition).

Form IV was generated between 95 and 110° C. from Form II in a variable temperature XRD experiment. Form IV converts back to Form II when cooled to 25° C. in the VT XRD experiment. Form III is characterized by the X-ray powder diffraction pattern in FIG. 13.

Example 2. Preparation of Form I

Compound I Form I was prepared by dissolving Compound I in a methanol/dichloromethane mixture (33% MeOH/DCM) followed by reducing the volume and dichloromethane content by distillation. Solids were collected by vacuum filtration, resulting in Compound I Form I, as identified by XRPD.

Example 3. Preparation of Form II

Compound I Form II was made by slurrying Compound I Form I in chloroform at ambient temperature and pressure for 5 days. Solids were collected by vacuum filtration, resulting in Compound I Form II, as identified by XRPD. Compound I Form II was also prepared by cooling Compound I Form IV to approximately 25° C. during VT-XRPD analysis. Compound I Form II was also prepared by heating Compound I Form XIII to approximately 11° C.

Example 4. Preparation of Form III

Compound I Form III was made by heating Compound I Form I to approximately 150° C. during VT-XRPD analysis. Compound I Form III was also prepared at a lower temperature during VT-XRPD analysis when Compound I Form I was heated to and held at 100° C.

Example 5. Preparation of Form IV

Compound I Form IV was made by heating Compound I Form II to approximately 95° C. to 110° C. during VT-XRPD analysis. Compound I Form IV was also prepared during VT-XRPD analysis when Compound I Form III was heated to approximately 180° C.

Example 6. Preparation of Form V

Compound I Form V was made by forming a solution of Compound I in HFIPA (hexafluoroisopropanol), and evaporating to dryness. An alternative way of preparing Form V is to pour the solution of Compound I in HFIPA at 100° C. into cold water and isolate the solid.

Example 7. Preparation of Form VI

Compound I Form V was made by forming a solution of Compound I in TFE (2,2,2-trifluoroethanol), and evaporating to dryness.

Example 8. Preparation of Form VII

Compound I Form V was made by forming a solution of Compound I in TFE (2,2,2-trifluoroethanol), and evaporating to dryness.

Example 9. Preparation of Form VIII

Compound I Form V was made by exposing Form V or Form VII to 97% RH at room temperature for 1 week.

Example 10. Preparation of Form IX

Form IX was made by slurring approximately Form I of Compound I in 5:1 TFE/water at ambient temperature for 5 days. Solids were collected by vacuum filtration and dried under reduced pressure for a couple minutes, resulting in Form IX, as identified by XRPD.

Example 11. Preparation of Form X

Form X was made by dissolving approximately Form I of Compound I in chloroform. The resulting solution was filtered through a 0.2 µm nylon filter and placed in the CentriVap. The sample was centrifuged under vacuum for approximately 30 minutes at ambient temperature. The resulting solids were identified as Form X by XRPD.

Example 12. Preparation of Form XI

Form XI was made by dissolving Form I of Compound I in HFIPA. Methanol was then added to the solution, which resulted in a cloudy, white suspension. Solids were collected by vacuum filtration and dried under reduced pressure, and were identified as Form XI by XRPD.

Example 13. Preparation of Form XII

Form XII was made by forming a slurry of Form I of Compound I in 10:1 TFE/water at ambient temperature for 3 days. Solids were collected by vacuum filtration and dried under reduced pressure, and were identified as Form XII by XRPD.

Example 14. Preparation of Form XIII

Form XIII was made by cooling Form II to −10° C.

Example 15. Preparation of Form XIV

Form XIV was made by exposing Form XII of Compound I to vacuum under ambient conditions for three days, then exposing the sample to 40° C. for approximately two hours. Resulting solids were identified as Form XIV by XRPD.

Although the foregoing invention has been described in some detail by way of illustration and example for purposes of clarity of understanding, one of skill in the art will appreciate that certain changes and modifications may be practiced within the scope of the appended claims. In addition, each reference, including all of the U.S. patents, U.S. patent application publications, U.S. patent applications, foreign patents, foreign patent applications and non-patent publications referred to in this specification are incorporated herein by reference, in their entirety, to the extent not inconsistent with the present description. Where a conflict exists between the instant application and a reference provided herein, the instant application shall dominate.

What is claimed is:

1. A crystalline form of Compound I having the structure:

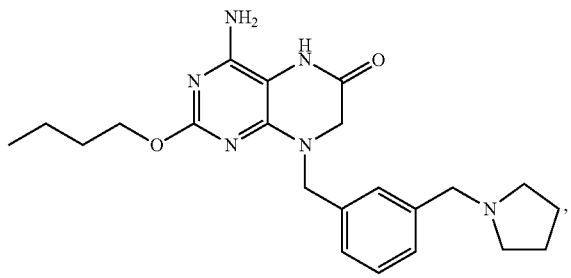 [SMILES: CCCCOc1nc(N)c2c(n1)N(Cc1cccc(CN3CCCC3)c1)CC(=O)N2]

characterized by an X-ray powder diffraction (XRPD) pattern comprising three or more peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation.

2. The crystalline form of claim 1, characterized by an XRPD pattern comprising peaks at 5.3, 9.8 and 15.6 degrees 2θ (±0.2 degrees 2θ), wherein the XRPD is made using CuK$_{\alpha 1}$ radiation.

3. The crystalline form of claim 1, characterized by an XRPD pattern comprising peaks at 5.3, 9.8, 13.1, 15.6, 17.0, 19.6, 20.0, 20.7, 21.9 and 24.9 degrees 2θ (±0.2 degrees 2θ), wherein the XRPD is made using CuK$_{\alpha 1}$ radiation.

4. The crystalline form of claim 1, characterized by the XRPD pattern substantially in accordance with that of FIG. 20.

5. The crystalline form of claim 1, characterized by a differential scanning calorimetry (DSC) endotherm at about 141° C. or about 173° C.

6. The crystalline form of claim 1, characterized by
   an XRPD pattern comprising peaks at 5.3, 9.8, 13.1, 15.6, 17.0, 19.6, 20.0, 20.7, 21.9 and 24.9 degrees 2θ (±0.2 degrees 2θ), wherein the XRPD is made using CuK$_{\alpha 1}$ radiation; and
   a DSC endotherm at about 173° C.

7. A method of preparing a crystalline form of claim 1, comprising:
   forming a mixture comprising a crystalline Form I of Compound I characterized by an XRPD pattern comprising three or more peaks at 5.8, 11.4, 11.6, 17.7, 20.1, 20.9, 22.3, 23.9, 26.0 or 26.8 degrees 2θ (±0.2 degrees 2θ), wherein the XRPD is made using CuK$_{\alpha 1}$ radiation, water and trifluoroethanol, under conditions suitable to prepare the crystalline form of claim 1.

8. The method of claim 7, wherein the ratio of trifluoroethanol to water is from about 10:1 to about 1:1 (volume/volume).

9. The method of claim 7, wherein the ratio of trifluoroethanol to water is about 5:1 (volume/volume).

10. A pharmaceutical composition comprising a therapeutically effective amount of a crystalline form of Compound I of claim 1, and a pharmaceutically acceptable carrier or excipient.

11. The pharmaceutical composition of claim 10, further comprising at least one additional therapeutic agent.

12. The crystalline form of claim 1, characterized by an X-ray powder diffraction (XRPD) pattern comprising four or more peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation.

13. The crystalline form of claim 1, characterized by an X-ray powder diffraction (XRPD) pattern comprising five or more peaks at 5.3, 9.8, 13.1, 15.6, 17.0, 19.6, 20.0, 20.7, 21.9 or 24.9 degrees 2θ (±0.2 degrees 2θ), wherein the XRPD is made using CuK$_{\alpha 1}$ radiation.

14. The crystalline form of claim 2, characterized by an XRPD pattern further comprising one or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation.

15. The crystalline form of claim 2, characterized by an XRPD pattern further comprising two or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation.

16. The crystalline form of claim 2, characterized by an XRPD pattern further comprising three or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation.

17. The crystalline form of claim 2, characterized by an XRPD pattern further comprising four or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation.

18. The crystalline form of claim 2, characterized by an XRPD pattern further comprising five or more peaks at 13.1, 17.0, 19.6, 20.0, 20.7, 21.9 or 24.9 degrees 2θ (±0.2 degrees 2θ), wherein the XRPD is made using CuK$_{\alpha 1}$ radiation.

* * * * *